(12) United States Patent
Johnson et al.

(10) Patent No.: US 12,012,434 B2
(45) Date of Patent: Jun. 18, 2024

(54) MUTANT TRANSPORTERS FOR BACTERIAL UPTAKE OF TEREPHTHALIC ACID

(71) Applicants: Alliance for Sustainable Energy, LLC, Golden, CO (US); University of Georgia Research Foundation, Inc., Athens, GA (US)

(72) Inventors: Christopher W. Johnson, Denver, CO (US); Gregg Tyler Beckham, Golden, CO (US); Isabel Pardo Mendoza, Dos Hermanas (ES); Ellen Lee Neidle, Dacula, GA (US)

(73) Assignees: Alliance for Sustainable Energy, LLC, Golden, CO (US); University of Georgia Research Foundation, Inc., Athens, GA (US)

( * ) Notice: Subject to any disclaimer, the term of this patent is extended or adjusted under 35 U.S.C. 154(b) by 149 days.

(21) Appl. No.: 17/472,936

(22) Filed: Sep. 13, 2021

(65) Prior Publication Data
US 2022/0089654 A1    Mar. 24, 2022

Related U.S. Application Data

(60) Provisional application No. 63/077,173, filed on Sep. 11, 2020.

(51) Int. Cl.
*C07K 14/195*    (2006.01)

(52) U.S. Cl.
CPC .................. *C07K 14/195* (2013.01)

(58) Field of Classification Search
None
See application file for complete search history.

(56) References Cited

U.S. PATENT DOCUMENTS

| | | |
|---|---|---|
| 4,952,501 A | 8/1990 | Jasin et al. |
| 11,091,782 B2 | 8/2021 | Zhang et al. |
| 2017/0096689 A1* | 4/2017 | Burk .............. C12Y 402/01002 |

FOREIGN PATENT DOCUMENTS

WO    2019/222396 A1    11/2019

OTHER PUBLICATIONS

Williams et al. Journal of Bacteriology, vol. 179, No. 18, pp. 5935-5942, 1997 (Year: 1997).*
Choi et al. FEMS Microbiology Letters, vol. 252, pp. 207-213, 2005. (Year: 2005).*
Austin et al., "Characterization and engineering of a plastic-degrading aromatic polyesterase", Proceedings of the National Academy of Sciences of the United States of America, May 2018, vol. 115, No. 19, pp. E4350-E4357.
Beckham et al., "Opportunities and challenges in biological lignin valorization", Current Opinion in Biotechnology, Dec. 2016, vol. 42, pp. 40-53.
Bentley et al., "Engineering glucose metabolism for enhanced muconic acid production in Pseudomonas putida KT2440", May 2020, Metabolic Engineering, vol. 59, pp. 64-75.
Bleichrodt et al., "The β-ketoadipate pathway of Acinetobacter baylyi undergoes carbon catabolite repression, cross-regulation and vertical regulation, and is affected by Crc", Microbiology, May 2010, vol. 156, Pt 5, pp. 1313-1322.
Chain et al., "Burkholderia xenovorans LB400 harbors a multi-replicon, 9.73-Mbp genome shaped for versatility", Proceedings of the United States of the United States of America, 2006, vol. 103, vol. 42, pp. 15280-15287.
Choi et al., "Molecular and biochemical analysis of phthalate and terephthalate degradation by *Rhodococcus* sp. strain DK17", FEMS Microbiology Letters, Nov. 2005, vol. 252, No. 2, pp. 207-213.
De Berardinis et al., "A complete collection of single-gene deletion mutants of Acinetobacter baylyi ADP1", Molecular Systems Biology, 2008, vol. 4, No. 174, pp. 1-15.
Franden et al., "Engineering Pseudomonas putida KT2440 for efficient ethylene glycol utilization", Metabolic Engineering, Jul. 2018, vol. 48, pp. 197-207.
Guzmán et al., "Enzyme promiscuity shapes adaptation to novel growth substrates", Molecular Systems Biology, Apr. 2019, vol. 15, No. 4, pp. 1-14.
Hara et al., "Transcriptomic analysis reveals a bifurcated terephthalate degradation pathway in *Rhodococcus* sp. strain RHA1", Journal of Bacteriology, Mar. 2007, vol. 189, No. 5, pp. 1641-1647.
Hierro Acero et al., "Enzymatic surface hydrolysis of PET: Effect of structural diversity on kinetic properties of cutinases from Thermobifida", Macromolecules, 2011, vol. 44, No. 12, pp. 4632-4640.
Hosaka et al., "Novel Tripartite Aromatic Acid Transporter Essential for Terephthalate Uptake in *Comamonas* sp. Strain E6", Applied and Environmental Microbiology, Oct. 2013, vol. 79, No. 19, pp. 6148-6155.
Jha et al., "Engineering an Acinetobacter regulon for biosensing and high-throughput enzyme screening in *E. coli* via flow cytometry", Nucleic Acids Research, 2014, vol. 42, No. 12, pp. 8150-8160.
Jha et al., "A protocatechuate biosensor for Pseudomonas putida KT2440 via promoter and protein evolution", Metabolic Engineering Communications, Jun. 2018, vol. 6, pp. 33-38.
Johnson et al., "Aromatic catabolic pathway selection for optimal production of pyruvate and lactate from lignin", Metabolic Engineering, Mar. 2015, vol. 28, pp. 240-247.
Johnson et al., "Innovative chemicals and materials from bacterial aromatic catabolic pathways", Joule, Jun. 2019, vol. 3, No. 6, pp. 1523-1537.
Joo et al., "Structural insight into molecular mechanism of poly-(ethylene terephthalate) degradation", Nature Communications, Jan. 2018, vol. 9, No. 382, pp. 1-12.

(Continued)

*Primary Examiner* — Jana A Hines
*Assistant Examiner* — Khatol S Shahnan Shah
(74) *Attorney, Agent, or Firm* — Michael A. McIntyre

(57) ABSTRACT

The present disclosure relates to a non-naturally occurring microorganism that includes a gene encoding a MucK transporter protein, where the microorganism is capable of catabolizing terephthalic acid (TPA). In some embodiments of the present disclosure, the gene encoding the MucK transporter protein may contain at least one mutation, relative to a reference gene encoding a reference MucK transporter protein.

18 Claims, 24 Drawing Sheets

Specification includes a Sequence Listing.

(56) References Cited

OTHER PUBLICATIONS

Kasai et al., "Transcriptional Regulation of the Terephthalate Catabolism Operon in *Comamonas* sp. Strain E6", Applied and Environmental Microbiology, Sep. 2010, vol. 76, No. 18, pp. 6047-6055.
Kenny et al., "Up-cycling of PET (Polyethylene Terephthalate) to the biodegradable plastic PHA (Polyhydroxyalkanoate)", Environmental Science & Technology, 2008, vol. 42, No. 20, pp. 7696-7701.
Kenny et al., "Development of a bioprocess to convert PET derived terephthalic acid and biodiesel derived glycerol to medium chain length polyhydroxyalkanoate", Applied Microbiology and Biotechnology, 2012, vol. 95, No. 3, pp. 623-633.
Li et al., "Laboratory evolution reveals the metabolic and regulatory basis of ethylene glycol metabolism by Pseudomonas putida KT2440", Environmental Microbiology, 2019, vol. 21, No. 10, pp. 3669-3682.
Linger et al., "Lignin valorization through integrated biological funneling and chemical catalysis", Proceedings of the United States of America, 2014, vol. 111, No. 33, pp. 12013-12018.
Metzgar et al., "*Acinetobacter* sp. ADP1: an ideal model organism for genetic analysis and genome engineering", Nucleic Acids Research, 2004, vol. 32, No. 19, pp. 5780-5790.
Mückschel et al., "Ethylene glycol metabolism by Pseudomonas putida", Applied and Environmental Microbiology, Dec. 2012, vol. 78, No. 24, pp. 8531-8539.
Palm et al., "Structure of the plastic-degrading Ideonella sakaiensis MHETase bound to a substrate", Nature Communications, Apr. 2019, vol. 10, pp. 1-10.
Parke et al., "Cloning and genetic characterization of dca genes required for oxidation of straight-chain dicarboxylic acids in *Acinetobacter* sp. strain ADP1", Applied and Environmental Microbiology, Oct. 2001, vol. 67, No. 10, pp. 4817-4827.
Patrauchan et al., "Catabolism of benzoate and phthalate in *Rhodococcus* sp. strain RHA1: Redundancies and convergence", Journal of Bacteriology, 2005, vol. 187, No. 12, pp. 4050-4063.
Ribitsch et al., "Characterization of a new cutinase from Thermobifida alba for PET-surface hydrolysis", Biocatalysis and Biotransformation, 2012, vol. 30, No. 1, pp. 2-9.
Ronkvist et al., Cutinase-catalyzed hydrolysis of poly(ethylene terephthalate). Macromolecules, 2009, vol. 42, No. 14, pp. 5128-5138.
Rorrer et al., "Combining reclaimed PET with bio-based monomers enables plastics upcycling", Joule, Apr. 2019, vol. 3, No. 4, pp. 1006-1027.
Sasoh et al., "Characterization of the Terephthalate Degradation Genes of *Comamonas* sp. Strain E6", Applied and Environmental Microbiology, Mar. 2006, vol. 72, No. 3, pp. 1825-1832.
Shigematsu et al., "Purification and gene cloning of the oxygenase component of the terephthalate 1,2-dioxygenase system from Delftia tsuruhatensis strain T7", FEMS Microbiology Letters, 2003, vol. 220, No. 2, pp. 255-260.
Sulaiman et al., "Isolation of a novel cutinase homolog with polyethylene terephthalate-degrading activity from leaf-branch compost by using a metagenomic approach", Applied and Environmental Microbiology, 2012, vol. 78, No. 5, pp. 1556-1562.
Tumen-Velasquez et al., "Accelerating pathway evolution by increasing the gene dosage of chromosomal segments", Proceedings of the National Academy of Sciences of the United States of America, Jul. 2018, vol. 115, No. 27, pp. 7105-7110.
Vermaas et al., "Passive membrane transport of lignin-related compounds", Proceedings of the National Academy of Sciences of the United States of America, 2019, vol. 116, No. 46, pp. 23117-23123.
Wang et al., "Molecular analysis of isophthalate and terephthalate degradation by Comamonas testosteroni YZW-D", Environmental Health Perspectives, 1995, vol. 103, Suppl. 5, pp. 9-12.
Williams et al., "mucK, a Gene in Acinetobacter calcoaceticus ADP1 (BD413), Encodes the Ability To Grow on Exogenous cis,cis-Muconate as the Sole Carbon Source", Journal of Bacteriology, Sep. 1997, vol. 179, No. 18, pp. 5935-5942.
Yoshida et al., "A bacterium that degrades and assimilates poly(ethylene terephthalate)", Science, 2016, vol. 351, No. 6278, pp. 1196-1199.

\* cited by examiner

SEQ ID NO: 16

```
atggatctta ttcaaaactt aagtaccggc ttcggtgtgg cttcacttt ccaaaatttg      60
atttattgtt tcgttggttg tcttttaggt actttaattg gcgtacttcc aggcattggt    120
ccagttgcta caattgcaat gttattgcct gcaacctatg ctttaccacc agtggctgca    180
ttgattatgt tggctggtat ctactatggt gcgcagtatg gtggtagtac tactgctatt    240
ttggtaaatc ttccgggtga atcttcttct gtagtcaccg ttatcgatgg ttaccaaatg    300
gctcgtaaag tcgtgcagg tccagcgctt gctgctgctg gtattggttc ttttttcgca    360
ggttgtgttg gtacagtgat cttagcggct ttcgctccac ctctcacgga agttgcattc    420
aagtttggac ctgcagagta ttttcttta atgacattgg gtctaattgg tgcagttgtc    480
cttgcttcag gctctttgct caaagcaatt gcaatgatcg tactcggtct tttgcttggc    540
atggttggta cggacgtaaa ttcaggtgta gcgcgttact catttgacat tccagagcta    600
acagatggta ttgattttgt tgtgatcgca atgggtgttt ttggttacgg tgaaattatt    660
gcaaatcttt caaagcctga tgatgaacgt gaggtttttg cagcgaaagt gactggtctt    720
cttccaacaa gtgaagactt caaacgtatg ttgccagcaa tgttgcgtgg tacagcatta    780
ggttcagctt taggaatttt gccaggtggt ggtgctatgt tgagtgcatt tgcagcttat    840
acaattgaaa aaaaaccaa attaaaacct ggtgaagtac catttggtca gggcaatatt    900
cgtggcgttt gcgctccgga atcagcaaac aacgctggta gtcaaacatc tttcattcca    960
ctgttaacat tgggcattcc tccaaacgcc gtaatggctc tcatggtagg cgcaatgact   1020
attcacaaca ttcaaccagg accacaagtg atgacatcta accctgaact attttgggggt  1080
cttattgcaa gcatgtagat tggtaatttg atgttaatta ttttgaacct accacttatc   1140
ggtgtgtgga tcaagttgct tacagtacca tatcgttggt tgtttccatc tatcgtatta   1200
ttttgtgcaa ttggtgtgta tggtactaat aacaacgttt gggatgtttg gatggtaggt   1260
atttttggtt tcattggtta tgtattccac aagttaggga ctgaacctgc tcctttgttg   1320
ttgggtttca ttttaggtcc aatgatggaa gaaaaccttc gccgtgctct attgctatcg   1380
cgtggcgact ggtctgtatt tgttacgcgt ccaattagtg catgcttact ggcagcggct   1440
gttgtgcttc ttgtaatcgt tcttatgcct gcagttaaga ataaacgtga agaggccttt   1500
gtagaagatt ga                                                       1512
```

SEQ ID NO: 17

```
MDLIQNLSTG FGVAFTFQNL IYCFVGCLLG TLIGVLPGIG PVATIAMLLP ATYALPPVAA     60
LIMLAGIYYG AQYGGSTTAI LVNLPGESSS VVTVIDGYQM ARKGRAGPAL AAAGIGSFFA   120
GCVGTVILAA FAPPLTEVAF KFGPAEYFSL MTLGLIGAVV LASGSLLKAI AMIVLGLLLG   180
MVGTDVNSGV ARYSFDIPEL TDGIDFVVIA MGVFGYGEII ANLSKPDDER EVFAAKVTGL   240
LPTSEDFKRM LPAMLRGTAL GSALGILPGG GAMLSAFAAY TIEKKTKLKP GEVPFGQGNI   300
RGVCAPESAN NAGSQTSFIP LLTLGIPPNA VMALMVGAMT IHNIQPGPQV MTSNPELFWG   360
LIASMIGNLM LIILNLPLIG VWIKLLTVPY RWLFPSIVLF CAIGVYGTNN NVWDVWMVGI   420
FGFIGYVFHK LGTEPAPLLL GFILGPMMEE NLRRALLLSR GDWSVFVTRP ISACLLAAAV   480
VLLVIVLMPA VKNKREEAFV ED                                            502
```

Figure 6

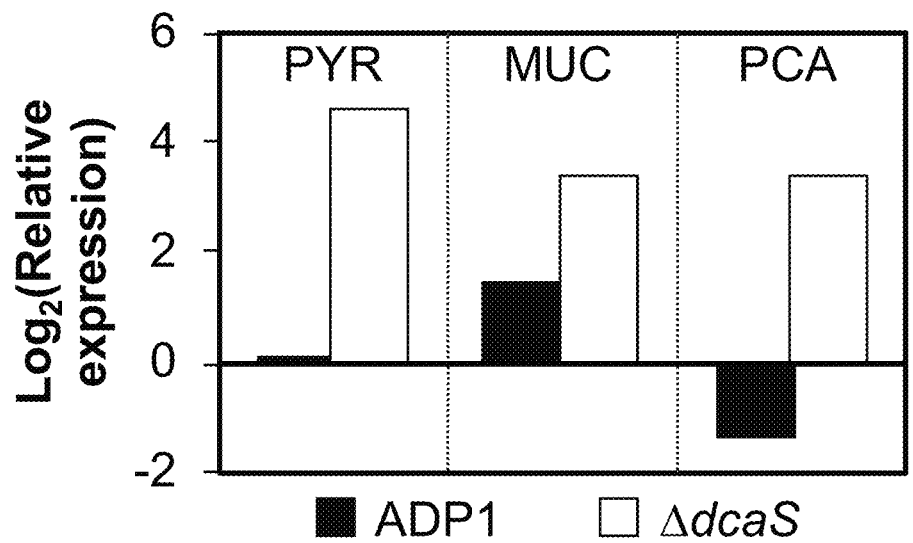
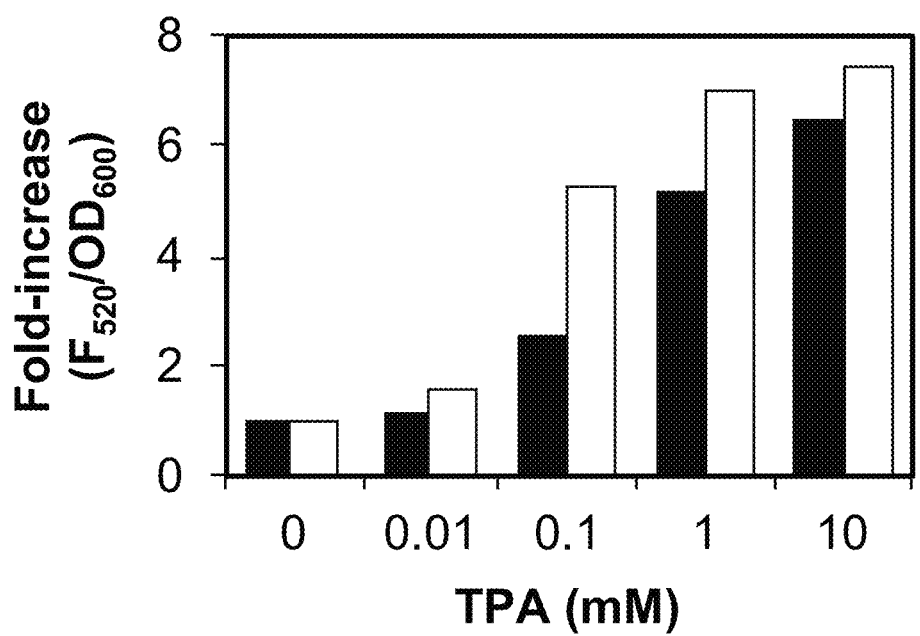
Figure 14B

```
TpaK_RHA1    MSLAPSRVTLPDFIDSRPVSR--------YQ-YIVIALCGVVMFIDGFDTQSISYMAPHI   51
TpaK_DK17    MSLAPSRVTLPDFIDSRPVSR--------YQ-YIVIALCGVVMFIDGFDTQSISYMAPHI   51
TpaK_LB400   --MASPLIDVVEVIERQKVGI--------GQ-                               49
MucK_wt      ---------MYSNNQRSRIGS--------HTWKIAFLFAFLALLVDGADLMLLSYSLNSI   43
MucK_IP243   ---------MYSNNQRSRIGS--------HTWKIAFLFAFLALLVDGADLLLLSYSLNSI   43
MucK_IP246   ---------MYSNNQRSRIGS--------HTWKIAFLFAFLALLVDGADLMLLSYSLNSI   43
MucK_IP255   ---------MYSNNQRSRIGS--------HTWKIAFLFAFLALLVDGADLMLLSYSLNSI   43
MucK_IP258   ---------MYSNNQRSRIGS--------HTWKIAFLFAFLALLVDGADLILLSYSLNSI   43
GudP_wt      ----------MDNLQTSAVSISKVRVTHNKTRYYILAMIFLVTALNYGDRATISMAATPM   50
GudP_IP247   ----------MDNLQTSAVSISKVRVTHNKTRYYILAMIFLVTALNYGDRATISMAATPM   50
GudP_IP250   ----------MDNLQTSAVSISKVRVTHNKTRYYILAMIFLVTALNYGDRATISMAATPM   50
                       .  :   :.              . :  :   ::   *    :*       :

TpaK_RHA1    AEEWGLSKQVLGPIFSAALAGLMVGYLALSPLSERFGHRRMILTSTVIFALGTLAAAWSQ  111
TpaK_DK17    AEEWGLSKQVLGPIFSAALAGLMVGYLALSPLSERFGHRRMILTSTVIFALGTLAAAWSQ  111
TpaK_LB400   SKDWHLPREVLGSIFSAALVGLMVGYLAIAPLSARFGHKRMMLASSVLFALFTLLTLFAT  109
MucK_wt      KAEFNLSTVEAGMLGSFTLAGMAIGGIFGGWACDRFGRVRIVVISILTFSILTCGLGLTQ  103
MucK_IP243   KAEFNLSTVEAGMLGSFTLAGMAIGGIFGGWACDRFGRVRIVVISILTFSILTCGLGLTQ  103
MucK_IP246   KAEFNLSTVEAGMLGSFTLAGMAIGGIFGGWACDRFGRVRIVVISILTFSILTCGLGLTQ  103
MucK_IP255   KAEFNLSTVEAGMLGSFTLAGMAIGGIFGGWACDRFGRVRIVVISILTFSILTCGLGLTQ  103
MucK_IP258   KAEFNLSTVGAGMLGSFTLAGMAIGGIFGGWACDRFGRVRIVVISILTFSILTCGLGLTQ  103
GudP_wt      SQELGLTSVTMGYIFSAFGWAYVIGQVPGGWLLDKFGARKVYFWSILLWSIFTVLLGFVD  110
GudP_IP247   SQELGLTSVTMGYIFSAFGWAYVIGQVPGGWLLDKFGARKVYFWSILLWSIFTVLLGFVD  110
GudP_IP250   SQELGLTSVTMGYIFSAFGWAYVIGQVPGGWLLDKFGARKVYFWSILLWSIFTVLLGFVD  110
               :    *       *  :  *    . :*       :  :**    ::  .  *   :  :::  *

TpaK_RHA1    NV-------TELMALRFITGMGLGAAAPSAIALTGEFSPKRLRATFVLVIYCGFSLGFVA  164
TpaK_DK17    NV-------TELMALRFITGMGLGAAAPSAIALTGEFSPKRLRATFVLVIYCGFSLGFVA  164
TpaK_LB400   NV-------TELIGLRFLTGIGLGAAAPSAVALTCEFAPKRLRATFVLLVYCGFSLGFVV  162
MucK_wt      SF-------IQFGVLRFFASLGLGSLYIACNTLMAEYVPTKYRTTVLGTLQAGWTVGYIV  156
MucK_IP243   SF-------IQFGVLRFFASLGLGSLYIACNTLMAEYVPTKYRTTVLGTLQAGWTVGYIV  156
MucK_IP246   SF-------IQFGVLRFFASLGLGSLYIACNTLMAECVPTKYRTTVLGTLQAGWTVGYIV  156
MucK_IP255   SF-------IQFGVLRFFASLGLGSLYIACNTLMAEYVPTKYRTTVLGTLQAGCTVGYIV  156
MucK_IP258   SF-------IQFGVLRFFASLGLGSLYIACNTLMAEYVPTKYRTTVLGTLQAGWTVGYIV  156
GudP_wt      IFGSIPLIIASLFILRFLVGLSESPAFPGNSQIVAAWFPTKERGTAAASFNSAQYFATVI  170
GudP_IP247   IFGSIPLIIASLFILRFLVGLSESPAFPGNSQIVAAWFPTKERGTAAASFNSAQYFATVI  170
GudP_IP250   IFGSIPLIIASLFILRFLVGLSESPAFPGNSQIVAAWFPTKERGTAAASFNSAQYFATVI  170
              .         .: ***:..:.  .      :      *.:  * *     . ..  .. :

TpaK_RHA1    AGLVSGWLIPILGWRSVLVVGAVAPLLLLPALL--RYLPDSLTSMINRGAEPNRIQAIFR  222
TpaK_DK17    AGLVSGWLIPILGWRSVLVVGAVAPLLLLPALL--RYLPDSLTSMINRGAEPNRIQAIFR  222
TpaK_LB400   AGLTAGALMPAFGWKSLMLVGALAPIALTVPLA--WLLPESLVVLQRRPNGDERMRAVLL  220
MucK_wt      ATLLAGWLIPDHGWRVLFYVAI-IPVLMAVLMH--FFVPEPAAWQQSRLA----------  203
MucK_IP243   ATLLAGWLIPDHGWRVLFYVAI-IPVLMAVLMH--FFVPEPAAWQQSRLA----------  203
MucK_IP246   ATLLAGWLIPDHGWRVLFYVAI-IPVLMAVLMH--FFVPEPAAWQQSRLA----------  203
MucK_IP255   ATLLAGWLIPDHGWRVLFYVAI-IPVLMAVLMH--FFVPEPAAWQQSRLA----------  203
MucK_IP258   ATLLAGWLIPDHGWRVLFYVAI-IPVLMAVLMH--FFVPEPAAWQQSRLA----------  203
GudP_wt      FAPFMGWLVTHIHWQSVFWIMGAIGIVIAFIWLKVIYSPEKHP----RINKEEL--TYLQ  224
GudP_IP247   FAPFMGWLVTHIHWQSVFWIMGAIGIVIAFIWLKVIYSPEKHP----RINKEEL--TYLQ  224
GudP_IP250   FAPFMGWLVTHIHWQSVFWIMGAIGIVIAFIWLKVIYSPEKHP----RINKEEL--TYLQ  224
                  * *:      *:  ::  :       : :          *:           *

TpaK_RHA1    KMDPALAVGPDITYEAEKRTDGQR-TALRSLFTRDRVLGTLLLWLVFVI-NLGEFYALQS  280
TpaK_DK17    KMDPALAVGPDITYEAEKRTDGQR-TALRSLFTRDRVLGTLLLWLVFVI-NLGEFYALQS  280
TpaK_LB400   GFFPRLDVPVGSRFRLEDQGE-AR-ASVTALVRGRTSAGTLLLWLIFFL-NLAEFYFMQS  277
MucK_wt      ---------------PSKQTETVKTSAFKLIFQDKRNRNMFILWALTAGFLQFGYYGVNN  248
MucK_IP243   ---------------PSKQTETVKTSAFKLIFQDKRNRNMFILWALTAGFLQFGYYGVNN  248
MucK_IP246   ---------------PSKQTETVKTSAFKLIFQDKRNRNMFILWALTAGFLQFGYYGVNN  248
MucK_IP255   ---------------PSKQTETVKTSAFKLIFQDKRNRNMFILWALTAGFLQFGYYGVNN  248
MucK_IP258   ---------------PSKQTETVKTSAFKLIFQDKRNRNMFILWALTAGFLQFGYYGVNN  248
GudP_wt      GNGAITSMGEN-KSKTLDQKNKMSWSNVKKLLSSRMLLGIFIAQY----CITCLTYFFLT  279
GudP_IP247   GNGAITSMGEN-KSKTLDQKNKMSWSNVKKLLSSRMLLGIFIAQY----CITCLTYFFLT  279
GudP_IP250   GNGAITSMGEN-KSKTLDQKNKMSWSNVKKLLSSRMLLGIFIAQY----CITCLTYFFLT  279
                .:  :       :  . :.    . ::            *          * ..
```

Figure 18A

```
TpaK_RHA1    WLPSIMTSL---DYDMGTVVTATTLTTVGGIAAAFVTGPCMDRLGAYVTLG-----TVYV    332
TpaK_DK17    WLPSIMTSL---DYNMGTVVTATTLTTVGGIAAAFVTGPCMDRLGAYVTLG-----TVYV    332
TpaK_LB400   WLPTMLTGL---QYSPATVVWVTALPTIAGVLSAVPLGLAMDRVGPYVTLT-----VMYL    329
MucK_wt      WMPSYLESELGMKFKEMTAYMVGTY--TAMILGKILAGFMADKLGRRFTYA-----FGAI    301
MucK_IP243   WMPSYLESELGMKFKEMTAYMVGTY--TAMILGKILAGFMADKLGRRFTYA-----FGAI    301
MucK_IP246   WMPSYLESELGMKFKEMTAYMVGTY--TAMILGKILAGFMADKLGRRFTYA-----FGAI    301
MucK_IP255   WMPSYLESELGMKFKEMTAYMVGTY--TAMILGKILAGFMADKLGRRFTYA-----FGAI    301
MucK_IP258   WMPSYLESELGMKFKEMTAYMVGTY--TAMILGKILAGFMADKLGRRFTYA-----FGAI    301
GudP_wt      WFPVYLVKERHMTIL--QAGFAAVLPALCGFIGGILGGIISDRLIRMNKSLSFSRKFPIV    337
GudP_IP247   WFPVYLVKECHMTIL--QAGFAAVLPALCGFIGGILGGIISDRLIRMNKSLSFSRKFPIV    337
GudP_IP250   WFPVYLVKERHMTIL--QAGFAAVLPALCGFIGGILGGIISDRLIRMNKSLSFSRKFPIV    337
             *:*    :                ...    ...  *   *::   .         :

TpaK_RHA1    VGFAF-VALTGVAFTAP----LWVLLTANFFAGVCISGGQKSLIALSAVFYPTPMRSTGV    387
TpaK_DK17    VGFAF-VALTGVAFTAP----LWVLLTANFFAGVCISGGQKSLIALSAVFYPTPMRSTGV    387
TpaK_LB400   AGCVF-MWLVGGAFSGS----VAWLMVMVFCAGFCISGGQKSVIALAAVYYPLNLRSTGV    384
MucK_wt      GTAIF-LPLI-VFYNSP-DNILYLLVIFGFLYGIP--YGV--NATYMTESFPTAIRGTAI    354
MucK_IP243   GTAIF-LPLI-VFYNSP-DNILYLLVIFGFLYGIP--YGV--NATYMIESFPTAIRGTAI    354
MucK_IP246   GTAIF-LPLI-VFYNSP-DNILYLLVIFGFLYGIP--YGV--NATYMTESFPTAIRGTAI    354
MucK_IP255   GTAIF-LPLI-VFYNSP-DNILYLLVIFGFLYGIP--YGV--NATYMTESFPTAIRGTAI    354
MucK_IP258   GTAIF-LPLI-VFYNSP-DNILYLLVIFGFLYGIP--YGV--NATYMTESFPTAIRGTAI    354
GudP_wt      LGMLLSTSIIVCNYVDSQTAIVFFMSLAFFGKGFGAL-----GWAVMSDVAPKEMIGLSG    392
GudP_IP247   LGMLLSTSIIVCNYVDSQTAIVFFMSLAFFGKGFGAL-----GWAVMSDVAPKEMIGLSG    392
GudP_IP250   LGMLLSTSIIVCNYVDSQTAIVFFMSLAFFGKGFGAL-----GWAVMSDVAPKEMIGLSG    392
                :     :     :    :   :     *  *.         :     *   :..

TpaK_RHA1    GWALGVGRLGGIVGPIAVGAALGMGWSASAVFYAMSVPMLVA-GAAVFLLGRWVRSDNHP    446
TpaK_DK17    GWALGVGRLGGIVGPIAVGAALGMGWSASAVFYAMSVPMLVA-GAAVFLLGRWVRSDNHP    446
TpaK_LB400   GWALGIGRLGGIAGPLSAGMLYSAHWTPAEIFRFSAWPVLIA-GLAVFVMGRIYGSRPVA    443
MucK_wt      GGAYNVGRLGAAIAPATIGFLASGGSIG--------LGFVVM-GAAYFICGVIPALFI-K    404
MucK_IP246   GGAYNVGRLGAAIAPATIGFLASGGSIG--------LGFVVM-GAAYFICGVIPALFI-K    404
MucK_IP243   GGAYNVGRLGAAIAPATIGFLASGGSIG--------LGFVVM-GAAYFICGVIPALFI-K    404
MucK_IP255   GGAYNVGRLGAAIAPATIGFLASGGSIG--------LGFVVM-GAAYFICGVIPALFT-K    404
MucK_IP258   GGAYNVGRLGAAIAPATIGFLASGGSIG--------LGFVVM-GAAYFICGVIPALFI-K    404
GudP_wt      GLFNTFGNTAGIIIPIAIGYIVASTGSFNGALVFVGIHAIIAILCYLFVVGKIERFELKK    452
GudP_IP247   GLFNTFGNTAGIIIPIAIGYIVASTGSFNGALVFVGIHAIIAILCYLFVVGKIERFELKK    452
GudP_IP250   GLFNTFGNTAGIIIPIAIGYIVASTGSFNGALVFVGIHAIIAILCYLFVVGKIELFELKK    452
             *       .*.  ..    *  :  *       .                ::     *:  *

TpaK_RHA1    DRKSAESHSLARK*  459
TpaK_DK17    DRKSAESHSLARK*  459
TpaK_LB400   VEVSTPH*------  450
GudP_wt      VI*-----------  454
GudP_IP247   VI*-----------  454
GudP_IP250   VI*-----------  454
MucK_wt      EKQYDPQQS*----  413
MucK_IP243   EKQYDPQQS*----  413
MucK_IP246   EKQYDPQQS*----  413
MucK_IP255   EKQYDPQQS*----  413
MucK_IP258   EKQYDPQQS*----  413
```

Figure 18B

```
Muck_wt (SEQ ID NO: 2)
MYSNNQRSRI GSHTWKIAFL FAFLALLVDG ADLMLLSYSL NSIKAEFNLS TVEAGMLGSF    60
TLAGMAIGGI FGGWACDRFG RVRIVVISIL TFSILTCGLG LTQSFIQFGV LRFFASLGLG   120
SLYIACNTLM AEYVPTKYRT TVLGTLQAGW TVGYIVATLL AGWLIPDHGW RVLFYVAIIP   180
VLMAVLMHFF VPEPAAWQQS RLAPSKQTET VKTSAFKLIF QDKRNRNMFI LWALTAGFLQ   240
FGYYGVNNWM PSYLESELGM KFKEMTAYMV GTYTAMILGK ILAGFMADKL GRRFTYAFGA   300
IGTAIFLPLI VFYNSPDNIL YLLVIFGFLY GIPYGVNATY MTESFPTAIR GTAIGGAYNV   360
GRLGAAIAPA TIGFLASGGS IGLGFVVMGA AYFICGVIPA LFIKEKQYDP QQS          413

Muck_IP258 (SEQ ID NO: 4)
MYSNNQRSRI GSHTWKIAFL FAFLALLVDG ADLILLSYSL NSIKAEFNLS TVGAGMLGSF    60
TLAGMAIGGI FGGWACDRFG RVRIVVISIL TFSILTCGLG LTQSFIQFGV LRFFASLGLG   120
SLYIACNTLM AEYVPTKYRT TVLGTLQAGW TVGYIVATLL AGWLIPDHGW RVLFYVAIIP   180
VLMAVLMHFF VPEPAAWQQS RLAPSKQTET VKTSAFKLIF QDKRNRNMFI LWALTAGFLQ   240
FGYYGVNNWM PSYLESELGM KFKEMTAYMV GTYTAMILGK ILAGFMADKL GRRFTYAFGA   300
IGTAIFLPLI VFYNSPDNIL YLLVIFGFLY GIPYGVNATY MTESFPTAIR GTAIGGAYNV   360
GRLGAAIAPA TIGFLASGGS IGLGFVVMGA AYFICGVIPA LFIKEKQYDP QQS          413

MucK_IP243 (SEQ ID NO: 6)
MYSNNQRSRI GSHTWKIAFL FAFLALLVDG ADLLLLSYSL NSIKAEFNLS TVEAGMLGSF    60
TLAGMAIGGI FGGWACDRFG RVRIVVISIL TFSILTCGLG LTQSFIQFGV LRFFASLGLG   120
SLYIACNTLM AEYVPTKYRT TVLGTLQAGW TVGYIVATLL AGWLIPDHGW RVLFYVAIIP   180
VLMAVLMHFF VPEPAAWQQS RLAPSKQTET VKTSAFKLIF QDKRNRNMFI LWALTAGFLQ   240
FGYYGVNNWM PSYLESELGM KFKEMTAYMV GTYTAMILGK ILAGFMADKL GRRFTYAFGA   300
IGTAIFLPLI VFYNSPDNIL YLLVIFGFLY GIPYGVNATY MIESFPTAIR GTAIGGAYNV   360
GRLGAAIAPA TIGFLASGGS IGLGFVVMGA AYFICGVIPA LFIKEKQYDP QQS          413

MucK_IP246 (SEQ ID NO: 8)
MYSNNQRSRI GSHTWKIAFL FAFLALLVDG ADLMLLSYSL NSIKAEFNLS TVEAGMLGSF    60
TLAGMAIGGI FGGWACDRFG RVRIVVISIL TFSILTCGLG LTQSFIQFGV LRFFASLGLG   120
SLYIACNTLM AECVPTKYRT TVLGTLQAGW TVGYIVATLL AGWLIPDHGW RVLFYVAIIP   180
VLMAVLMHFF VPEPAAWQQS RLAPSKQTET VKTSAFKLIF QDKRNRNMFI LWALTAGFLQ   240
FGYYGVNNWM PSYLESELGM KFKEMTAYMV GTYTAMILGK ILAGFMADKL GRRFTYAFGA   300
IGTAIFLPLI VFYNSPDNIL YLLVIFGFLY GIPYGVNATY MTESFPTAIR GTAIGGAYNV   360
GRLGAAIAPA TIGFLASGGS IGLGFVVMGA AYFICGVIPA LFIKEKQYDP QQS          413

TpaK_RHA1 (SEQ ID NO: 9)
MSLAPSRVTL PDFIDSRPVS RYQYIVIALC GVVMFIDGFD TQSISYMAPH IAEEWGLSKQ    60
VLGPIFSAAL AGLMVGYLAL SPLSERFGHR RMILTSTVIF ALGTLAAAWS QNVTELMALR   120
FITGMGLGAA APSAIALTGE FSPKRLRATF VLVIYCGFSL GFVAAGLVSG WLIPILGWRS   180
VLVVGAVAPL LLLPALLRYL PDSLTSMINR GAEPNRIQAI FRKMDPALAV GPDITYEAEK   240
RTDGQRTALR SLFTRDRVLG TLLLWLVFVI NLGEFYALQS WLPSIMTSLY DMGTVVTATT   300
LTTVGGIAAA FVTGPCMDRL GAYVTLGTVY VVGFAFVALT GVAFTAPLWV LLTANFFAGV   360
CISGGQKSLI ALSAVFYPTP MRSTGVGWAL GVGRLGGIVG PIAVGAALGM GWSASAVFYA   420
MSVPMLVAGA AVFLLGRWVR SDNHPDRKSA ESHSLARK                           458

TpaK_DK17 (SEQ ID NO: 10)
MSLAPSRVTL PDFIDSRPVS RYQYIVIALC GVVMFIDGFD TQSISYMAPH IAEEWGLSKQ    60
VLGPIFSAAL AGLMVGYLAL SPLSERFGHR RMILTSTVIF ALGTLAAAWS QNVTELMALR   120
FITGMGLGAA APSAIALTGE FSPKRLRATF VLVIYCGFSL GFVAAGLVSG WLIPILGWRS   180
VLVVGAVAPL LLLPALLRYL PDSLTSMINR GAEPNRIQAI FRKMDPALAV GPDITYEAEK   240
RTDGQRTALR SLFTRDRVLG TLLLWLVFVI NLGEFYALQS WLPSIMTSLD YNMGTVVTAT   300
TLTTVGGIAA AFVTGPCMDR LGAYVTLGTV YVVGFAFVAL TGVAFTAPLW VLLTANFFAG   360
VCISGGQKSL IALSAVFYPT PMRSTGVGWA LGVGRLGGIV GPIAVGAALG MGWSASAVFY   420
AMSVPMLVAG AAVFLLGRWV RSDNHPDRKS AESHSLARK                          459
```

Figure 18C

TpaK_LB400 (SEQ ID NO: 11)
```
MASPLIDVVE VIERQKVGIG QSKDWHLPRE VLGSIFSAAL VGLMVGYLAI APLSARFGHK    60
RMMLASSVLF ALFTLLTLFA TNVTELIGLR FLTGIGLGAA APSAVALTCE FAPKRLRATF   120
VLLVYCGFSL GFVVAGLTAG ALMPAFGWKS LMLVGALAPI ALTVPLAWLL PESLVVLQRR   180
PNGDERMRAV LLGFFPRLDV PVGSRFRLED QGEARASVTA LVRGRTSAGT LLLWLIFFLN   240
LAEFYFMQSW LPTMLTGLQY SPATVVWVTA LPTIAGVLSA VPLGLAMDRV GPYVTLTVMY   300
LAGCVFMWLV GGAFSGSVAW LMVMVFCAGF CISGGQKSVI ALAAVYYPLN LRSTGVWAL    360
GIGRLGGIAG PLSAGMLYSA HWTPAEIFRF SAWPVLIAGL AVFVMGRIYG SRPVAVEVST   420
PH                                                                 422
```

MucK_IP255 (SEQ ID NO: 12)
```
MYSNNQRSRI GSHTWKIAFL FAFLALLVDG ADLMLLSYSL NSIKAEFNLS TVEAGMLGSF    60
TLAGMAIGGI FGGWACDRFG RVRIVVISIL TFSILTCGLG LTQSFIQFGV LRFFASLGLG   120
SLYIACNTLM AEYVPTKYRT TVLGTLQAGC TVGYIVATLL AGWLIPDHGW RVLFYVAIIP   180
VLMAVLMHFF VPEPAAWQQS RLAPSKQTET VKTSAFKLIF QDKRNRNMFI LWALTAGFLQ   240
FGYYGVNNWM PSYLESELGM KFKEMTAYMV GTYTAMILGK ILAGFMADKL GRRFTYAFGA   300
IGTAIFLPLI VFYNSPDNIL YLLVIFGFLY GIPYGVNATY MTESFPTAIR GTAIGGAYNV   360
GRLGAAIAPA TIGFLASGGS IGLGFVVMGA AYFICGVIPA LFTKEKQYDP QQS          413
```

GudP_wt (SEQ ID NO: 13)
```
MDNLQTSAVS ISKVRVTHNK TRYYILAMIF LVTALNYGDR ATISMAATPM SQELGLTSVT    60
MGYIFSAFGW AYVIGQVPGG WLLDKFGARK VYFWSILLWS IFTVLLGFVD IFGSIPLIIA   120
SLFILRFLVG LSESPAFPGN SQIVAAWFPT KERGTAAASF NSAQYFATVI FAPFMGWLVT   180
HIHWQSVFWI MGAIGIVIAF IWLKVIYSPE KHPRINKEEL TYLQGNGAIT SMGENKSKTL   240
DQKNKMSWSN VKKLLSSRML LGIFIAQYCI TCLTYFFLTW FPVYLVKERH MTILQAGFAA   300
VLPALCGFIG GILGGIISDR LIRMNKSLSF SRKFPIVLGM LLSTSIIVCN YVDSQTAIVF   360
FMSLAFFGKG FGALGWAVMS DVAPKEMIGL SGGLFNTFGN TAGIIIPIAI GYIVASTGSF   420
NGALVFVGIH AIIAILCYLF VVGKIERFEL KKVI                              454
```

GudP_IP247 (SEQ ID NO: 14)
```
MDNLQTSAVS ISKVRVTHNK TRYYILAMIF LVTALNYGDR ATISMAATPM SQELGLTSVT    60
MGYIFSAFGW AYVIGQVPGG WLLDKFGARK VYFWSILLWS IFTVLLGFVD IFGSIPLIIA   120
SLFILRFLVG LSESPAFPGN SQIVAAWFPT KERGTAAASF NSAQYFATVI FAPFMGWLVT   180
HIHWQSVFWI MGAIGIVIAF IWLKVIYSPE KHPRINKEEL TYLQGNGAIT SMGENKSKTL   240
DQKNKMSWSN VKKLLSSRML LGIFIAQYCI TCLTYFFLTW FPVYLVKECH MTILQAGFAA   300
VLPALCGFIG GILGGIISDR LIRMNKSLSF SRKFPIVLGM LLSTSIIVCN YVDSQTAIVF   360
FMSLAFFGKG FGALGWAVMS DVAPKEMIGL SGGLFNTFGN TAGIIIPIAI GYIVASTGSF   420
NGALVFVGIH AIIAILCYLF VVGKIERFEL KKVI                              454
```

GudP_IP250 (SEQ ID NO: 15)
```
MDNLQTSAVS ISKVRVTHNK TRYYILAMIF LVTALNYGDR ATISMAATPM SQELGLTSVT    60
MGYIFSAFGW AYVIGQVPGG WLLDKFGARK VYFWSILLWS IFTVLLGFVD IFGSIPLIIA   120
SLFILRFLVG LSESPAFPGN SQIVAAWFPT KERGTAAASF NSAQYFATVI FAPFMGWLVT   180
HIHWQSVFWI MGAIGIVIAF IWLKVIYSPE KHPRINKEEL TYLQGNGAIT SMGENKSKTL   240
DQKNKMSWSN VKKLLSSRML LGIFIAQYCI TCLTYFFLTW FPVYLVKERH MTILQAGFAA   300
VLPALCGFIG GILGGIISDR LIRMNKSLSF SRKFPIVLGM LLSTSIIVCN YVDSQTAIVF   360
FMSLAFFGKG FGALGWAVMS DVAPKEMIGL SGGLFNTFGN TAGIIIPIAI GYIVASTGSF   420
NGALVFVGIH AIIAILCYLF VVGKIELFEL KKVI                              454
```

Figure 18D

MUTANT TRANSPORTERS FOR BACTERIAL UPTAKE OF TEREPHTHALIC ACID

CROSS-REFERENCE TO RELATED APPLICATIONS

This application claims priority from U.S. Provisional Patent Application No. 63/077,173 filed on Sep. 11, 2020, the contents of which are incorporated herein by reference in their entirety.

CONTRACTUAL ORIGIN

This invention was made with government support under Contract No. DE-AC36-08GO28308 awarded by the Department of Energy. The government has certain rights in this invention.

REFERENCE TO SEQUENCE LISTING

This application contains a Sequence Listing submitted as an electronic text file entitled "NREL 20-53_ST25_V2.txt" having a size in bytes of 82 kb and created on Dec. 19, 2023. Pursuant to 37 CFR § 1.52(e)(5), the information contained in the above electronic file is hereby incorporated by reference in its entirety.

DEPOSIT OF MICROORGANISMS UNDER THE BUDAPEST TREATY

During the pendency of this application, access to the invention will be afforded to the Commission upon request. Upon granting of the patent the strain will be available to the public under the conditions specified in 37 CFR 1.808. The deposit will be maintained in a public repository for a period of 30 years or 5 years after the last request or for the effective life of the patent, whichever is longer. The deposit will be replaced if it should ever become unavailable.

BACKGROUND

As a dicarboxylic acid, terephthalic acid (TPA) cannot freely diffuse through the cell membrane. Therefore, among other things, efficient transport of TPA into the cell is important in order to engineer bacteria for the degradation of this product, and its potential biological conversion into value-added products. Furthermore, while there are enzymes known to be capable of breaking down the recalcitrant PET polymer into its constituents, TPA and ethylene glycol, these perform poorly. Thus, there remains a need for developing engineered microorganisms and/or enzymes having, among other things, improved TPA-transport capabilities.

SUMMARY

An aspect of the present disclosure is a non-naturally occurring microorganism that includes a gene encoding a MucK transporter protein, where the microorganism is capable of catabolizing terephthalic acid (TPA). In some embodiments of the present disclosure, the gene encoding the MucK transporter protein may contain at least one mutation, relative to a reference gene encoding a reference MucK transporter protein.

In some embodiments of the present disclosure, the reference MucK transporter protein may be at least 90% identical to SEQ ID NO: 2. In some embodiments of the present disclosure, the gene encoding the reference MucK transporter protein may be at least 90% identical to SEQ ID NO: 1. In some embodiments of the present disclosure, the mutation to the MucK transporter protein may include at least one point mutation. In some embodiments of the present disclosure, the point mutation may be present at an amino acid located at at least one of positions 34, 53, 133, 341, or 342 on SEQ ID NO: 2. In some embodiments of the present disclosure, the point mutation may include at least one of M34L, M34I, Y133C, T342I, or E53G on SEQ ID NO: 2.

In some embodiments of the present disclosure, the non-naturally occurring microorganism may further include a deletion of an endogenous gene encoding a MucK transporter protein. In some embodiments of the present disclosure, the non-naturally occurring microorganism may be capable of growing on TPA. In some embodiments of the present disclosure, the non-naturally occurring microorganism may be characterized by a TPA consumption rate between greater than zero g TPA/L/hr and about 0.2 g/L/hr. In some embodiments of the present disclosure, the non-naturally occurring microorganism the microorganism may be grown in a liquid media at a temperature between about 25° C. and about 35° C. In some embodiments of the present disclosure, the liquid media may be maintained at pH between about 6 and about 7.

In some embodiments of the present disclosure, the non-naturally occurring microorganism comprises at least one of a bacterium, a yeast, or a fungus. In some embodiments of the present disclosure, the non-naturally occurring microorganism may be a bacterium. In some embodiments of the present disclosure, the bacterium may include a strain from at least one of *A. baylyi, P. putida, P. fluorescens*, and/or *P. stutzeri*. In some embodiments of the present disclosure, the bacterium is *A. baylyi*. In some embodiments of the present disclosure, the bacterium is *A. baylyi* ADP1. In some embodiments of the present disclosure, the non-naturally occurring microorganism may further include the deletion of an endogenous gene encoding a transcriptional regulator. In some embodiments of the present disclosure, the transcriptional regulator may be a DcaS transcriptional regulator.

BRIEF DESCRIPTION OF THE DRAWINGS

Some embodiments are illustrated in referenced figures of the drawings. It is intended that the embodiments and figures disclosed herein are to be considered illustrative rather than limiting.

Figure 3:
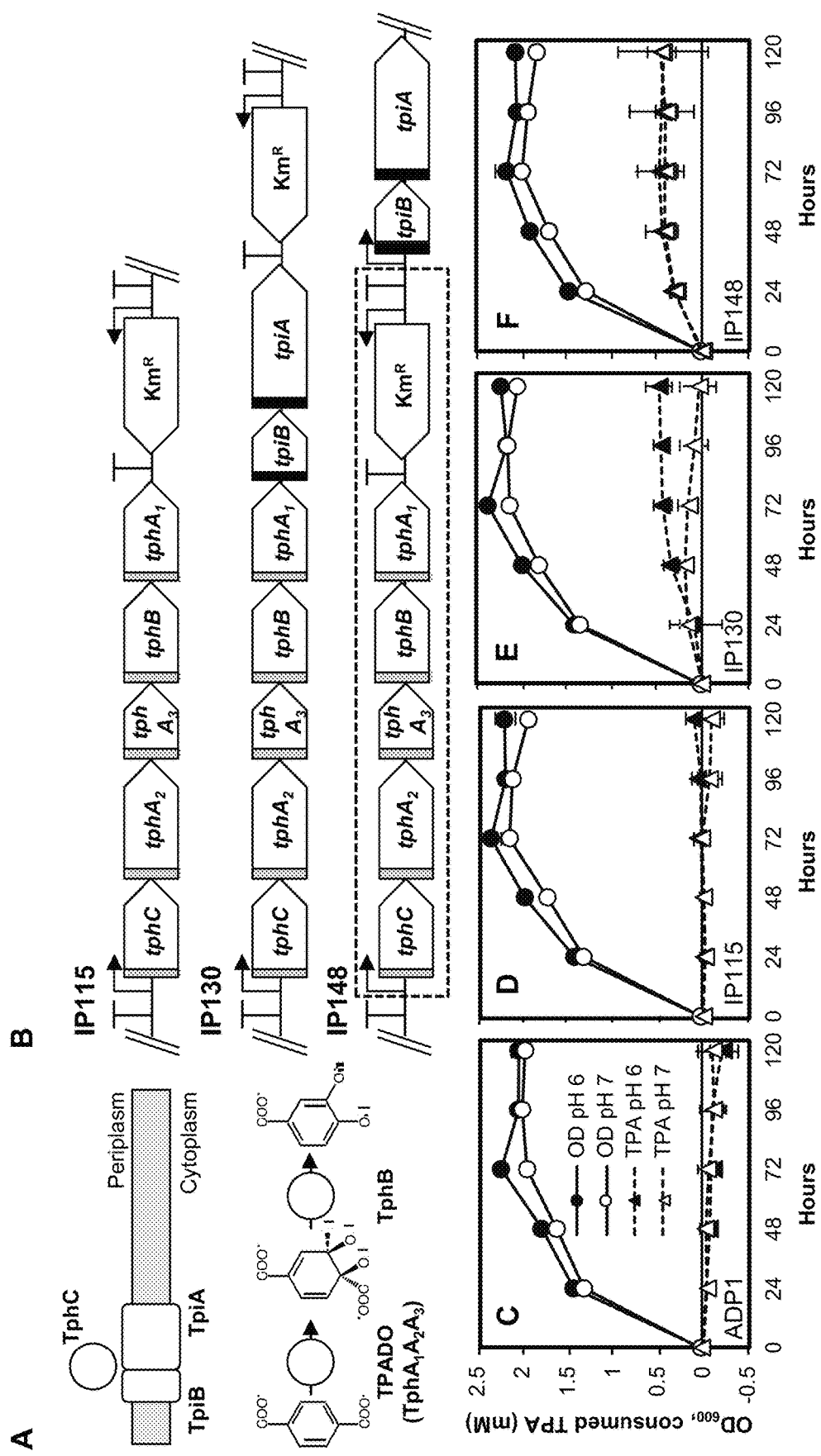

FIG. 3 illustrates TPA transport and catabolism, genetic organization, and TPA turnover in *A. baylyi* strains with a single copy of heterologous genes integrated in the chromosome, according to some embodiments of the present disclosure. (A) TPA transport and catabolic proteins from *Comamonas* sp. E6. (B) Schematic representation of the synthetic tph:tpi operons integrated in the chromosome of ADP1, downstream of pobA. Catabolic genes are tphA genes encoding TPAD or tphB encoding dihydrodiol dehydrogenase. Transport genes are tphC encoding periplasmic SBP or tpiBA encoding transmembrane proteins). The kanamycin resistance gene is $Km^R$. Synthetic RBS sequences are shown in gray (high predicted TIR) or white (low predicted TIR). Black arrows indicate transcription initiation and direction. The "T"s indicate transcription terminators (rrnB T1 upstream tphC and prophage T4 transcription/translation termination signal flanking the $Km^R$ gene). The EASy amplicon is bound by a dotted line for strain IP148. (C—F) Growth ($OD_{600}$) and consumed TPA (mM) for (C) wild-type ADP1, (D) IP115, (E) IP130, and (F) IP148, grown in MMP+5 mM TPA at pH 6 and pH 7. Pyruvate (20 mM) was supplemented every 24 h to support growth and completely consumed in all cases (120 mM in total). Consumed TPA values shown are corrected with respect to non-inoculated flasks to account for the increased TPA concentrations caused by evaporation. Error bars indicate the standard deviation for three replicates.

Figure 4:
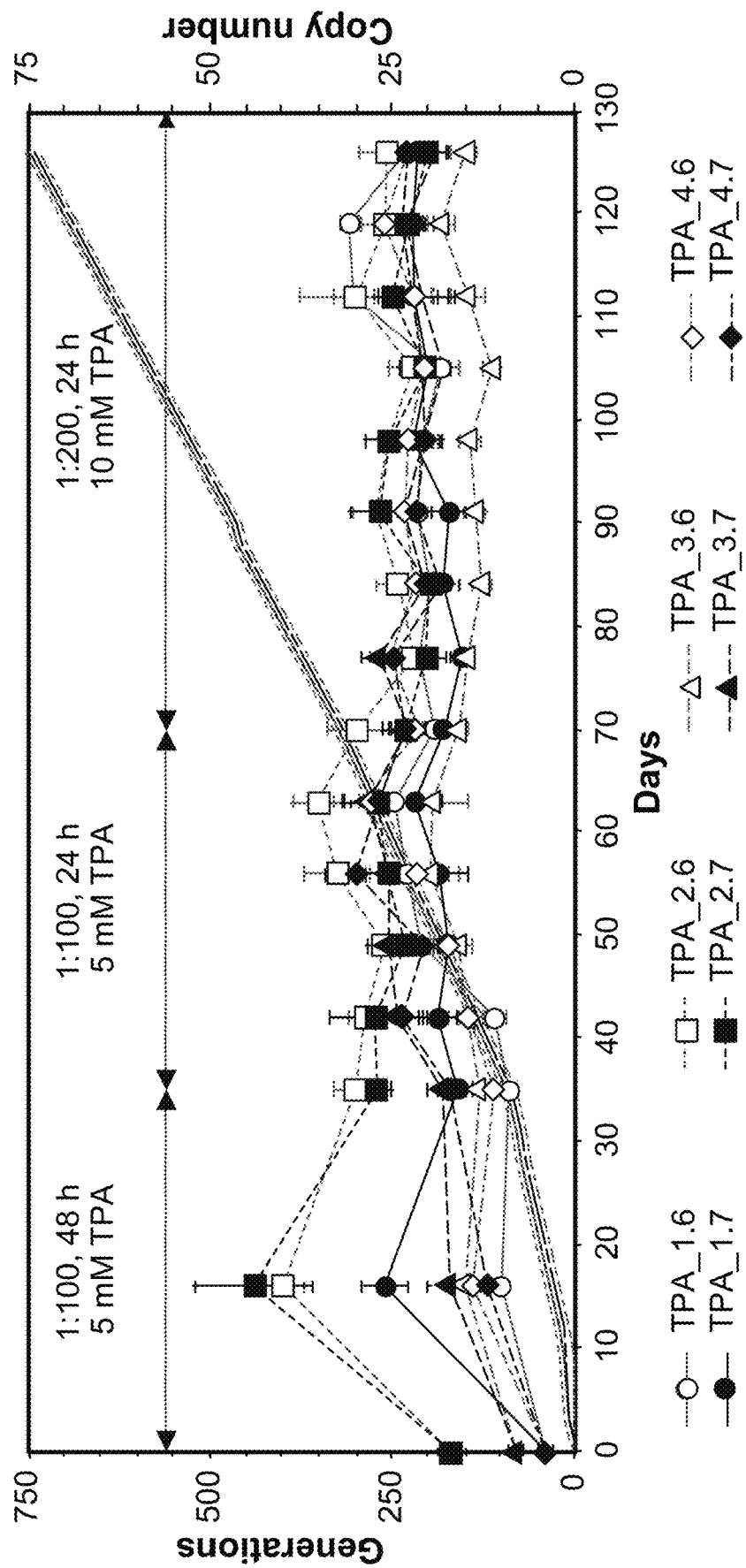

FIG. 4 illustrates ALE of IP148-derived amplification mutants on TPA), according to some embodiments of the present disclosure. Symbols indicate changes in amplicon copy number over time (values indicated on the right-side axis). Error bars indicate the standard deviation for four technical replicates. Cumulative generations are shown as dashed lines (values indicated on the left-side axis). Changes in serial transfer conditions (culture dilution, frequency, and TPA concentration) during ALE are indicated.

Figure 5:
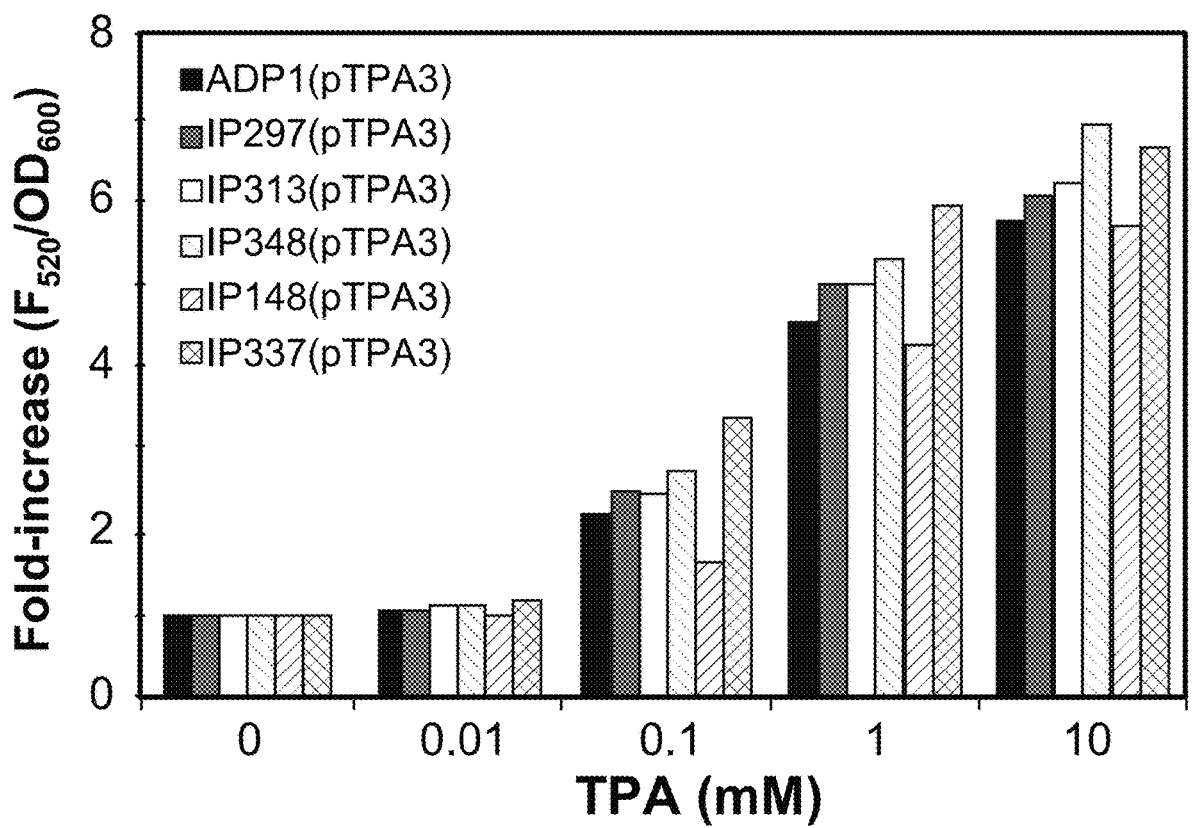

FIG. 5 illustrates the increase of normalized fluorescence at 520 nm ($F_{520}/OD_{600}$, as measured in a plate-reader; 50 gain, 8-h timepoint) for *A. baylyi* strains carrying pTPA3 and grown in MMP with increasing TPA concentrations), according to some embodiments of the present disclosure. Error bars indicate the standard deviation for three biological replicates.

FIG. 6 illustrates a sequence of mutated tpiA found in IP148 and Tpa+ amplification isolates TPA_1 to TPA_4, according to some embodiments of the present disclosure. Mutation is shown in gray box. The encoded amino acid sequence for peptides TpiA(W366*) and TpiA(Δ1-370) are respectively indicated with a single or double underline.

Figure 7:
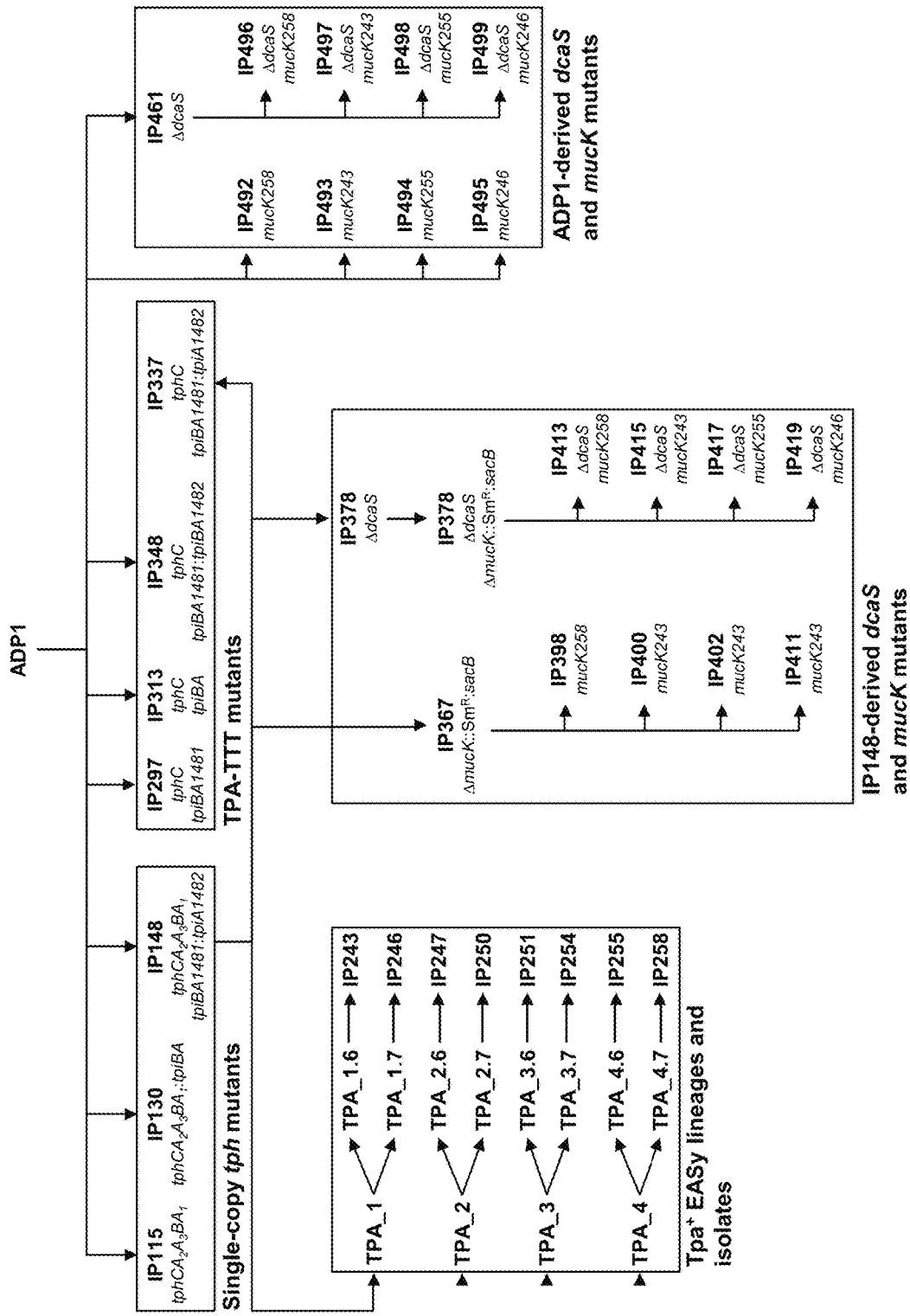

FIG. 7 illustrates a dendrogram of *A. baylyi* strains and isolates used in this work, according to some embodiments of the present disclosure. Mutations introduced during strain construction relevant to TPA catabolism and transport are indicated.

Figure 8A:
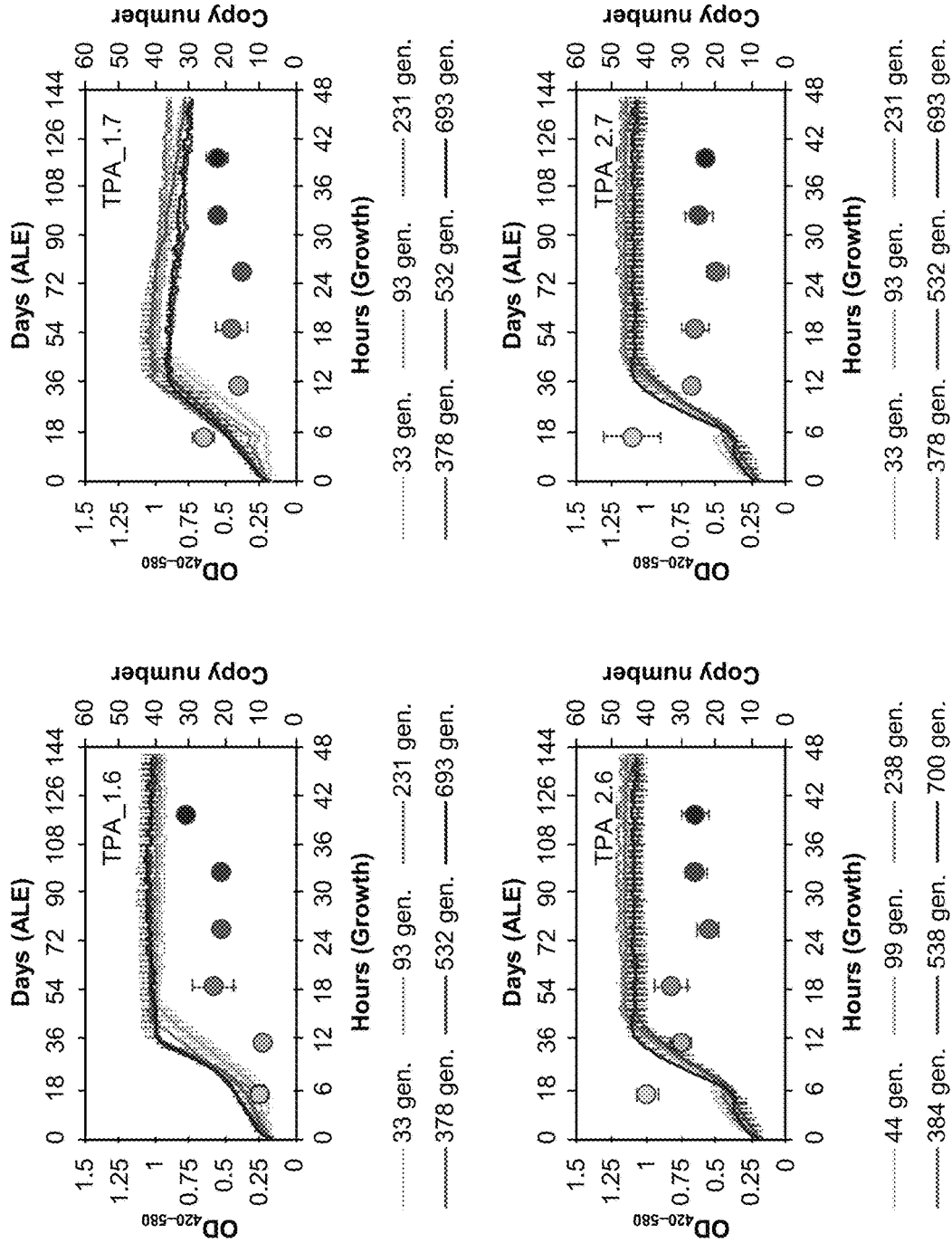
Figure 8B:
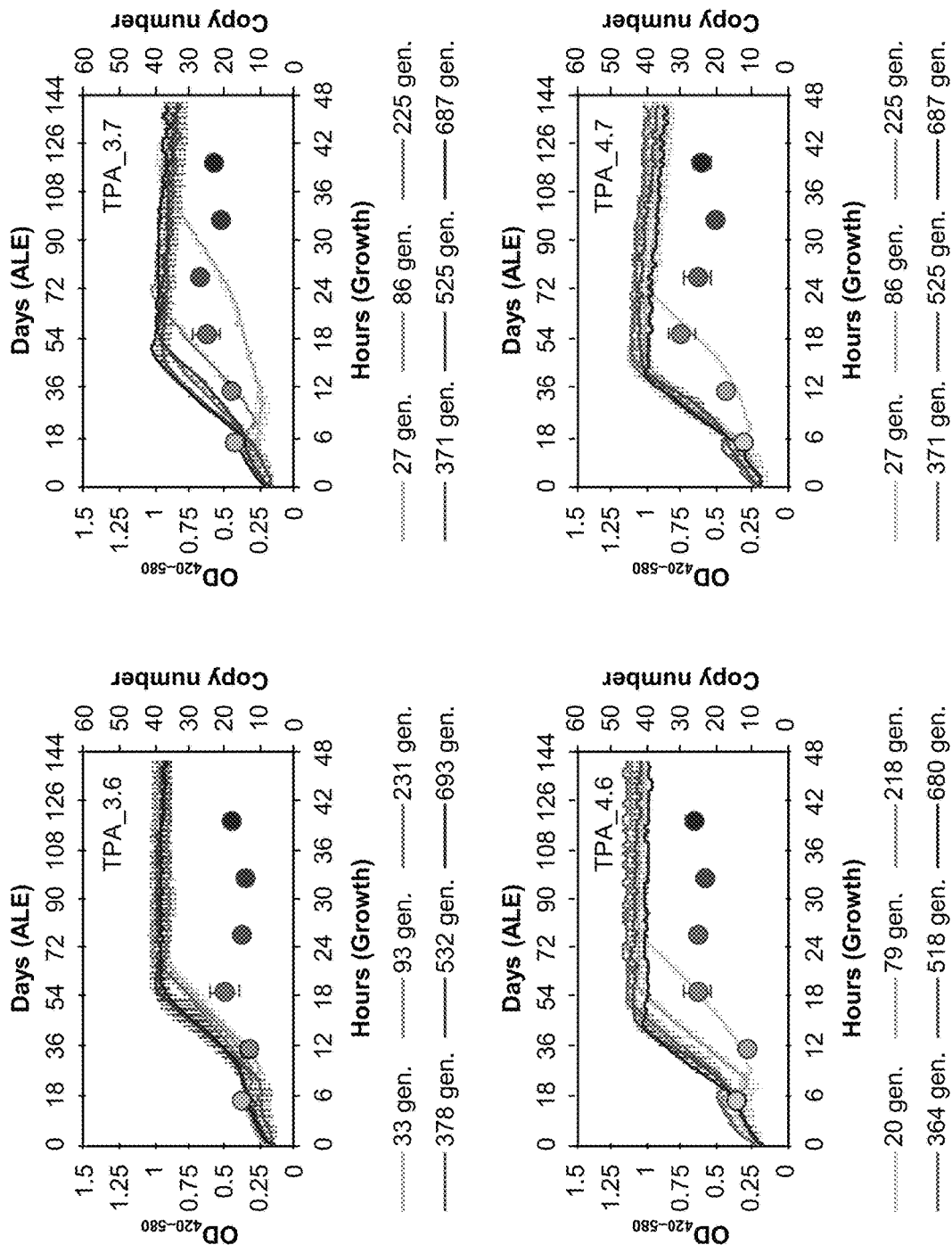

FIGS. 8A and 8B illustrate changes in growth rates in 10 mM TPA for the different EASy lineages throughout ALE), according to some embodiments of the present disclosure. Average $OD_{420-580}$ (left axis) over time (hours, lower axis) is shown as lines (error bars indicate standard deviation for three individual wells). Amplicon copy number (right axis) for a given ALE population (days, top axis) is shown as circles (error bars indicate standard deviation for four technical replicates).

Figure 9:
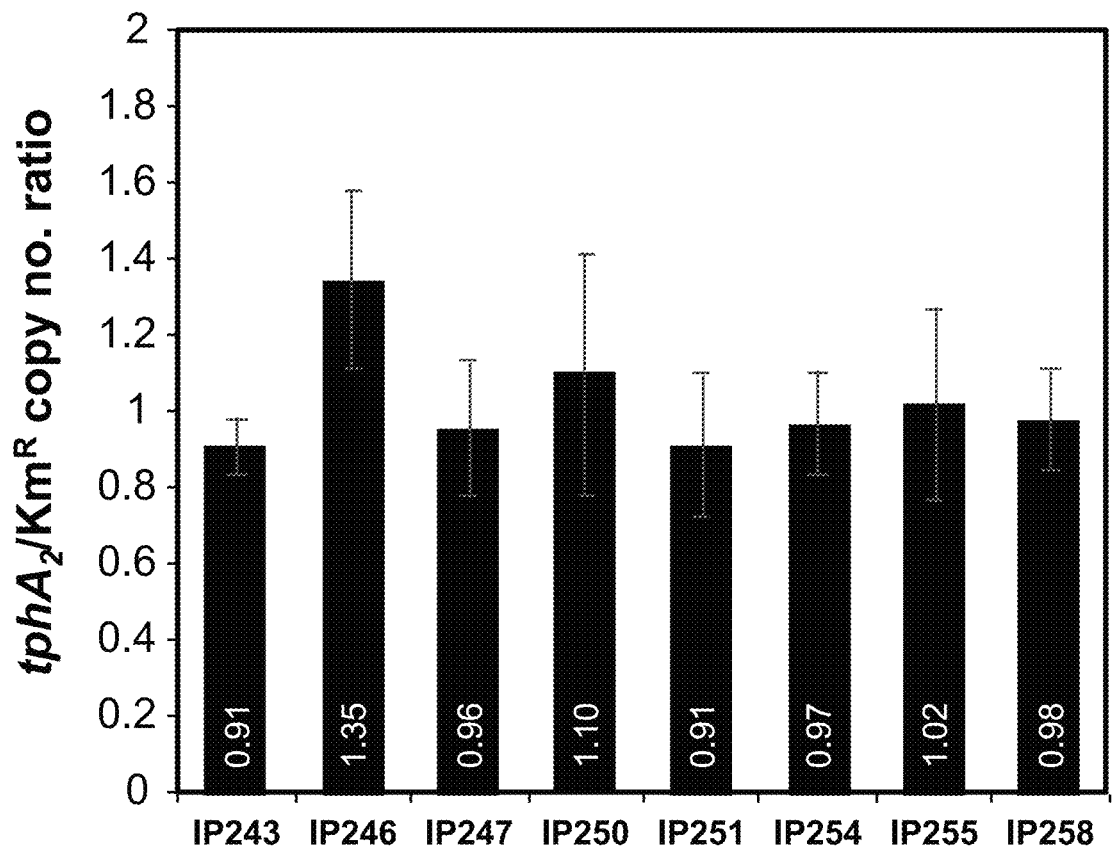

FIG. 9 illustrates the copy-number ratio of $tphA_2$ over the $Km^R$ gene for evolved Tpa+ isolates determined by qPCR), according to some embodiments of the present disclosure. Error bars indicate standard deviation for four technical replicates.

Figure 10:
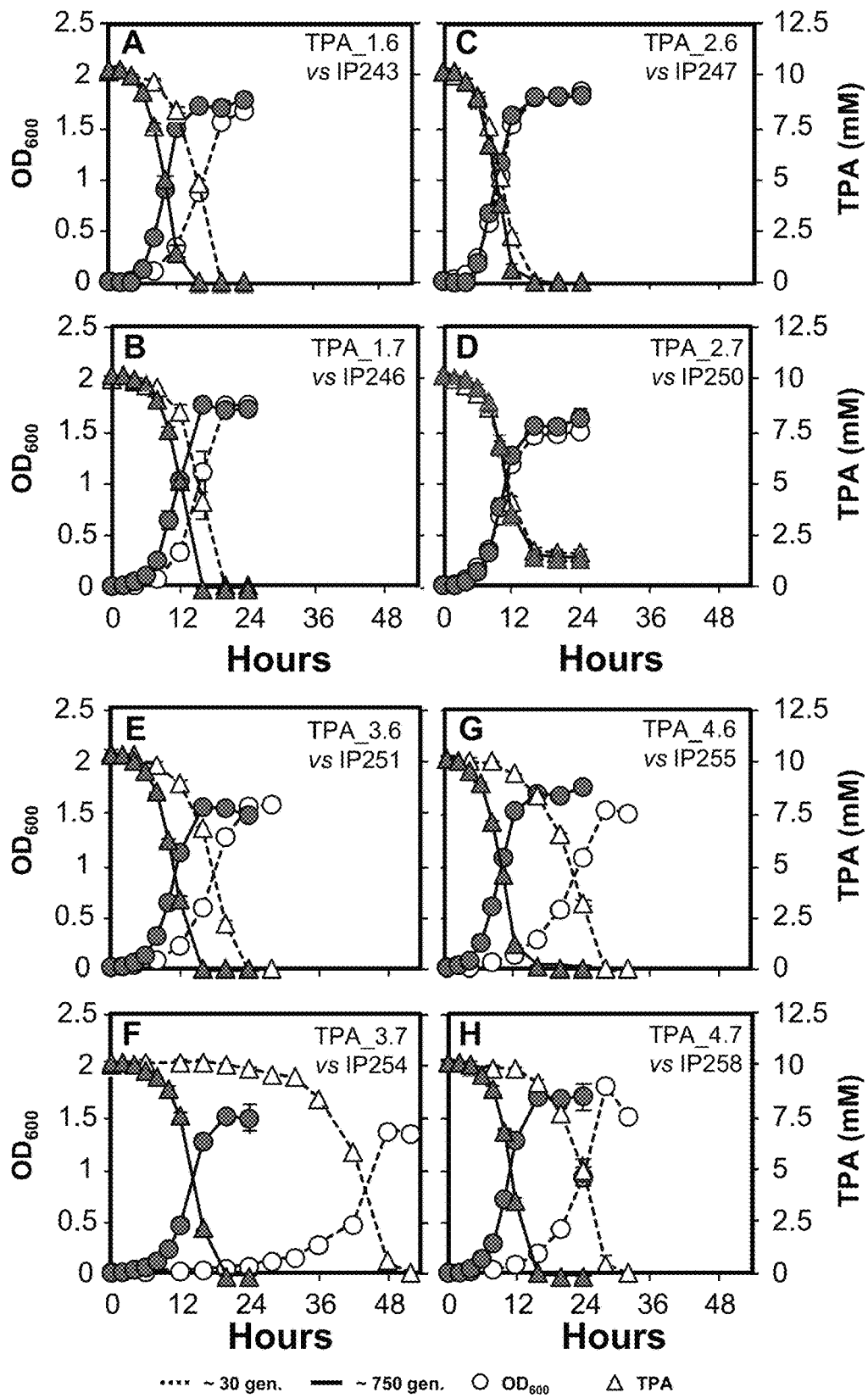

FIG. 10 illustrates shake-flask cultures with TPA as a sole carbon and energy source), according to some embodiments of the present disclosure. Growth ($OD_{600}$) and TPA concentration (mM) over time are plotted for cultures of EASy lineages after ~30 generations and isolates after ~750 generations. Cultures from top (A, C, E, G) and bottom (B, D, F, H) rows were respectively grown at pH 6 and pH 7. Error bars indicate the standard deviation from three biological replicates.

Figure 11:
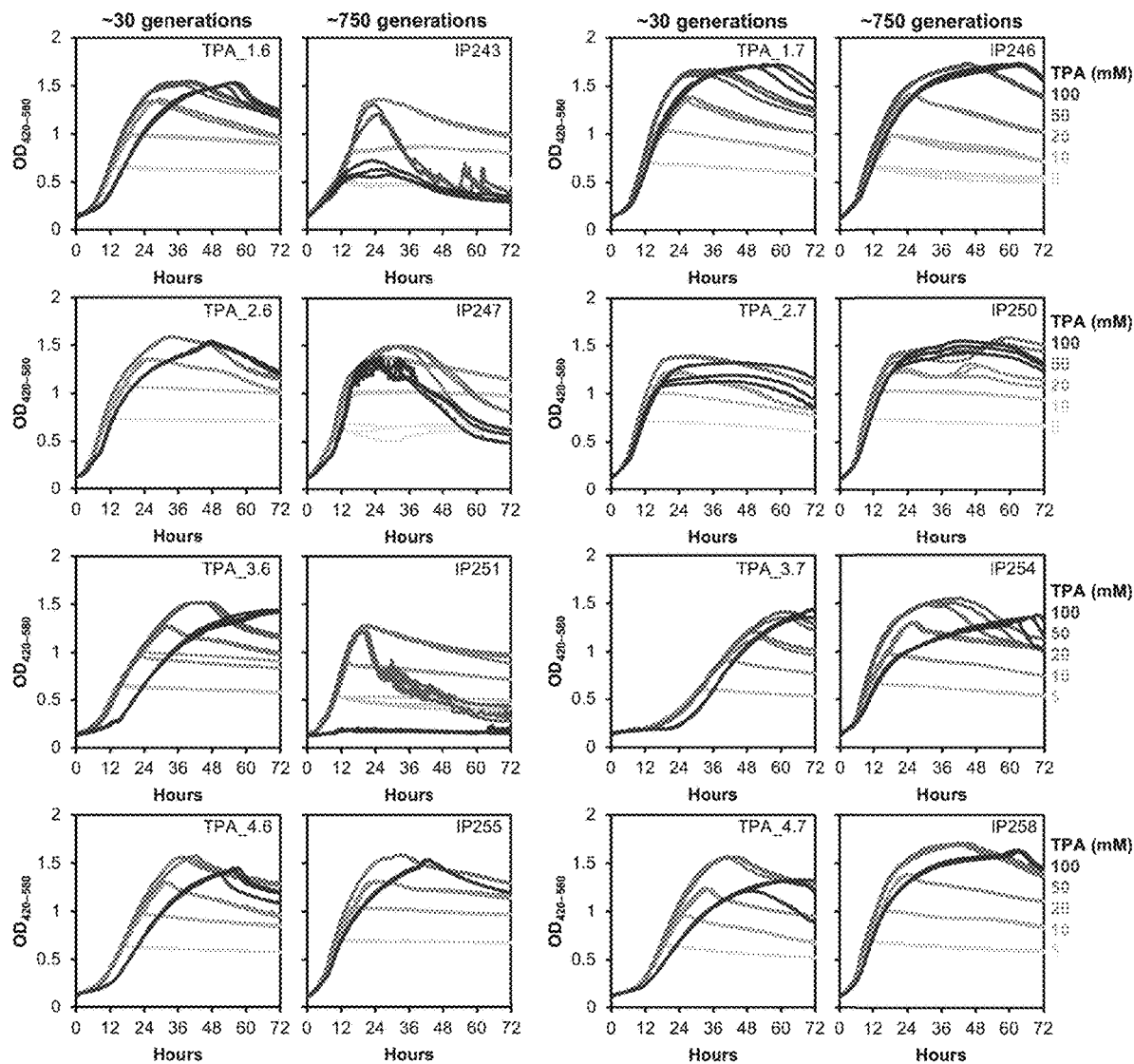

FIG. 11 illustrates the growth in increasing TPA concentrations of EASy lineages after ~30 generations and evolved isolates after ~750 generations), according to some embodiments of the present disclosure. Changes in $OD_{420-580}$ over time are shown for individual triplicates. TPA concentrations used (mM) are indicated on the right.

Figure 12:
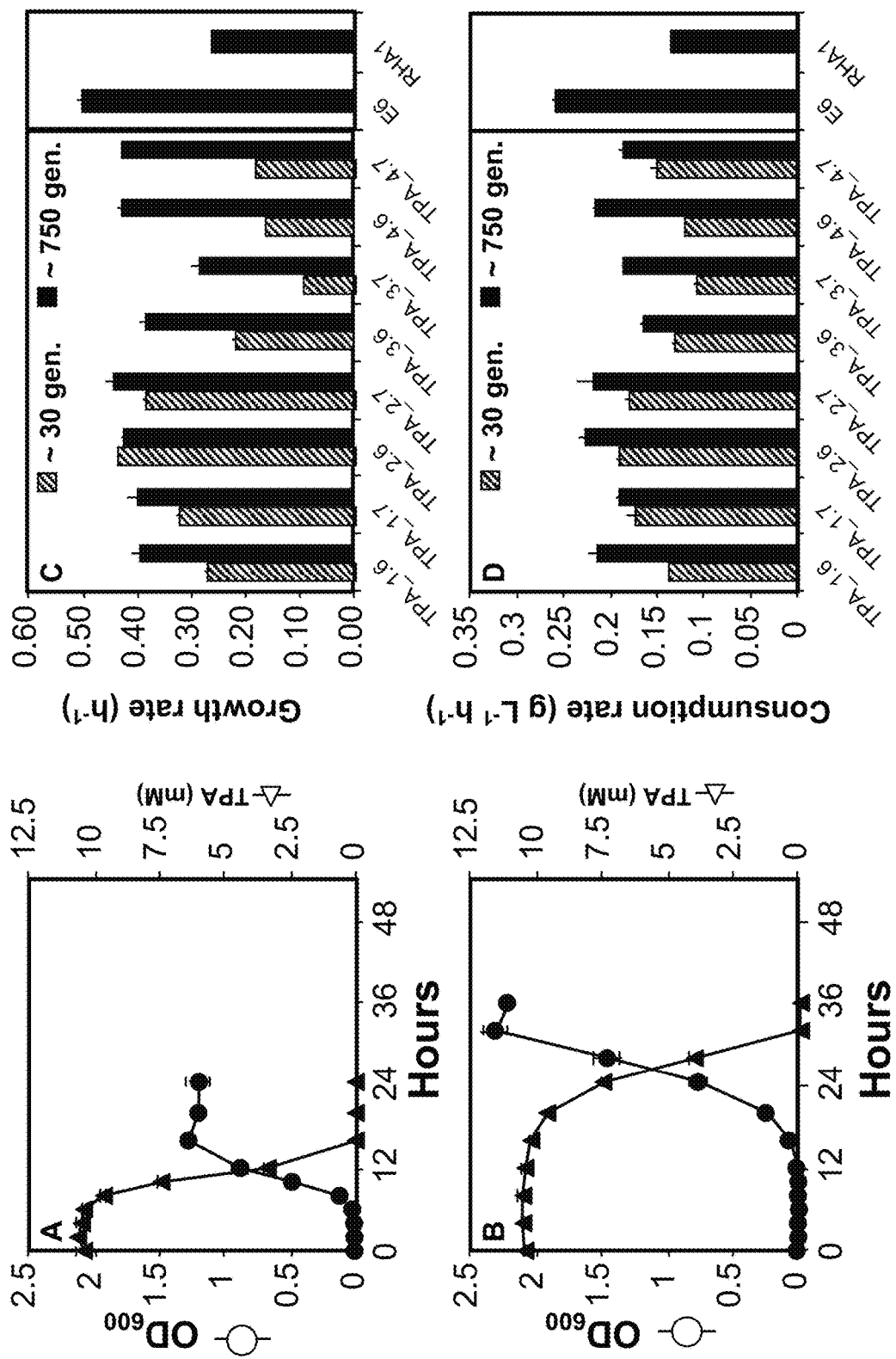

FIG. 12 illustrates a comparison of *A. baylyi* EASy lineages after ~30 generations and isolates after ~750 generations to native TPA-utilizing bacteria), according to some embodiments of the present disclosure. (A-B) Growth ($OD_{600}$) and TPA concentration (mM) over time for (A) *Comamonas* sp. E6 and (B) *R. jostii* RHA1 cultures grown at pH 7. (C) Growth rates ($h^{-1}$), calculated from $\ln(OD_{600})$ as a function of time. (D) TPA consumption rates (g/L/h) calculated from TPA concentration as a function of time in log growth phase. Error bars indicate the standard deviation from three biological replicates.

Figure 13:
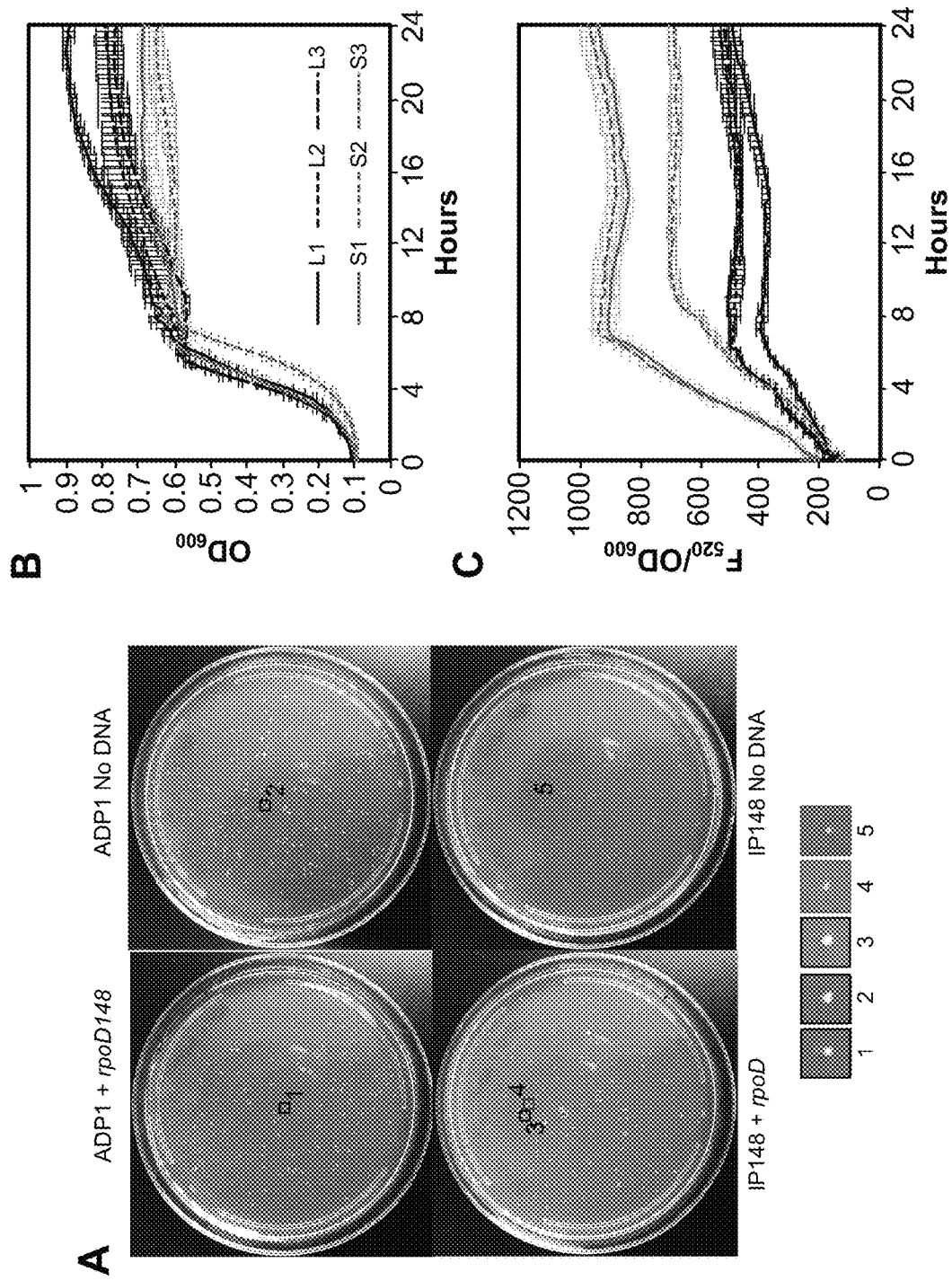

FIG. 13 illustrates an evaluation of RpoD(A87E)), according to some embodiments of the present disclosure. (A) Agar plates from growth competition cultures showing colonies of different size. Amplified images (5×) of representative large (1-3) and small (4-5) colonies are shown. (B) Growth ($OD_{600}$) and (C) normalized fluorescence ($F_{520}/OD_{600}$) for individual clones from three large colonies (L1-L3) and three small colonies (S1-S3) from IP148+rpoD plate, transformed with pTPA3. Clones L1-L3 were confirmed to have acquired wild-type rpoD by sequencing, whereas S1-S3 retained rpoD148. Cells were grown in MMP without TPA. Average and standard deviation for triplicate wells are shown.

Figure 14A:
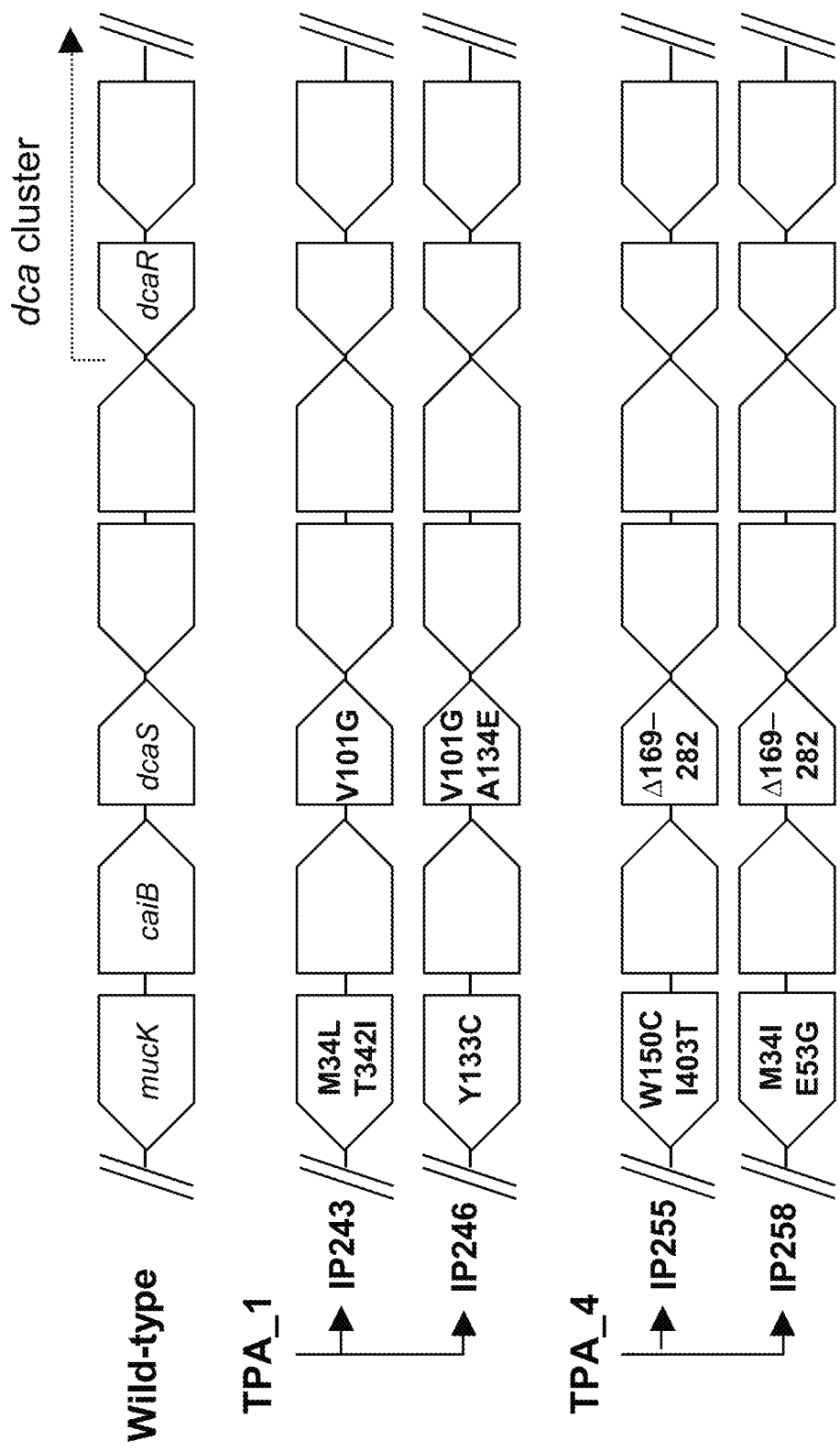

FIG. 14A illustrates a schematic representation of mucK and dcaS mutations found in evolved isolates, showing their genetic organization in the chromosome), according to some embodiments of the present disclosure. Predicted amino acid changes are shown in bold.

FIG. 14B (top) illustrates relative mucK expression levels ($2^{-\Delta\Delta Ct}$) for wild-type ADP1 and Δ dcaS mutant IP461), according to some embodiments of the present disclosure. Results are shown for three biological replicates, each measured with three technical replicates, and normalized to wild-type ADP1 grown on pyruvate. Error bars indicate the standard deviation. PYR: pyruvate; MUC: muconate; PCA: protocatechuate. FIG. 14B (bottom) illustrates the increase of normalized fluorescence at 520 nm ($F_{520}/OD_{600}$) for wild-type ADP1 and ΔdcaS mutant IP461, both transformed with pTPA3, after 8 hours of growth in MMP with increasing TPA concentrations, according to some embodiments of the present disclosure. Error bars indicate the standard deviation for biological triplicates.

Figure 14C:
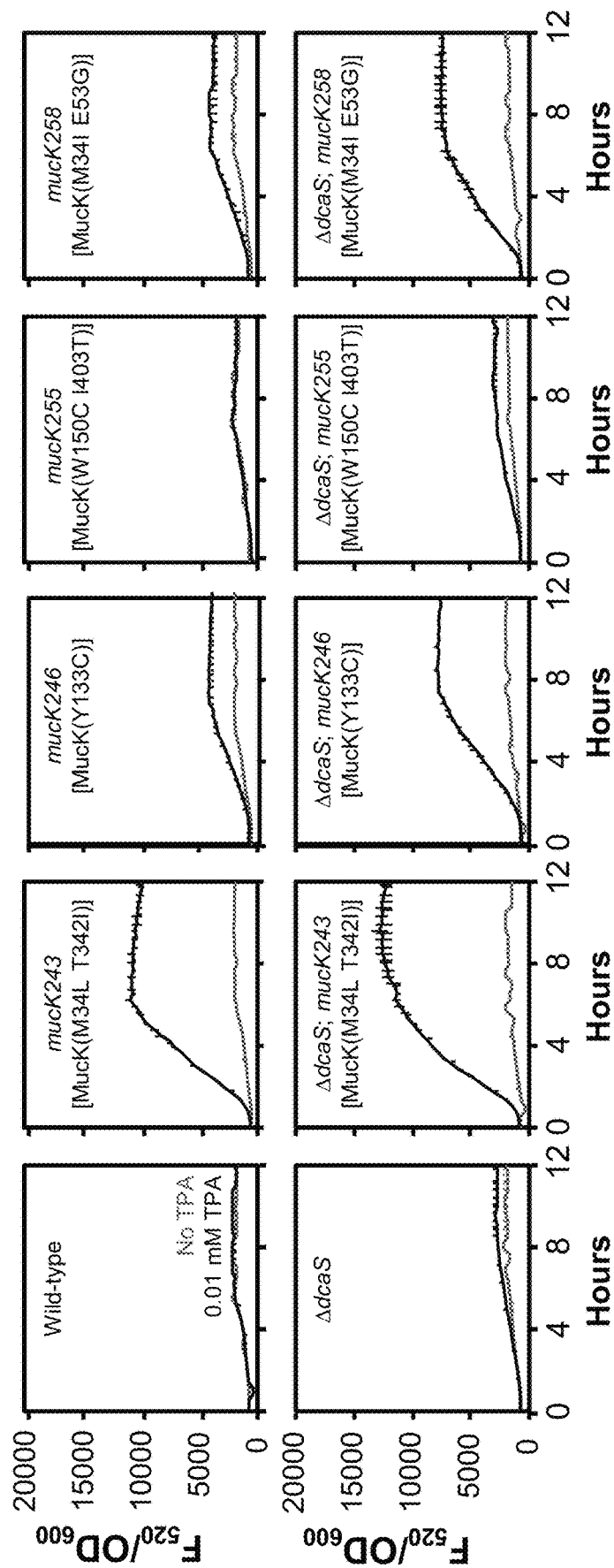

FIG. 14C illustrates the normalized fluorescence ($F_{520}/OD_{600}$) over time for mucK mutant strains in wild-type or ΔdcaS backgrounds, transformed with pTPA3, and grown in the absence (gray lines) or presence of 0.01 mM TPA (black lines), according to some embodiments of the present disclosure. MucK variants encoded by the different alleles are indicated in brackets. Average and standard deviation for biological triplicates are shown.

Figure 15:
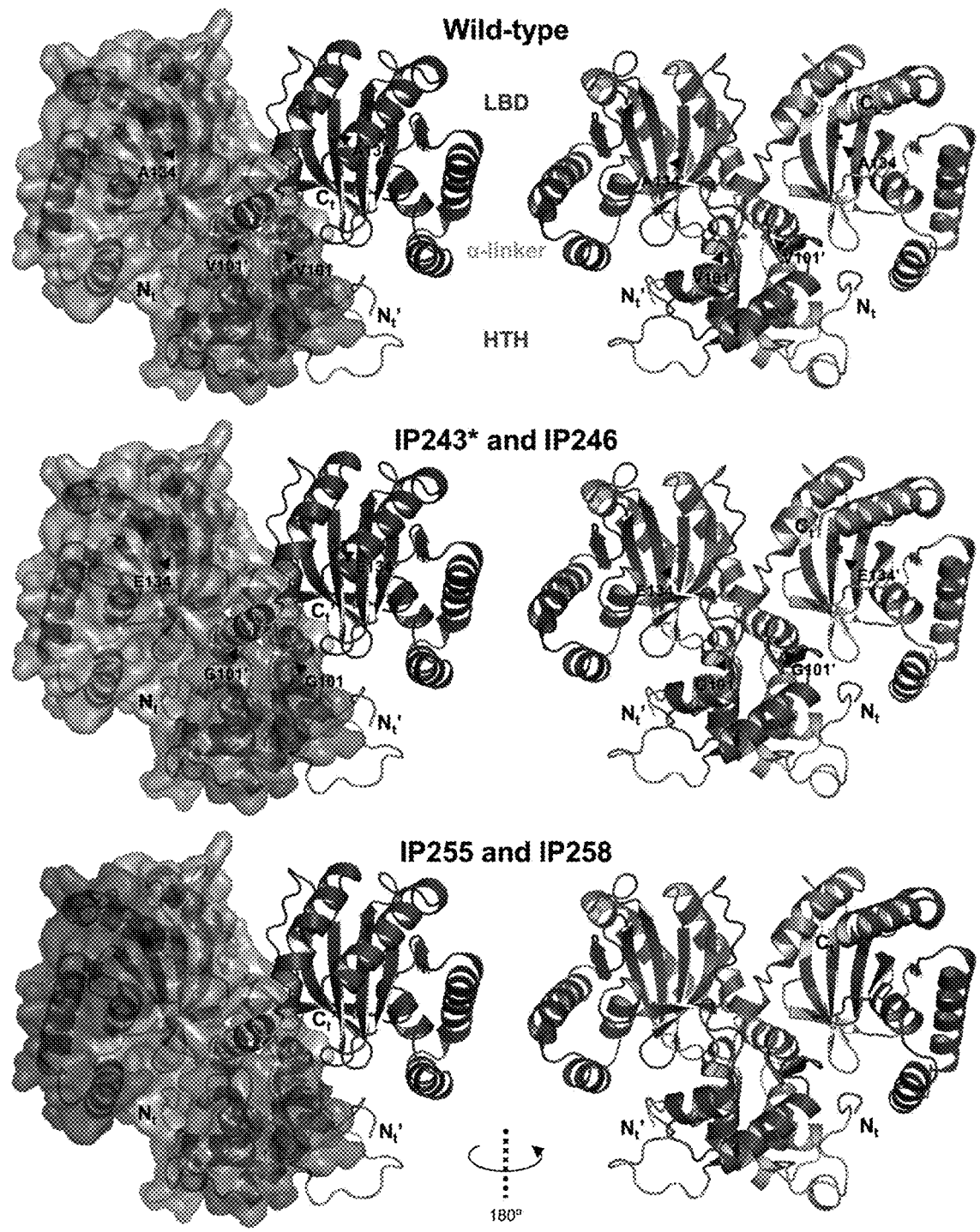

FIG. 15 illustrates three-dimensional (3D) structure models for dimers of DcaS variants selected during ALE. Models were built with SWISS-MODEL, using the crystal structure of BaaR from *Brucella abortus* as template (PDB 5WHM, 62% sequence identity).

Figure 16:
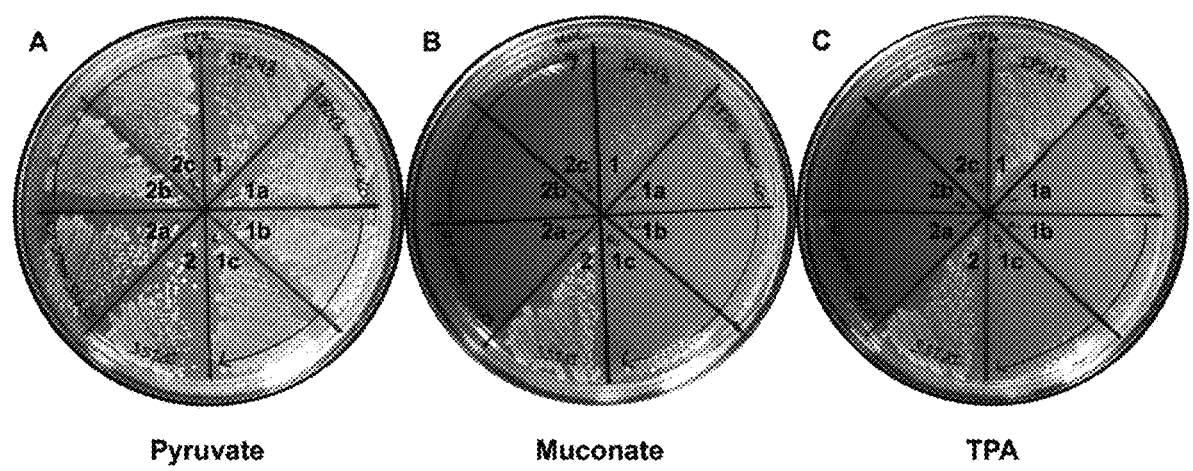

FIG. 16 illustrates the growth of three independent mucK knock-out mutants (1a-1c and 2a-2c) derived from evolved isolates IP243 (1) and IP255 (2) on minimal medium plates supplemented with (A) 20 mM pyruvate, (B) 5 mM muconate, and (C) 5 mM TPA, according to some embodiments of the present disclosure.

Figure 17:
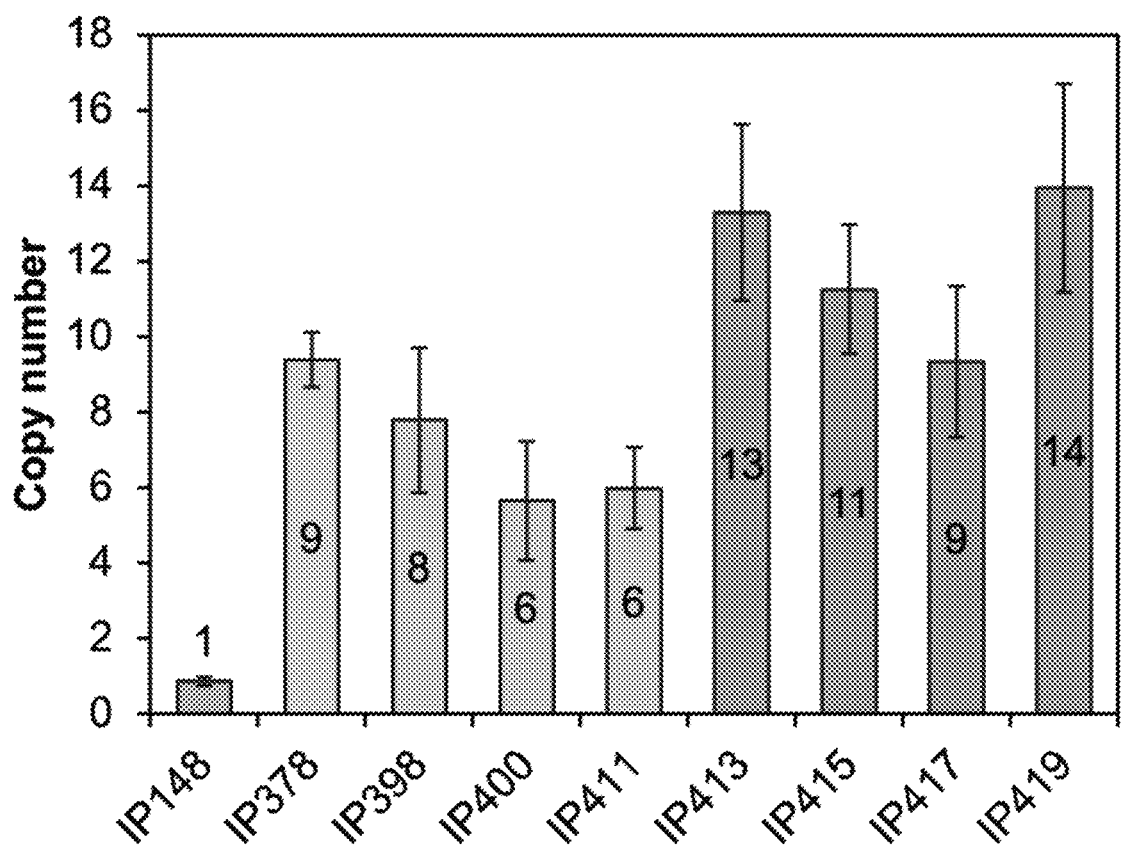

FIG. 17 illustrates tphA$_2$ gene copy number in dcaS and mucK IP148-derived mutants after spontaneous growth on minimal medium with 10 mM TPA as the sole carbon and energy source, according to some embodiments of the present disclosure. The parent strain IP148 was included as a control. IP378, ΔdcaS; IP398, mucK258; IP400, mucK243; IP411, mucK246; IP413, ΔdcaS mucK258; IP415, ΔdcaS mucK243; IP417, ΔdcaS mucK255; IP419, ΔdcaS mucK246. Average copy number and standard deviation are shown for four technical replicates.

FIGS. 18A-18D illustrate clustal Omega alignment of TpaK from *R. jostii* RHA1 (GenBank accession no. ABH00388), *Rhodococcus* sp. DK17 (GenBank accession no. AAR90191), and *P. xenovorans* LB400 (GenBank accession no. ABE33247) with MucK and GudP variants from *A. baylyi*. Replaced residues in MucK and GudP variants found in evolved Tpa+ isolates are in bold and underlined text.

DETAILED DESCRIPTION

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

A "vector" or "recombinant vector" is a nucleic acid molecule that is used as a tool for manipulating a nucleic acid sequence of choice or for introducing such a nucleic acid sequence into a host cell. A vector may be suitable for use in cloning, sequencing, or otherwise manipulating one or more nucleic acid sequences of choice, such as by expressing or delivering the nucleic acid sequence(s) of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated or conduced) into a host cell.

Vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell. The expression vectors may contain elements that allow for constitutive expression or inducible expression of the protein or proteins of interest. Numerous inducible and constitutive expression systems are known in the art.

Typically, an expression vector includes at least one nucleic acid molecule of interest operatively linked to one or more expression control sequences (e.g., transcription control sequences or translation control sequences). In one aspect, an expression vector may comprise a nucleic acid encoding a recombinant polypeptide, as described herein, operably linked to at least one regulatory sequence. It should be understood that the design of the expression vector may depend on such factors as the choice of the host cell to be transformed and/or the type of polypeptide to be expressed.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, yeast, and mammalian vectors, have been described for replication and/or expression in various host cells or cell-free systems, and may be used with the sequences described herein for simple cloning or protein expression.

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library) and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning or assembling into a vector using restriction enzymes.

Recombinant nucleic acids also include those that result from recombination events that occur through the natural mechanisms of cells but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

A nucleic acid molecule or polynucleotide can include a naturally occurring nucleic acid molecule that has been isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having enzyme activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional enzyme. For example, a fragment can comprise the minimum nucleotides required to encode a functional enzyme. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to a sequence represented herein. In other embodiments, the nucleic acids may be at least about 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein, or 80%, 81%, 82%, 83%, 84%, 85%, 86%, 87%, 88%, 89%, 90%, 91%, 92%, 93%, 94%, 95%, 96%, 97%, 98% or 99% identical to a sequences represented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Also disclosed herein are recombinant vectors, including expression vectors, containing nucleic acids encoding enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, assembling, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

The nucleic acids described herein may be used in methods for production of enzymes and enzyme cocktails through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell but can be used interchangeably with the term "transfection".

Non-limiting examples of suitable host cells include cells from microorganisms such as bacteria, yeast, fungi, and filamentous fungi. Exemplary microorganisms include, but are not limited to, bacteria such as *E. coli*; bacteria from the genera *Pseudomonas* (e.g., *P. putida* or *P. fluorescens*), *Bacillus* (e.g., *B. subtilis*, *B. megaterium* or *B. brevis*), *Caulobacter* (e.g., *C. crescentus*), *Lactoccocus* (e.g., *L. lactis*), *Streptomyces* (e.g., *S. coelicolor*), *Streptococcus* (e.g., *S. lividans*), and *Corynybacterium* (e.g., *C. glutamicum*); fungi from the genera *Trichoderma* (e.g., *T. reesei*, *T. viride*, *T. koningii*, or *T. harzianum*), *Penicillium* (e.g., *P. funiculosum*), *Humicola* (e.g., *H. insolens*), *Chrysosporium* (e.g., *C. lucknowense*), *Gliocladium*, *Aspergillus* (e.g., *A. niger*, *A. nidulans*, *A. awamori*, or *A. aculeatus*), *Fusarium*, *Neurospora*, *Hypocrea* (e.g., *H. jecorina*), and *Emericella*; yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, *miscanthus*, and trees such as hardwoods and softwoods are also contemplated herein as host cells.

Host cells can be transformed, transfected, or infected as appropriate by any suitable method including electroporation, calcium chloride-, lithium chloride-, lithium acetate/polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from bacteria or fungi by direct transformation, in which DNA is mixed with the cells and taken up without any additional manipulation, by conjugation, electroporation, or other means known in the art. Expression vectors may be expressed by bacteria or fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing bacteria or fungi, for example, are available from ATCC. Media may be supplemented with aromatic substrates like guaiacol, guaethol or anisole for dealkylation reactions.

The nucleic acid molecules described herein encode the enzymes with amino acid sequences such as those represented by the SEQ ID NOs presented herein. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequences presented herein or may include up to a certain integer number of amino acid alterations. Such protein or polypeptide variants retain functionality as enzymes, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequences presented herein and possess enzymatic function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

Among other things, the present disclosure relates to non-naturally occurring microorganisms that include a gene encoding a variant of a MucK transporter protein, where the microorganism is capable of at least one of growing on terephthalic acid (TPA), catabolizing TPA, and/or transporting TPA. In some embodiments of the present disclosure, a microorganism may further include the deletion of an endogenous gene encoding a DcaS transcriptional regulator. In some embodiments of the present disclosure, the microorganism may include at least one of a bacterium, a yeast, and/or a fungus. In some embodiments of the present disclosure, the microorganism may include a bacterium. In some embodiments of the present disclosure, the bacterium may include a strain from at least one of *Acinetobacter baylyi* (*A. baylyi*), *Pseudomonas Putida* (*P. putida*), *Pseudomonas fluorescens* (*P. fluorescens*), and/or *Pseudomonas stutzeri* (*P. stutzeri*). As described herein, in some embodiments of the present disclosure, a biosensor was incorporated into non-naturally occurring micro-organisms to identify strains capable of at least one of growing on TPA, catabolizing TPA, and/or transporting TPA.

Figure 1:
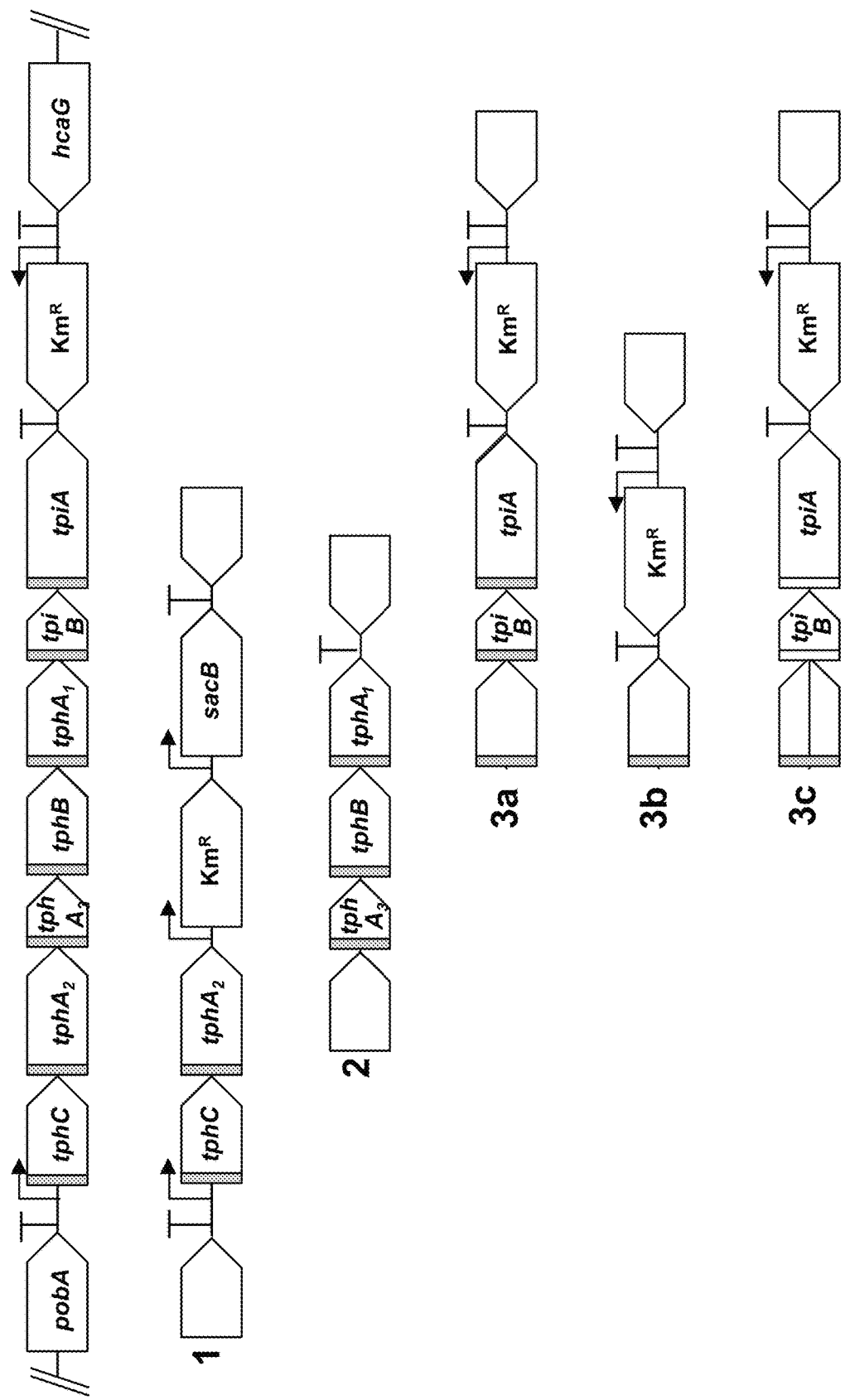
FIG. 1 illustrates step-wise integration of tph:tpi genes into the chromosome of ADP1, according to some embodiments of the present disclosure. The top line shows the schematic representation of the initial design of the synthetic operon, targeting the pobA-hcaG intergenic region. The PCR products used for the step-wise integration, containing inserted genes flanked by ~1 kbp targeting regions, are numbered 1 to 3. Cells transformed with PCR products 1 and 3a-3c were selected on MMP+Km. Cells transformed with PCR product 2 were selected on YT+25% sucrose. Strain IP101 was obtained from transformation of ADP1 with 1. Strain IP103 was obtained from transformation of IP101 with 2. Strain IP115 was obtained from transformation of IP103 with 3b. Strain IP130 was obtained from transformation of IP103 with 3c. Transformation with 3a (tpiBA with strong RBS sequences, shown in gray) was unsuccessful.
Figure 2:
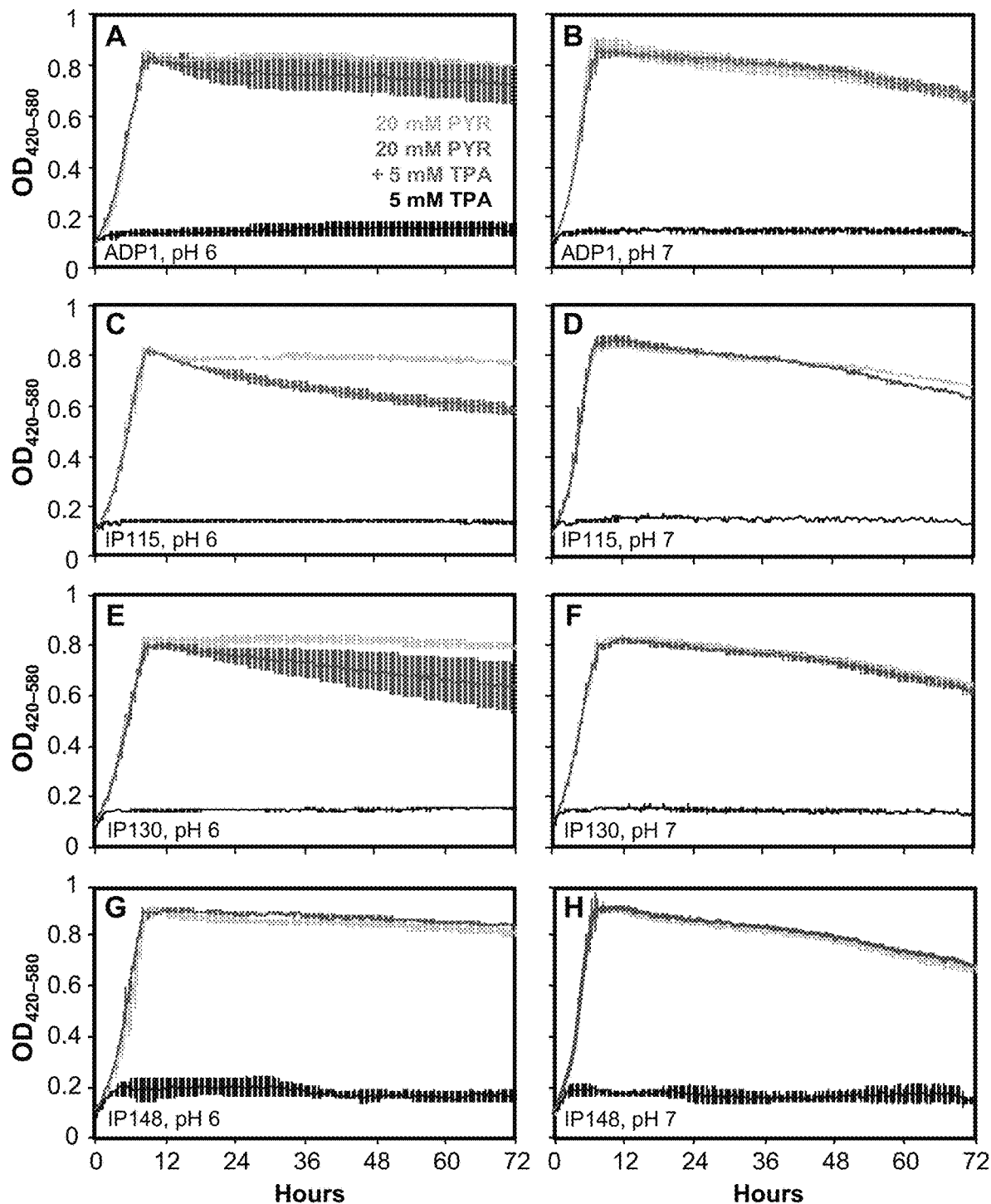
FIG. 2 illustrates the growth ($OD_{420}$-$5_{80}$) of ADP1 (A, B), IP115 (C, D), IP130 (E, F) and IP148 (G, H) in minimal medium supplemented with 20 mM pyruvate (light gray), 5 mM TPA (black), or 20 mM pyruvate+5 mM TPA (dark gray), according to some embodiments of the present disclosure. The medium was adjusted to pH 6 (A, C, E, G) or pH 7 (B, D, F, H). Average and standard deviation for three biological replicates are shown.

Among other things, adaptive laboratory evolution was performed on an *Acinetobacter* baylyi ADP1 engineered strain for growth on the xenobiotic compound terephthalic acid, a component of the plastic polyethylene terephthalate (PET). Sequencing revealed that the native muconate transporter MucK had acquired mutations in several of the evolved clones, and that mutations that could inactivate a putative repressor of expression of MucK (i.e. DcaS) had also been selected. Using a transcription-factor based TPA fluorescent biosensor, it was demonstrated that TPA uptake in ADP1 strains expressing mutated versions of MucK and/or with dcaS gene deleted was more efficient than in wild-type ADP1. In particular, the MucK variants with improved performance contained the following amino acid mutations: i) M34I and E53G, ii) M34L and T342L, and iii) Y133C (see FIG. 1). Furthermore, it was also shown that expression of MucK in a different bacterium, namely *Pseudomonas putida* KT2440, also enables uptake of TPA, similarly to what is observed in strains expressing the TPA transporter TpaK from *Rhodococcus jostii* RHA1 (see FIG. 2).

As described herein, TPA conversion was engineered in *Acinetobacter* baylyi ADP1 via the heterologous expression of catabolic and transporter genes from a native TPA-utilizing bacterium. Specifically, ADP1-derived strains were derived capable of growing on TPA as the sole carbon source using chromosomal insertion and targeted amplification of the tph catabolic operon from *Comamonas* sp. E6. Adaptive laboratory evolution was then used to improve growth on this substrate. TPA consumption rates of the evolved strains, which retained multiple copies of the tph genes, were ~0.2 g/L/h (or ~1 g TPA/g cells/h), similar to that of *Comamonas* sp. E6 and almost 2-fold higher than that of *Rhodococcus jostii* RHA1, another native TPA-utilizing strain. To evaluate TPA transport in the evolved ADP1 strains, a TPA biosensor was used that included the transcription factor TphR and a fluorescent reporter. In combination with whole-genome sequencing, the TPA biosensor revealed that transport of TPA was not mediated by the heterologous proteins from *Comamonas* sp. E6. Instead, the endogenous ADP1 muconate transporter MucK, a member of the major facilitator superfamily, was responsible for TPA transport in several evolved strains in which MucK variants were found to enhance TPA uptake. Furthermore, the IclR-type transcriptional regulator DcaS was identified as a repressor of mucK expression.

Results:

Heterologous Expression of Genes Encoding TPA Transport and Catabolism in ADPI:

To confer growth on TPA, genes needed to convert this substrate to PCA were introduced, a metabolite that is consumed via the native β-ketoadipate pathway, into ADP1 (see FIG. 3, Panels A and B). The first step of this conversion, i.e. the hydroxylation of the aromatic ring, is catalyzed by TPADO. This multicomponent enzyme includes a two-subunit Rieske non-heme iron oxygenase, encoded by $tphA_2$ and $tphA_3$, and a multi-domain reductase component, encoded by $tphA_1$. The second step in forming PCA is catalyzed by a diol dehydrogenase, encoded by tphB. Furthermore, we predicted that growth on TPA would require a transporter. For this purpose, we also introduced the genes coding for the TPA-TTT, consisting of a periplasmic substrate binding protein, encoded by tphC, and two cytoplasmic transmembrane proteins, encoded by tpiA and tpiB. In *Comamonas* sp. E6, all the tph genes are organized in an operon, whereas tpiBA form a distinct transcriptional unit. Here, the *Comamonas* genes of the tphn operon and the tpiBA genes were codon optimized for expression in ADP1 and synthesized as a polycistronic DNA cassette (see FIG. 3, Panel B).

Initially, high expression of all genes was targeted by replacing the native promoter with a constitutive tac promoter ($P_{tac}$) and by inserting synthetic ribosome binding site (RBS) sequences with high predicted translation initiation rates (TIR, ~10,000 arbitrary units, a.u.). However, attempts to integrate this large cassette into the ADP1 chromosome were unsuccessful. This fragment had 9 kbp of synthetic sequence, flanked on either side by 2 kbp of DNA identical to the chromosomal target for integration downstream of pobA. To reduce the size of the transforming DNA, the synthetic cassette was split into three fragments for use in a stepwise integration plan (see FIG. 1). The results suggested that the difficulty with integration of the foreign DNA was specific to the tpiBA genes. Since high-level synthesis of the transmembrane proteins might be toxic to the cell, the DNA sequence was modified to lower the expression of these genes. First, the RBS sequences for these genes were redesigned to match the predicted TIRs for the native tpiBA genes in *Comamonas* sp. E6 (2,841 and 333 a.u. for tpiB and tpiA, respectively). Additionally, the initial ATG in tpiB was replaced with GTG to match that of the native *Comamonas* sp. E6 gene. In this way, the tphCA$_2$A$_3$BA$_1$:tpiBA genes were integrated into the ADP1 chromosome to generate strain IP130 (see FIG. 3, Panel B).

Next, we evaluated the effect of pH on TPA consumption by wild-type ADP1, IP130, and a strain lacking tpiBA (IP115), (see FIGS. 3, Panels C-E)). In contrast to wild type and IP115, IP130 turned over small amounts of TPA (~10%) when pyruvate, which minimizes catabolic repression of aromatic metabolism, was provided as a growth substrate. However, all strains presented a Tpa$^-$ phenotype—i.e., were unable to grow on TPA as the sole carbon and energy source (see FIG. 2). The amount of TPA consumed by IP130 was higher at pH 6 than at pH 7 (p-values <0.05 for a two-tailed t-test between TPA consumed at pH 6 and at pH 7 for 48-through 120-h timepoints). Since no significant consumption of TPA was observed for IP115, these results suggest that, although minimally, TPA uptake might be enhanced when tpiBA genes are expressed.

Gene Amplification and Adaptive Laboratory Evolution by EASy:

With the aim of developing Tpa$^+$ strains (i.e., capable of growing on TPA as sole carbon and energy source), we next amplified the chromosomal gene dosage of the tph genes to initiate adaptive laboratory evolution (ALE). Given the potential toxicity to the cell of synthesizing the transmembrane proteins at a high level, we first reorganized the synthetic operon so that the tpiBA genes would not be part of the amplicon (boundaries shown for IP148 in FIG. 3, Panel B). As observed for strain IP130, IP148 turned over small amounts of TPA when grown on pyruvate, but remained Tpa$^-$ (see FIG. 3, Panel F and FIG. 2).

IP148 was transformed with the SBF, which serves as a platform for homologous recombination and precise duplication of chromosomal segments. This duplication enables changes in the number of tandemly arrayed amplicon copies under selective pressure. In this way, transformants with increased gene dosage were first selected on MMP plates with high Km. Selective pressure was then changed to growth on TPA as the sole carbon source, and Tpa$^+$ colonies arose after ~10 days (in the absence of antibiotics). When these colonies were re-streaked, Tpa$^+$ colonies appeared more rapidly, after only 2-3 days. Although individual colonies each represent a clonal population, the proclivity of the tandem copies to increase or decrease via recombination suggests that different cells within the colony may differ in amplicon copy number. Frequent recombination also promotes additional genetic change, so that all cells in any Tpa$^+$ colony may not be genetically identical. Therefore, we hereafter refer to these Tpa$^+$ mutants as isolates.

Four isolates, designated TPA_1 to TPA_4, were selected to initiate ALE. These were grown in liquid MM with 5 mM TPA, and cultures were serially transferred to enrich for mutations enabling faster growth. Given that lower pH values could advantageously favor diffusion of TPA into the cell, serial transfers for ALE with these isolates were conducted at pH 6 and pH 7 in parallel (8 lineages, designated by 0.6 or 0.7 after the isolate name to indicate the pH of the medium used for serial transfer (see FIG. 4). The copy number of the amplicon was monitored regularly by qPCR of the Km$^R$ gene to assess whether a reduction in gene dosage resulted from the selection of beneficial mutations that improve cell fitness. After initial serial transfers inoculated by 100-fold dilution every 48 h in 5 mM TPA, the selection pressure for ALE was gradually increased with the aim of improving tolerance, growth, and TPA consumption rates. This was first done by diluting cells 100-fold every 24 hours in 5 mM TPA, and then 200-fold every 24 hours in 10 mM TPA. The evolution of the gene copy number over time for the eight lineages is shown in FIG. 4.

In parallel with ALE, we also sequenced PCR products amplified from the tpiBA genes from IP148 and isolates TPA_1 to TPA_4, to test whether early acquisition of beneficial mutations in the transporter genes could have enabled growth on TPA. Sequencing revealed that all of them, including parent-strain IP148, carried an unexpected mutation in tpiA that would result in a premature stop codon (GAG→UAG (see FIG. 6)). This tpiA1481 allele is predicted to encode a 365-residue peptide [TpiA(W366*)] with an early termination disrupting the 7$^{th}$ transmembrane helix (TMH), in contrast to the 503-residue TpiA protein of 11-12 predicted TMHs. Further inspection of the sequence also revealed that translation could be re-initiated from an in-phase start codon (AUG) only 12 bp downstream of the premature stop codon, with a predicted TIR of 437 a.u. This new coding sequence, referred to as allele tpiA1482, would encode a peptide corresponding to the last 133 residues of TpiA [TpiA(Δ1-370)]. Interestingly, no mutations were found in the tpiBA genes in strain IP130.

Use of a Fluorescent Biosensor to Evaluate TPA Transport:

The results from sequencing raised the question of whether the TPA-TTT was still functional in IP148 and the four Tpa$^+$ isolates, despite the mutation in tpiA. Two possibilities were contemplated. The first was that, due to the internal homology in TpiA, two TpiA(W366*) peptides, each encompassing TMHs 1-6, could form a homo-dimer that enabled TPA transport. Evolutionary studies of TTTs have shown that in homologs of TpiA, the transmembrane helices 1-6 are homologous to TMHs 7-12, suggesting that these proteins originated as a result of gene duplication and fusion. The second possibility was that, if re-initiation of translation were to occur downstream of the premature stop codon, the two individually translated peptides, TpiA (W366*) and TpiA(Δ1-370), could associate to restore function. We sought to evaluate TPA uptake in strains expressing different alleles of tpiA. To evaluate TPA transport, we required a rapid assay that would allow us to screen multiple mutants at the same time. Hence, we employed a biosensor for intracellular TPA based on the transcription factor TphR, an IclR-family member which regulates expression of the tph operon in *Comamonas* sp.

A total of three biosensors were tested, referred to herein as pTPA1, pTPA2, and pTPA3. Testing of all three sensors, not discussed herein, and out of the scope of the present disclosure, showed a negligible response towards aromatic compounds similar to TPA, such as benzoate, 4-hydroxybenzoate, PCA, and catechol, confirming the high specificity of the biosensor for TPA. Ultimately a single biosensor, pTPA3 was chosen for all subsequent work. We then re-evaluated *A. baylyi* strains encoding the different variants of the TPA-TTT using the pTPA3 biosensor (see FIG. 5). In contrast to our expectation, the fluorescent response in all strains were comparable. In fact, wild-type ADP1, which does not encode a TPA-TTT, also responded to increasing TPA concentrations. Nevertheless, the reduced response of IP148 with respect to IP337 and IP348 (all encoding the split TpiA variant) suggested that the biosensor was sufficiently sensitive to detect the turnover of small amount of TPA when the tph catabolic genes were expressed from a single copy in IP148. It should also be noted that, in the absence of TPA, IP148 and IP337 still exhibited higher fluorescence signals relative to other strains, as observed with pTPA1. This observation supported the hypothesis that the increased fluorescence signal in these two strains was independent of TPA uptake or the biosensor plasmid, and instead was likely due to a mutation in the genome that affected expression of the sfGFP gene.

In all, no significant differences were found between ADP1-derived strains expressing different alleles of tpiA (i.e. IP297, IP313, and IP348). Furthermore, their fluorescent response was barely above that of wild type. We also note that no differences in growth rates were observed for any of the strains at the TPA concentrations tested. These results suggest that the heterologous TPA-TTT would have a minimal role in TPA uptake in *A. baylyi*, and that the evolved TPA⁺ isolates could instead be importing this substrate through an unidentified, native transporter.

Phenotypic Characterization of Evolved *A. baylyi* Isolates:

After ~100 transfers of ALE (~750 generations), the copy number of the amplicon stabilized at 15-25 copies without substantial changes in growth rates (see FIG. 4 and FIGS. 8A and 8B). Therefore, single colonies were isolated from each lineage for phenotypic characterization and WGS. The copy-number ratio of tphA₂ over the Km$^R$ gene for the selected isolates was confirmed to be of ~1, suggesting that qPCR of the latter accurately estimates the copy number of the entire amplicon defined by the SBF (see FIG. 9). Shake-flask cultures of early ALE populations (~30 generations) and post-evolution isolates showed that growth rates and TPA consumption rates were enhanced (see FIG. 10), except for populations TPA_2.6 and TPA_2.7 and their respective evolved isolates IP247 and IP250 (see FIG. 10, Panels C and D). However, it is notable that the amplicon copy number in these populations had decreased from ~40 to ~20 copies during ALE (see FIG. 4 and FIGS. 8A and 8B). An important decrease in the lag-phase was also observed, especially in the case of IP254 with respect to early population TPA_3.7 (see FIG. 10, Panel F). Moreover, tolerance to increasing TPA concentrations was enhanced in several evolved strains (see FIG. 11). No important phenotypic differences were observed between isolates derived from the parallel evolution at pH 6 compared to that at pH 7, although growth and TPA utilization appeared to be slightly faster at pH 6 than at pH 7.

We also compared the evolved *A. baylyi* isolates to the native TPA-utilizing bacteria *Comamonas* sp. E6 and *R. jostii* RHA1, both grown at the standard pH 7 (see FIG. 12 and Table 1). Growth and TPA consumption rates of the evolved Tpa⁺ isolates were slightly lower than those of *Comamonas* sp. E6 (an average of 0.40 h⁻¹ and 0.20 g/L/h, respectively, in the evolved *A. baylyi* isolates, compared to 0.50 h⁻¹ and 0.26 g/L/h in *Comamonas* sp. E6), which was the source of the catabolic and TTT genes expressed in the engineered *A. baylyi* strains. In contrast, the evolved isolates out-performed *R. jostii* RHA1, which had a 12-hour lag phase, a 0.26 h⁻¹ growth rate and a 0.13 g/L/h TPA consumption rate. Specific consumption rate values for the evolved isolates (~1 g TPA/g cells/h in average) were also between those of *Comamonas* sp. E6 (1.55 g/g/h) and *R. jostii* RHA1 (0.46 g/g/h).

TABLE 1

Growth and substrate consumption parameters for Tpa⁺ EASy lineages after ~30 generations, evolved isolates after ~750 generations, *Comamonas* sp. E6, and *Rhodococcus jostii* RHA1.

| Lineage, isolate, or strain | Specific growth rate μ (h⁻¹) | Doubling time (h) | TPA consumption rate (g/L/h) | Specific consumption rate $q_s$ (g/g/h) |
|---|---|---|---|---|
| TPA_1.6 | 0.27 ± 0.01 | 2.54 ± 0.05 | 0.14 ± 0.00 | 0.71 ± 0.02 |
| TPA_1.7 | 0.32 ± 0.01 | 2.14 ± 0.03 | 0.17 ± 0.01 | 0.75 ± 0.01 |
| TPA_2.6 | 0.43 ± 0.01 | 1.60 ± 0.01 | 0.19 ± 0.00 | 0.98 ± 0.01 |
| TPA_2.7 | 0.39 ± 0.00 | 1.78 ± 0.01 | 0.18 ± 0.00 | 0.91 ± 0.01 |
| TPA_3.6 | 0.22 ± 0.00 | 3.18 ± 0.03 | 0.13 ± 0.00 | 0.59 ± 0.01 |
| TPA_3.7 | 0.09 ± 0.00 | 7.41 ± 0.08 | 0.11 ± 0.00 | 0.29 ± 0.00 |
| TPA_4.6 | 0.16 ± 0.00 | 4.24 ± 0.01 | 0.12 ± 0.00 | 0.45 ± 0.00 |
| TPA_4.7 | 0.18 ± 0.00 | 3.78 ± 0.01 | 0.15 ± 0.01 | 0.45 ± 0.01 |
| IP243 | 0.40 ± 0.01 | 1.74 ± 0.07 | 0.22 ± 0.01 | 0.95 ± 0.05 |
| IP246 | 0.40 ± 0.02 | 1.73 ± 0.08 | 0.19 ± 0.00 | 0.98 ± 0.06 |
| IP247 | 0.43 ± 0.01 | 1.63 ± 0.02 | 0.23 ± 0.01 | 0.97 ± 0.01 |
| IP250 | 0.45 ± 0.01 | 1.56 ± 0.05 | 0.22 ± 0.02 | 1.02 ± 0.06 |
| IP251 | 0.39 ± 0.01 | 1.78 ± 0.04 | 0.17 ± 0.00 | 1.07 ± 0.03 |
| IP254 | 0.29 ± 0.01 | 2.39 ± 0.11 | 0.19 ± 0.00 | 0.79 ± 0.03 |
| IP255 | 0.43 ± 0.00 | 1.61 ± 0.01 | 0.22 ± 0.00 | 1.04 ± 0.01 |
| IP258 | 0.43 ± 0.00 | 1.61 ± 0.01 | 0.19 ± 0.00 | 1.06 ± 0.04 |
| E6 | 0.50 ± 0.01 | 1.39 ± 0.03 | 0.26 ± 0.01 | 1.55 ± 0.11 |
| RHA1 | 0.26 ± 0.00 | 2.66 ± 0.03 | 0.13 ± 0.00 | 0.46 ± 0.01 |

TABLE 2

Summary table of mutations, relative to wild-type ADP1, found in coding DNA sequences with >80% variant frequency.

| Locus | Description | Protein effect | IP148 | IP243 | IP246 | IP247 | IP250 | IP251 | IP254 | IP255 | IP258 | Count |
|---|---|---|---|---|---|---|---|---|---|---|---|---|
| ACIAD_RS08285 | Hypothetical protein | None | X | X | X | X | X | X | X | X | X | 9 |
| ACIAD_RS13200 | RNA polymerase sigma factor RpoD | Amino acid replacement | X | X |  | X | X | X | X | X | X | 8 |
| ACIAD_RS07750 | MFS transporter MucK | Amino acid replacement |  | X | X |  |  |  |  | X | X | 4 |
| ACIAD_RS07760 | IclR transcriptional regulator DcaS | Amino acid replacement/ Truncation |  | X¹ | X¹ |  |  |  |  | X² | X² | 4 |
| ACIAD_RS10455 | 16S rRNA (uracil(1498)-N(3))-methyltransferase | Truncation |  | X | X | X | X |  |  |  |  | 4 |
| ACIAD_RS00385 | EpsG family protein | Insertion |  | X |  |  |  | X |  | X |  | 3 |
| ACIAD_RS00595 | MFS transporter GudP | Amino acid replacement |  |  |  | X | X |  |  |  |  | 2 |
| ACIAD_RS00620 | FadR family transcriptional regulator | Truncation |  |  |  | X | X |  |  |  |  | 2 |
| ACIAD_RS08520/ ACIAD_RS08570 | Hypothetical protein | Truncation |  |  |  | X |  |  |  |  | X | 2 |
| ACIAD_RS15190 | Membrane protein | Partial deletion of N-terminus |  |  |  |  | X |  | X |  |  | 2 |
| ACIAD_RS00395 | Gluosyltransferase family 2 protein | Insertion |  |  |  |  | X |  |  |  |  | 1 |
| ACIAD_RS00475 | UDP-glucose 4-epimerase GalE | Truncation |  |  |  |  |  |  |  | X |  | 1 |
| ACIAD_RS01220 | Sigma-54-dependent Fis family transcriptional | Truncation |  |  |  |  | X |  |  |  |  | 1 |

TABLE 2-continued

Summary table of mutations, relative to wild-type ADP1, found in coding DNA sequences with >80% variant frequency.

| Locus | Description | Protein effect | IP148 | IP243 | IP246 | IP247 | IP250 | IP251 | IP254 | IP255 | IP258 | Count |
|---|---|---|---|---|---|---|---|---|---|---|---|---|
| | regulator | | | | | | | | | | | |
| ACIAD_RS01685 | Type IV-A pilus assembly ATPase PilB | Truncation | | | | | | X | | | | 1 |
| ACIAD_RS03905 | Cell division protein ZipA | Truncation | | | | | | | X | | | 1 |
| ACIAD_RS04405 | Hypothetical protein | Truncation | | | | | | | | X | | 1 |
| ACIAD_RS15025 | Type IV pilus modification protein PilV | Truncation | | | | X | | | | | | 1 |
| ACIAD_RS15030 | Prepilin-type N-terminal cleavage/methylation domain-containing protein | Truncation | | | | X | | | | | | 1 |
| ACIAD_RS15180 | Pilus assembly protein PilP | Partial deletion of N-terminus | | | | | | | | | X | 1 |

As observed in the phenotypic characterization of the evolved isolates, there were no clear trends in the mutations found for the lineages evolved at pH 6 or at pH 7, except for an in-phase tandem repeat in the gene coding for an EpsG family protein (ACIAD_RS00385) that was present in 3 out of the 4 isolates evolved at pH 6 and absent in all those evolved at pH 7 (see Table 2A). The mutation in tpiA, initially identified in the parent-strain IP148 and the amplified derivatives that were used to initiate ALE (TPA_1 to TPA_4), was maintained in all evolved isolates. This fact suggests that this mutation, potentially encoding a truncated or split TpiA, was not disadvantageous for growth on TPA. Unexpectedly, no mutations were found in the tph genes, except for a single nucleotide change in the synthetic RBS sequence preceding tphA$_3$ in IP251 and IP254, both derived from TPA_3. Nevertheless, it should be noted that the short reads provided by the Illumina sequencing method do not allow the detection of mutations that might be present in only one of the multiple copies of the amplicon and that could be beneficial for growth on TPA.

Another mutation identified in the parent-strain IP148 encoded a variant of the RNA polymerase sigma-70 factor, RpoD(A87E). This mutation was maintained in all evolved isolates except IP246 (see Table 2A). A different mutation in rpoD results in a growth deficit in ADP1. However, a growth competition experiment showed that RpoD(A87E) was only minimally detrimental to growth. Residue A87 is located in region 1.1 of RpoD, which is involved in promoter binding. Therefore, this mutation could potentially affect transcription efficiency in the cell. Indeed, when the mutated rpoD was replaced by the wild-type allele in IP148 derivatives, the high baseline fluorescence observed when transformed with the biosensor plasmid pTPA3 was reduced (see FIG. 13). As RpoD is the primary or "housekeeping" sigma factor in many bacteria, it is possible that this mutation alters the gene expression profile in ADP1. Additional experiments to confirm this possibility are needed.

Further analysis of WGS data revealed that 4 out of the 8 isolates (derived from TPA_1 and TPA_4) had mutations in mucK (ACIAD_RS07750) in combination with mutations in dcaS (ACIAD_RS07760), which are two genes in close proximity in the chromosome (see FIG. 14A). Moreover, the spontaneous amplification of the dca-pca-qui-pob supraoperonic cluster in IP251 and IP254 (derived from TPA_3) included the mucK and dcaS genes. These two isolates also had a mutation in the mucK-caiB intergenic region. The prevalence of mutations in these loci suggested that MucK and DcaS may have a relevant role in the Tpa$^+$ phenotype.

A DcaS homolog from *Brucella abortus*, also an IclR-type regulator, has been identified as a repressor of adipic acid metabolism therein, and its crystal structure has been solved. Using this structure as template (PDB 5WHM, 62% sequence identity), three-dimensional structure models of DcaS were built to examine the location of the amino acid replacements encoded by the different evolved isolates (see FIG. 15). In the case of IP243 and IP246, these replacements are located in the predicted A-helical linker involved in dimerization (V101G) and the ligand-binding pocket (A134E). In IP255 and IP258, the deletion of bases 499 and 500 in the dcaS coding sequence causes a shift in the open reading frame. The resulting DcaS variant would lack residues 169-282, which form part of the ligand-binding domain. Based on this analysis, these amino acid changes are predicted to disrupt DcaS function. The DNA sequences for the wild-type MucK gene (SEQ ID NO: 1), the mutated MucK gene from strain IP258 (SEQ ID NO: 3), and the mutated MucK gene from strain IP243 (SEQ ID NO: 5).

TABLE 2B

Wild-type MucK gene and variants

| SEQ ID NO | Type/name | DNA sequence |
|---|---|---|
| SEQ ID NO: 1 | wild type | atgtacagca acaatcagag atccagaatt ggatcacaca catggaaaat tgctttttta tttgcatttt tagcgttgct tgtggatgga gcagacctga tgttgctctc ttatagttta aacagtatta aagctgagtt taatttaagt acagttgaag ctggaatgtt gggaagtttt actttagctg gcatggcgat aggtggaatc tttggtgggt gggcgtgtga ccgatttggt cgtgtacgca ttgttgtgat ttcaattctc acgttctcaa tcctaacgtg tggccttgga ttgactcaga gctttataca atttggtgtt ttacgtttct tcgcttcact cggtttaggt tcttatata ttgcctgcaa taccctcatg gccgaatatg ttccaacaaa ataccgtact actgttttag gtacattaca |

TABLE 2B-continued

Wild-type MucK gene and variants

| SEQ ID NO | Type/name | DNA sequence |
|---|---|---|
| | | ggctggctgg actgttggct atattgttgc caccttactg
gctggttggt taatacccga tcatggttgg cgtgtgctgt
tttatgttgc gattattcct gtacttatgg ctgtacttat
gcattttttt gtaccagaac cagcagcatg gcaacaatca
cgcttagcac catccaaaca aactgaaaca gtcaaaactt
ctgcctttaa attaatcttt caagataaac gtaaccgtaa
catgttcatt ctgtgggcac tcaccgcagg cttttctacaa
tttggttact atggcgtaaa caattggatg ccatcttatc
ttgaaagtga attgggaatg aagtttaagg aaatgacagc
ctatatggtc ggaacataca ctgccatgat tttaggaaaa
atcttggctg gctttatggc tgataaactc ggccgtcgtt
ttacttatgc atttggtgct atcggaaccg caattttttt
acctctaatc gtgttttata actcaccaga taatatttta
tatctattgg ttattttttgg tttcttgtac ggtattccat
acggtgtcaa tgcaacttac atgacagaaa gcttcccaac
agcaatacgt ggtacagcca ttggtggagc ttataatgta
ggaagattag gcgcagcgat tgccccagca actattggtt
ttctagcttc tggcggttca attggtttgg gctttgttgt
aatgggagct gcatatttta tttgtggtgt aattccagca
ctgtttatca aagaaaaaca atatgatcca caacagtctt
aa |
| SEQ ID NO: 3 | mutant/IP258 | atgtacagca acaatcagag atccagaatt ggatcacaca
catggaaaat tgcttttta tttgcattt tagcgttgct
tgtggatgga gcagacctga tattgctctc ttatagttta
aacagtatta aagctgagtt taatttaagt acagttggag
ctggaatgtt gggaagtttt actttagctg gcatggcgat
aggtggaatc tttggtgggt gggcgtgtga ccgatttggt
cgtgtacgca ttgttgtgat ttcaattctc acgttctcaa
tcctaacgtg tggccttgga ttgactcaga gctttataca
atttggtgtt ttacgtttct tcgcttcact cggtttaggt
tctttatata ttgcctgcaa tacctcatg gccgaatatg
ttccaacaaa ataccgtact actgttttag gtacattaca
ggctggctgg actgttggct atattgttgc caccttactg
gctggttggt taatacccga tcatggttgg cgtgtgctgt
tttatgttgc gattattcct gtacttatgg ctgtacttat
gcattttttt gtaccagaac cagcagcatg gcaacaatca
cgcttagcac catccaaaca aactgaaaca gtcaaaactt
ctgcctttaa attaatcttt caagataaac gtaaccgtaa
catgttcatt ctgtgggcac tcaccgcagg ctttctacaa
tttggttact atggcgtaaa caattggatg ccatcttatc
ttgaaagtga attgggaatg aagtttaagg aaatgacagc
ctatatggtc ggaacataca ctgccatgat tttaggaaaa
atcttggctg gctttatggc tgataaactc ggccgtcgtt
ttacttatgc atttggtgct          atcggaaccg
caattttttt acctctaatc gtgttttata actcaccaga
taatatttta tatctattgg ttattttttgg tttcttgtac
ggtattccat acggtgtcaa tgcaacttac atgacagaaa
gcttcccaac agcaatacgt ggtacagcca ttggtggagc
ttataatgta ggaagattag gcgcagcgat tgccccagca
actattggtt ttctagcttc tggcggttca attggtttgg
gctttgttgt aatgggagct gcatatttta tttgtggtgt
aattccagca ctgtttatca aagaaaaaca atatgatcca
caacagtctt aa |
| SEQ ID NO: 5 | mutant/IP243 | atgtacagca acaatcagag atccagaatt ggatcacaca
catggaaaat tgcttttta tttgcattt tagcgttgct
tgtggatgga gcagacctgt tgttgctctc ttatagttta
aacagtatta aagctgagtt taatttaagt acagttgaag
ctggaatgtt gggaagtttt actttagctg gcatggcgat
aggtggaatc tttggtgggt gggcgtgtga ccgatttggt
cgtgtacgca ttgttgtgat ttcaattctc acgttctcaa
tcctaacgtg tggccttgga ttgactcaga gctttataca
atttggtgtt ttacgtttct tcgcttcact cggtttaggt
tctttatata ttgcctgcaa tacctcatg gccgaatatg
ttccaacaaa ataccgtact actgttttag gtacattaca
ggctggctgg actgttggct atattgttgc caccttactg
gctggttggt taatacccga tcatggttgg cgtgtgctgt
tttatgttgc gattattcct gtacttatgg ctgtacttat
gcattttttt gtaccagaac cagcagcatg gcaacaatca
cgcttagcac catccaaaca aactgaaaca gtcaaaactt
ctgcctttaa attaatcttt caagataaac gtaaccgtaa
catgttcatt ctgtgggcac tcaccgcagg ctttctacaa
tttggttact atggcgtaaa caattggatg ccatcttatc
ttgaaagtga attgggaatg aagtttaagg aaatgacagc
ctatatggtc ggaacataca ctgccatgat tttaggaaaa |

TABLE 2B-continued

Wild-type MucK gene and variants

| SEQ ID NO | Type/name | DNA sequence |
|---|---|---|
| | | atcttggctg gctttatggc tgataaactc ggccgtcgtt |
| | | ttacttatgc atttggtgct atcggaaccg caatttttt |
| | | acctctaatc gtgttttata actcaccaga taatatttta |
| | | tatctattgg ttattttgg tttcttgtac ggtattccat |
| | | acggtgtcaa tgcaacttac atgatagaaa gcttcccaac |
| | | agcaatacgt ggtacagcca ttggtggagc ttataatgta |
| | | ggaagattag gcgcagcgat tgccccagca actattggtt |
| | | ttctagcttc tggcggttca attggtttgg gctttgttgt |
| | | aatgggagct gcatatttta tttgtggtgt aattccagca |
| | | ctgtttatca aagaaaaaca atatgatcca caacagtctt |
| | | aa |

While there were conserved dcaS mutations in evolved isolates derived from the same initial Tpa⁺ mutant, mucK mutations were different in all cases, suggesting that mutations in dcaS appeared before those in mucK (see FIG. 14A). MucK is a MFS muconate transporter in ADP1, and it belongs to the same superfamily as the TPA transporters from *Rhodococcus* species and *P. xenovorans*. Therefore, we hypothesized that MucK and its variants are capable of transporting TPA in *A. baylyi*. Furthermore, the potential loss of DcaS function in the evolved isolates, seemingly preceding the mutation of mucK, suggested that DcaS acts as a repressor of mucK transcription.

A similar combination of mutations in genes encoding a transcriptional regulator and a MFS transporter is found in evolved isolates IP247 and IP250 (both derived from TPA_2). These isolates share a ~100 bp deletion in a gene encoding a FadR-family transcriptional regulator (ACIAD_RS00620 locus). In contrast, they have two different mutations in a neighboring gene predicted to encode a glucarate/galactarate MFS transporter (gudP, ACIAD_RS00595 locus). These mutations lead to amino acid replacements R289C in IP247 and R447L in IP250 (see Table 2A). However, we decided to focus on mucK and dcaS for further evaluation, as they had apparently co-evolved in separate lineages.

Evaluation of MucK as a TPA Transporter and its Regulation by DcaS:

To test our hypothesis that MucK was importing TPA, we first attempted to knock out its coding gene in the eight evolved isolates. However, due to a presumed loss of natural competency, we were only able to knock out mucK in IP243 and IP255, 2 out of the 4 isolates that had mutations in this gene. Consistent with our hypothesis, these mutants lost the ability to grow on either muconate (Muc⁻ phenotype) or TPA (see FIG. 16).

We then tested whether the deletion of dcaS and/or replacement of wild-type mucK with the four alleles selected during ALE enabled growth of the IP148 parent strain on TPA (see Table 3). The resulting IP148-derived mutants were inoculated in MM with 10 mM TPA as a sole carbon and energy source. After an incubation of 1-2 weeks, 8 out of 9 mutant cultures started growing and reached saturation in 24-48 h, indicating that each of these genetic modifications was sufficient to enable growth on TPA. The exception was strain IP402, carrying the allele encoding MucK(W150C I403T), which unexpectedly also presented a Muc⁻ phenotype. However, when this allele was expressed in a ΔdcaS background (strain IP417), Muc⁺ and Tpa⁺ phenotypes were observed, indicating that MucK(W150C I403T) was still functional. As expected, control mutants IP367 and IP387 with mucK knocked out were Tpa and Muc⁻, even if dcaS was deleted in the latter. Consistent with previous observations, no growth on TPA was observed for parent-strain IP148 after 2 weeks of incubation.

TABLE 3

Growth on muconate (Muc phenotype) and TPA (Tpa phenotype) of IP148-derived dcaS and mucK mutants.

| | | MucK | Phenotype | |
|---|---|---|---|---|
| Strain | Mutations | variant | Muc | Tpa |
| IP148 | None | Native | + | − |
| IP367 | ΔmucK::Sm$^R$:sacB | None | − | − |
| IP378 | ΔdcaS | Native | + | + |
| IP387 | ΔdcaS ΔmucK::Sm$^R$:sacB | None | − | − |
| IP398 | ΔmucK::mucK258 | M34I E53G | + | + |
| IP400 | ΔmucK::mucK243 | M34L T342I | + | + |
| IP402 | ΔmucK::mucK255 | W150C I403T | − | − |
| IP411 | ΔmucK::mucK246 | Y133C | + | + |
| IP413 | ΔdcaS ΔmucK::mucK258 | M34I E53G | + | + |
| IP415 | ΔdcaS ΔmucK::mucK243 | M34L T342I | + | + |
| IP417 | ΔdcaS ΔmucK::mucK255 | W150C I403T | + | + |
| IP419 | ΔdcaS ΔmucK::mucK246 | Y133C | + | + |

Given the natural propensity of bacteria to undergo spontaneous gene duplication and amplification to increase gene expression under selective pressure, we tested whether these IP148-derived Tpa⁺ mutants still retained a single copy of the synthetic tph operon or if it had been duplicated. For this purpose, we collected the Tpa⁺ cells from the TPA cultures indicated in Table 4 to evaluate the copy number by qPCR. Unlike the case of the Tpa⁺ strains obtained by transformation with an SBF to delimit the amplicon, it was possible that in these new mutants an amplified chromosomal region may not include the Km$^R$ gene. Therefore, we used primers and a probe specific for tphA₂. We found that, indeed, all Tpa⁺ mutants had 6-14 copies of tphA₂ (See FIG. 17). This result indicates that the deletion of dcaS and/or expression of different mucK alleles is sufficient to enable growth on TPA, but that multiple copies of the tph catabolic genes are needed to sustain growth of *A. baylyi* on TPA as sole carbon and energy source.

TABLE 4

Description of *A. baylyi* strains, isolates, and lineages used in this work. For the purpose of standardized nomenclature, tphA genes are numbered in subscript to differentiate them from mutated alleles. More details on the genotype and strain construction can be found in Table 8.

| Strains, isolates, and lineages | Relevant features |
|---|---|
| Strains | |
| ADP1 | Wild type |
| IP115 | pobA:$P_{tac}$:tphCA$_2$A$_3$BA$_1$:Ω$Km^R$ |
| IP130 | pobA:$P_{tac}$:tphCA$_2$A$_3$BA$_1$:tpiB:Ω$Km^R$ |
| IP148 | pobA:$P_{tac}$:tphCA$_2$A$_3$BA$_1$:Ω$Km^R$:$P_{trc}$:tpiBA1481:tpiA1482 [tpiA1481 encodes TpiA(W366*); tpiA1482 encodes TpiA(Δ1-370)] |
| IP297 | pobA:$P_{tac}$:tphC:Ω$Km^R$:$P_{trc}$:tpiBA1481 |
| IP313 | pobA:$P_{tac}$:tphC:Ω$Km^R$:$P_{trc}$:tpiBA |
| IP337 | pobA:$P_{tac}$:tphC:Ω$Km^R$:$P_{trc}$:tpiBA1481:tphA1482 (obtained by deletion of tphA$_2$A$_3$BA$_1$ genes in IP148) |
| IP348 | pobA:$P_{tac}$:tphC:Ω$Km^R$:$P_{trc}$:tpiBA1481:tphA1482 (obtained by de novo integration in ADP1) |
| IP367 | IP148-derived mutant, ΔmucK::$Sm^R$:sacB |
| IP378 | IP148-derived mutant, ΔdcaS |
| IP387 | IP148-derived mutant, ΔdcaS ΔmucK::$Sm^R$:sacB |
| IP398 | IP148-derived mutant, ΔmucK::mucK258 [encodes MucK(M34I E53G)] |
| IP400 | IP148-derived mutant, ΔmucK::mucK243 [encodes MucK(M34L T342I)] |
| IP402 | IP148-derived mutant, ΔmucK::mucK255 [encodes MucK(W150C I403T)] |
| IP411 | IP148-derived mutant, ΔmucK::mucK246 [encodes MucK(Y133C)] |
| IP413 | IP148-derived mutant, ΔdcaS ΔmucK::mucK258 |
| IP415 | IP148-derived mutant, ΔdcaS ΔmucK::mucK243 |
| IP417 | IP148-derived mutant, ΔdcaS ΔmucK::mucK255 |
| IP419 | IP148-derived mutant, ΔdcaS ΔmucK::mucK246 |
| IP461 | ADP1-derived mutant, ΔdcaS |
| IP492 | ADP1-derived mutant, ΔmucK::mucK258 |
| IP493 | ADP1-derived mutant, ΔmucK::mucK243 |
| IP494 | ADP1-derived mutant, ΔmucK::mucK255 |
| IP495 | ADP1-derived mutant, ΔmucK::mucK246 |
| IP496 | ADP1-derived mutant, ΔdcaS ΔmucK::mucK258 |
| IP497 | ADP1-derived mutant, ΔdcaS ΔmucK::mucK243 |
| IP498 | ADP1-derived mutant, ΔdcaS ΔmucK::mucK255 |
| IP499 | ADP1-derived mutant, ΔdcaS ΔmucK::mucK246 |
| Tpa$^+$ isolates and ALE lineages (multiple copies of tph genes) | |
| TPA_1 | IP148-derived isolate, used to initiate ALE |
| TPA_2 | IP148-derived isolate, used to initiate ALE |
| TPA_3 | IP148-derived isolate, used to initiate ALE |
| TPA_4 | IP148-derived isolate, used to initiate ALE |
| TPA_1.6 | ALE lineage derived from TPA_1, evolved at pH 6 |
| TPA_1.7 | ALE lineage derived from TPA_1, evolved at pH 7 |
| TPA_2.6 | ALE lineage derived from TPA_2, evolved at pH 6 |
| TPA_2.7 | ALE lineage derived from TPA_2, evolved at pH 7 |
| TPA_3.6 | ALE lineage derived from TPA_3, evolved at pH 6 |
| TPA_3.7 | ALE lineage derived from TPA_3, evolved at pH 7 |
| TPA_4.6 | ALE lineage derived from TPA_4, evolved at pH 6 |
| TPA_4.7 | ALE lineage derived from TPA_4, evolved at pH 7 |
| IP243 | Isolate from lineage TPA_1.6 after ~750 generations |
| IP246 | Isolate from lineage TPA_1.7 after ~750 generations |
| IP247 | Isolate from lineage TPA_2.6 after ~750 generations |
| IP250 | Isolate from lineage TPA_2.7 after ~750 generations |
| IP251 | Isolate from lineage TPA_3.6 after ~750 generations |
| IP254 | Isolate from lineage TPA_3.7 after ~750 generations |
| IP255 | Isolate from lineage TPA_4.6 after ~750 generations |
| IP258 | Isolate from lineage TPA_4.7 after ~750 generations |

The apparent sequential emergence of dcaS and mucK mutations in the EASy lineages derived from TPA_1 and TPA_4, and the observation that deletion of dcaS alone enabled a Tpa$^+$ phenotype in IP148-derived mutants, strongly suggested that DcaS acts as a repressor of the transcription of mucK. To test this hypothesis, we used RT-qPCR in wild-type ADP1 and a Δ dcaS mutant (IP461) grown on 20 mM pyruvate, 10 mM muconate, or 10 mM PCA. In wild-type ADP1, transcription of mucK is induced in the presence of muconate when compared to an unrelated carbon source, i.e. pyruvate (see FIG. 14B). Conversely, transcription of mucK is constitutive for all conditions in the Δ dcaS strain IP461, confirming our hypothesis that DcaS is a transcriptional repressor of mucK. Additionally, a slight repression of mucK transcription in the presence of PCA was observed in wild-type ADP1, suggesting that the generation of this intermediate during TPA catabolism could impede further uptake of TPA by MucK. This effect might explain why mutations that inactivate DcaS were selected early on during ALE.

Next, we evaluated how deletion of dcaS affected TPA uptake using our biosensor. For this assessment, we transformed the third-generation TPA biosensor pTPA3 into IP461 and compared the fluorescent response to increasing TPA concentrations to that of wild-type ADP1 (see FIG. 14B). Indeed, the ΔdcaS strain IP461 exhibited higher fluorescence at lower TPA concentrations, and a significant fluorescent response above baseline (no TPA) was detected for this strain in as low as 0.01 mM TPA (p-value <0.001 for a two-tailed t-test). The results obtained for IP461 are in clear contrast to those presented in FIG. 5 for the TPA-TTT mutants, further supporting the hypothesis that the heterologous transporter has a minimal impact in TPA uptake in ADP1.

Finally, we sought to assess how mutations in mucK affected uptake of TPA in the presence or absence of DcaS. Hence, we replaced the native mucK gene in either wild-type ADP1 or IP461 backgrounds, transformed all strains with pTPA3, and evaluated fluorescence in the presence or absence of TPA. In order to detect differences in uptake efficiency between the different MucK variants, we induced expression of the sfGFP gene with 0.01 mM TPA, the lowest concentration tested at which wild-type ADP1 did not exhibit a fluorescent response but IP461 did (see FIG. 14B). As shown in FIG. 14C, the expression of all mutated mucK alleles, except that encoding MucK(W150C I403T), resulted in an increased extent of fluorescence in the presence of TPA. These results demonstrate that at least 3 of the 4 MucK variants that arose during ALE are more efficient in TPA uptake than native MucK. Furthermore, the increased fluorescent response was synergistic with the deletion of dcaS, which is consistent with our finding that deletion of this transcription factor increases expression of mucK. Thus, in some embodiments of the present disclosure, a non-naturally occurring microorganism, capable of, among other things, at least one of the catabolism, transport, or growth of TPA may include a mutation to a MucK gene according to at least one of SEQ ID NOs: 3, 5, and/or 7 (mucK258, mucK243, and mucK246, respectively). In some embodiments of the present disclosure, a non-naturally occurring microorganism, capable of, among other things, at least one of the catabolism, transport, or growth of TPA may include a mutation to a MucK protein according to at least one of SEQ ID Nos: 4, 6, and/or 8 (mucK258, mucK243, and mucK246, respectively).

Discussion:

In this work, our goal was to engineer *A. baylyi* ADP1 to grow on TPA as a sole carbon and energy source using EASy with the tph catabolic genes from *Comamonas* sp. E6, a native TPA-utilizing bacterium. To that end, we successfully evolved *A. baylyi* strains for improved growth and consumption rates on this substrate. ALE through serial transfer did not lead to the isolation of Tpa+ strains with less than −15 copies of the tph catabolic operon. While WGS [whole genome sequencing] of evolved isolates identified beneficial mutations that enabled growth of ADP1 mutants on TPA (i.e. in dcaS and mucK), none of these were found to lie within the exogenous catabolic or transporter genes. Furthermore, the reintroduction of these beneficial mutations in the parent strain IP148 still led to the spontaneous amplification of the tph genes upon selection for growth on TPA (see Table 4 and FIG. 17). These results demonstrate that ADP1 requires multiple copies of these genes to support growth on TPA as sole carbon and energy source, and highlight the benefit of gene amplification as a natural mechanism employed by microorganisms to rapidly increase gene expression in response to an abrupt selective pressure.

Interestingly, the TPA catabolic gene clusters in TPA-utilizing bacteria *Comamonas* sp. E6, *R. jostii* RHA1, and *Rhodococcus* sp. DK17 are duplicated in the genomes of these organisms. Additionally, the presence of transposable elements and DNA modifying genes (integrases, recombinases, and reverse transcriptases) in the immediate vicinity of the TPA operons in these three bacteria and in *D. tsurhuratensis* (de visu inspection of publicly available sequences) suggest that these may have been acquired through horizontal gene transfer. Considering the xenobiotic nature of TPA, it is likely that TPA catabolism has appeared recently, and that it has not yet fully evolved to be as efficient as the catabolism of other aromatic compounds that are ubiquitous in nature, such as those derived from lignin. In this sense EASy, by combining increased gene dosage and ALE, mimics how new catabolic pathways can evolve in nature: acquisition of exogenous genes through horizontal gene transfer, duplication of the acquired genes to overcome limitations in expression, and/or selection of mutations in the acquired or native genes that enable new functions.

In particular, here we have identified variants of the ADP1 muconate MFS transporter MucK that are more efficient at importing TPA. It should be stressed that this discovery would not have been possible without amplification of the tph catabolic genes by EASy, which enabled the growth on TPA that was needed to initiate ALE. Of note, WGS data hint that GudP, another MFS [major facilitator superfamily] transporter predicted to transport glutarate/galactarate, could have also evolved to transport TPA in the engineered strains. The fact that both transporters are involved in the uptake of dicarboxylic acid suggests that they have a latent activity towards TPA that was improved through ALE. As there are no predicted TTTs in ADP1, it is possible that the transmembrane proteins TpiBA from *Comamonas* sp. E6 are not properly folded or sufficiently active in the heterologous host, and that ADP1 would instead favor MFS transporters to import TPA. However, alignments for MucK and GudP against known TPA MFS transporters (i.e. TpaK) from *Rhodococcus* sp. or *P. xenovorans* show sequence identities below 26% (see FIGS. 18A-18D). Therefore, the prediction of this latent function by sequence analysis alone would have been improbable. The improved MucK variants identified here expand the known toolset of transporters that can be expressed in heterologous hosts to enable TPA uptake.

In this work, we have also discovered that the transcription factor DcaS represses expression of MucK and that PCA, a metabolite generated during TPA catabolism, could also inhibit the expression of this transporter. Cross-regulation between the catechol (cat gene cluster) and PCA (pca gene cluster) branches of the P-ketoadipate pathway in ADP1, which will favor the former, are well documented in the literature (Bleichrodt et al., 2010; Brzostowicz et al., 2003; Siehler et al., 2007). However, their interaction with the dca gene cluster, involved in the catabolism of saturated $C_6$-$C_{10}$ dicarboxylic acids (Parke et al., 2001), has not been extensively studied. It should be noted that the dca gene cluster encodes another IclR-type regulator, DcaR (Fischer et al., 2008), that could add another layer of regulation that has not been elucidated in the present study (see FIG. 14A). Further analysis of the cross-talk between the different branches of the P-ketoadipate pathway would be of interest when engineering the metabolism of ADP1 towards substrates that are funneled through this pathway such as TPA, as cross-regulation could affect productivity and yields in bioprocesses aimed at the conversion of these substrates into value-added bioproducts (Beckham et al., 2016; Johnson et al., 2019).

Materials and Methods:

Strains and Culture Media:

*A. baylyi* ADP1 (American Type Culture Collection ATCC 33305) and derived strains were routinely grown aerobically at 30° C. in minimal medium (MM) (Shanley et al., 1986), consisting of 0.5 M $KH_2PO_4$, 0.5 M $Na_2HPO_4$, 10% $(NH_4)_2SO_4$, and 1 mL concentrated base solution. Concentrated base solution contained (per liter): 20 g nitriloacetic acid (dissolved in 600 mL H$_2$O with 14.6 g KOH); 28.9 g MgSO$_4$; 6.67 g CaCl$_2$·2H$_2$O; 18.5 mg Mo$_7$O$_{24}$·4H$_2$O; 198 mg FeSO$_4$·7H$_2$O; and 100 mL of Metals 44 solution. The Metals 44 solution contained (per liter): 2.5 g EDTA; 10.95 g ZnSO$_4$·7H$_2$O; 5 g FeSO$_4$·7H$_2$O; 1.54 g MnSO$_4$·7H$_2$O; 392 mg CuSO$_4$·5H$_2$O; 250 mg Co(NO$_3$)$_2$·6H$_2$O; and 177 mg Na$_2$B$_4$O$_7$·10H$_2$O. Minimal medium was supplemented with 20 mM pyruvate (hereafter MMP) or 5 or 10 mM TPA as carbon sources, unless otherwise indicated. For growth on plates, 1.5% w/v agar was added. When noted, the media was adjusted to pH 6 by changing the ratio of phosphate salts. *Comamonas* sp. E6 (Biological Resource Center, NITE, strain number 107749) and *Rhodococcus jostii* RHA1 (kindly provided by Dr. Lindsay Eltis from the University of British Columbia) were grown in lysogeny broth (LB) or MM supplemented with 10 mM TPA. *Escherichia coli* NEB 5-alpha F'I$^q$ and NEB 5-alpha cells (New England Biolabs) were grown in LB broth. Antibiotic concentrations used for ADP1 were 25 µg/mL (standard) or 1 mg/mL (high) kanamycin (Km), and 25 µg/mL streptomycin (Sm). For *E. coli*, 100 µg/mL ampicillin (Ap), and 50 µg/mL Km or Sm were used.

Plasmid Construction:

Routine PCR amplifications were carried out using Phusion High-Fidelity DNA polymerase (New England Biolabs) and primers synthesized by Integrated DNA Technologies (IDT) or Eurofins. Synthetic, double-stranded DNA fragments (gBlocks) were also synthesized by IDT. Plasmids were constructed either by NEBuilder HiFi DNA assembly or by ligation with T4 DNA ligase (both from New England Biolabs). Plasmids containing P$_{tac}$ were transformed and maintained in NEB 5-alpha F'I$^q$ cells. All plasmid inserts were verified by Sanger sequencing, performed by GENEWIZ. Details on plasmid construction and primer and gBlock sequences can be found in Tables 5-7.

TABLE 5

Plasmids used in this study. For the purpose of standardized nomenclature, tphA genes are numbered in subscript to differentiate them from mutated alleles.

| Plasmid ID | Description and construction details | References |
|---|---|---|
| pUC19 | Cloning vector. Ap$^R$. | (Norrander et al., 1983) |
| PUI1637 | Source for ΩKm$^R$ cassette. Ap$^R$ Km$^R$. | (Eraso and Kaplan, 1994) |
| pBAV1K-lacI-P$_{trc}$-gusA | Broad host range vector for inducible expression in ADP1. Km$^R$. | Addgene 30503 (Murin et al., 2012) |
| pBAV1K-P$_{T5}$-gfp | Broad host range vector for constitutive expression in ADP1. Km$^R$. | Addgene 26702 (Bryksin and Matsumura, 2010) |
| pTargetF | Source for Sm$^R$ gene with promoter sequence. Sm$^R$. | Addgene 62226 (Jiang et al., 2015) |
| pBTL-2 | Broad host range expression vector. Km$^R$. | Addgene 22806 (Lynch and Gill, 2006) |
| pBTL-2-tphR-sfGFP | tphR gene along with tphR-tphC intergenic region (P$_{tph}$) was amplified from *Comamonas testosteroni* genome (ATCC 700441D-5). The spacer between the start codon of tphC and RBS site in P$_{tph}$ was changed from CAAG to TATACAT (represented as P$_{tph-RBS}$) using oRJ125/oRJ122. The tphR-P$_{tph-RBS}$ was then PCR assembled with the sfGFP coding sequence to create the sensor-reporter cassette (tphR-P$_{tph-RBS}$-sfGFP). The pBTL-2 backbone (PCR amplified using oRJ17-03 + oRJ17-04) and the sensor-reporter cassette were assembled into a circular plasmid using the NEBuilder HiFi assembly kit. The resultant plasmid showed the sensor-reporter cassette between tonB and soxR terminators. | This study |
| pCJ050 | Modified pK18mobsacB vector with EcoRI/PstI/XbaI/BamHI sites replacing the P$_{lac}$:lacZ cassette. oCJ345 and oCJ289 were used to amplify pK18mobsacB, excluding the P$_{lac}$:lacZ cassette, and the product was re-circularized using the KLD enzyme mix from New England Biolabs. Km$^R$. | (Schäfer et al., 1994), this study |
| pIP019 | pUC19 vector carrying P$_{tac}$:tphA$_2$A$_3$BA$_1$:tpiBA:Km$^R$. gBlocks IP_tph_tpi-Opt_ADP1-1, IP_tph_tpi-Opt_ADP1-2, and IP_tph_tpi-Opt_ADP1-3, and the Km$^R$:T0 fragment amplified from pBAV1K-lacI-P$_{trc}$-gusA with oIP037 + oIP038, were assembled into pUC19 digested with BamHI-HF and HindIII-HF. Two single nucleotide deletions in tphA2 were corrected by site-directed mutagenesis. For this, three overlapping fragments were amplified with oIP042.1 + oIP129, oIP128 + oIP131 and oIP130 + oIP043, respectively. These were assembled by SOE and the resulting cassette cloned by NEBuilder HiFi DNA assembly into the original plasmid, previously linearized with SmaI and XhoI. Ap$^R$ Km$^R$. | This study |
| pIP020 | pUC19 vector carrying P$_{tac}$:tphA$_2$A$_3$BA$_1$:tpiBA flanked by ~2 kbp targeting regions for integration between pobA and hcaG loci in ADP1. Upstream and downstream targeting regions were amplified from ADP1 gDNA with oIP117 + oIP089 and oIP119 + oIP120, respectively. P$_{tac}$:tphCA2A3BA1:tpiBA was amplified from pIP019 with oIP090 + oIP118. PCR products were assembled into pUC19 digested with BamHI and HindIII. Ap$^R$. | This study |
| pIP021 | pIP020 plasmid carrying ΔKm$^R$ cassette downstream tpiA. pIP020 and pUI1637 were digested with PmeI, and the cassette ligated into linear pIP020. Km$^R$ gene is in convergent orientation with respect to synthetic genes. Ap$^R$ Km$^R$. | This study mucKKm$^R$ |

TABLE 5-continued

Plasmids used in this study. For the purpose of standardized nomenclature, tphA genes are numbered in subscript to differentiate them from mutated alleles.

| Plasmid ID | Description and construction details | References |
|---|---|---|
| pIP031 | pUC19 vector carrying $P_{tac}$:tphA$_2$A$_3$BA$_1$:tpiBA flanked by ~2 kbp targeting regions for integration between pobA and hcaG loci in ADP1. Includes weak RBS sequences of reduced TIR for tpiBA and GTG start codon for tpiB. tpiB, flanked by new RBS sequences for tpiB (2840.59 TIR with GTG start codon) and tpiA (496.23 TIR), was amplified from pIP020 with oIP160 + oIP163, and assembled into pIP020 linearized by PCR with oIP162 + oIP161. Ap$^R$. | This study |
| pIP032 | pIP031 plasmid carrying $\Omega$Km$^R$ cassette downstream tpiA. pIP031 and pUI1637 were digested with SpeI, and the $\Omega$Km$^R$ cassette ligated into linear pIP031. Km$^R$ gene is in convergent orientation with respect to synthetic genes. Ap$^R$ Km$^R$. | This study |
| pIP037 | pBAV1K-lacI vector carrying $P_{trc}$:tpiBA with weak RBSs and alternative start codon. tpiBA was amplified from pIP032 with oIP185 + oIP186 and assembled into pBAV1K-lacI-$P_{trc}$, previously linearized with oIP183 + oIP184. Km$^R$. | This study |
| pIP040 | pUC19 vector carrying $P_{tac}$:tphA$_2$A$_3$BA$_1$ $P_{trc}$:tpiBA (with weak RBSs and alternative start codon) flanked by ~2 kbp targeting regions for integration between pobA and hcaG loci in ADP1. $P_{trc}$:tpiBA was amplified from pIP037 with oIP189 + oIP190 and assembled into pIP031, previously linearized with oIP187 + oIP188. Ap$^R$. | This study |
| pIP041 | pIP040 plasmid carrying $\Omega$Km$^R$ cassette between tphA$_1$ and $P_{trc}$:tpiBA. pIP040 and pUI1637 were digested with ApaI, and the $\Omega$Km$^R$ cassette ligated into linear pIP040. Km$^R$ gene is in convergent orientation with respect to tph genes. Ap$^R$ Km$^R$. | This study |
| pIP055 | Modified pBAV1K-$P_{T5}$-gfp with Sm$^R$ instead of Km$^R$ (backbone hereafter referred to as pBAV1S vector). pBAV1K-$P_{T5}$-gfp was digested with XbaI and SacI to remove Km$^R$ and its promoter sequence. Sm$^R$ with its promoter was obtained by digestion of pTargetF with XbaI and SacI, and ligated into the linear vector backbone. Sm$^R$. | This study |
| pIP064 | pUC19 vector carrying $P_{tac}$:tphC:$P_{trc}$:tpiBA (with weak RBSs and alternative start codon) flanked by ~2 kbp targeting regions for integration between pobA and hcaG loci in ADP1. pUC19 with $P_{tac}$:tphC and targeting regions was amplified by PCR from pIP031 with oIP187 + oIP292. $P_{trc}$:tpiBA was amplified from pIP037 with oIP291 + oIP190. Products were assembled with the NEBuilder HiFi DNA assembly kit. Ap$^R$. | This study |
| pIP065 | pUC19 vector carrying $P_{tac}$:tphC:$P_{trc}$:tpiBA297 (with weak RBSs and alternative start codon) flanked by ~2 kbp targeting regions for integration between pobA and hcaG loci in ADP1. pUC19 with $P_{tac}$:tphC and targeting regions was amplified by PCR from pIP031 with oIP187 + oIP292. $P_{trc}$:tpiBA297 was amplified from pIP037 with oIP291 + oIP306. Products were assembled with the NEBuilder HiFi DNA assembly kit. Ap$^R$. | This study |
| pIP073 | pIP064 carrying $\Omega$Km$^R$ cassette between tphC and $P_{trc}$:tpiBA. pIP064 and pUI1637 were digested with ApaI, and the $\Omega$Km$^R$ cassette ligated into linear pIP064. Km$^R$ gene is in convergent orientation with respect to tphC. Ap$^R$ Km$^R$. | This study |
| pIP075 | pIP065 carrying $\Omega$Km$^R$ cassette between tphC and $P_{trc}$:tpiBA297. pIP064 and pUI1637 were digested with ApaI, and the $\Omega$Km$^R$ cassette ligated into linear pIP065. Km$^R$ gene is in convergent orientation with respect to tphC. Ap$^R$ Km$^R$. | This study |
| pIP088 | pCJ050-based vector with Sm$^R$ replacing Km$^R$. pCJ050 was linearized by PCR with oIP340 + oIP341. Sm$^R$ and promoter region were amplified from pTargetF with oIP342 + oIP343. Products were assembled with NEBuilder HiFi DNA assembly kit. Sm$^R$. | This study |
| pIP089 | pUC19 vector carrying $P_{tac}$:tphC:SmP:sacB:$P_{trc}$:tpiBA flanked by ~2 kbp targeting regions for integration between pobA and hcaG loci in ADP1. pIP041 was linearized by PCR with oIP345 + oIP344. Sm$^R$:sacB was amplified from pIP088 with oIP346 + oIP002. Products were assembled with NEBuilder HiFi DNA assembly kit. Ap$^R$ Sm$^R$. | This study |
| pIP102 | pUC19 vector carrying Sm$^R$:sacB cassette flanked by ~1 kbp targeting regions for replacement of dcaS. Sm$^R$:sacB cassette was amplified from pIP088 with oIP346 + oIP002. Upstream and downstream targeting regions were respectively amplified from IP148 gDNA with oIP393 + oIP395 and oIP396 + oIP394. PCR products were assembled into pUC19, previously linearized with BamHI and HindIII. Ap$^R$ Sm$^R$. | This study |

TABLE 5-continued

Plasmids used in this study. For the purpose of standardized nomenclature, tphA genes are numbered in subscript to differentiate them from mutated alleles.

| Plasmid ID | Description and construction details | References |
|---|---|---|
| pIP103 | pUC19 vector carrying $Sm^R$:sacB cassette flanked by ~1 kbp targeting regions for replacement of mucK. $Sm^R$:sacB cassette was amplified from pIP088 with oIP346 + oIP002. Upstream and downstream targeting regions were respectively amplified from IP148 gDNA with oIP402 + oIP404 and oIP405 + oIP403. PCR products were assembled into pUC19, previously linearized with BamHI and HindIII. $Ap^R$ $Sm^R$. | This study |
| pIP104 | pUC19 vector carrying ~1 kbp targeting regions for dcaS deletion. Upstream and downstream targeting regions were respectively amplified from IP148 gDNA with oIP393 + oIP397 and oIP398 + oIP394. PCR products were assembled into pUC19, previously linearized with BamHI and HindIII. $Ap^R$. | This study |
| pIP105 | pUC19 carrying mucK258 flanked by ~1 kbp targeting regions for replacement of wild-type mucK. mucK with upstream and downstream targeting regions was amplified from IP148 gDNA in two fragments with oIP402 + oIP428 and oIP427 + oIP403. PCR products were assembled into pUC19, previously linearized with BamHI and HindIII. $Ap^R$. | This study |
| pIP106 | pUC19 carrying mucK243 flanked by ~1 kbp targeting regions for replacement of wild-type mucK. mucK with upstream and downstream targeting regions was amplified from IP148 gDNA in three fragments with oIP402 + oIP418, oIP417 + oIP420 and oIP419 + oIP403. PCR products were assembled into pUC19, previously linearized with BamHI and HindIII. $Ap^R$. | This study |
| pIP107 | pUC19 carrying mucK255 variant flanked by ~1 kbp targeting regions for replacement of wild-type mucK. mucK with upstream and downstream targeting regions was amplified from IP148 gDNA in three fragments with oIP402 + oIP424, oIP423 + oIP426, and oIP425 + oIP403. PCR products were assembled into pUC19, previously linearized with BamHI and HindIII. $Ap^R$. | This study |
| pIP108 | pUC19 carrying mucK246 variant flanked by ~1 kbp targeting regions for replacement of wild-type mucK. mucK with upstream and downstream targeting regions was amplified from IP148 gDNA in two fragments with oIP402 + oIP422 and oIP421 + oIP403. PCR products were assembled into pUC19, previously linearized with BamHI and HindIII. $Ap^R$. | This study |
| pTPA1 | $1^{st}$ generation TPA sensor for use in ADP1. pBAV1S vector carrying the sensor reporter cassette tphR-$P_{tph}$-RBs-sfGFP. The sensor-reporter cassette was amplified from pBTL-2-tphR-sfGFP with oIP305 + oIP262 and assembled into pIP055 linearized with XbaI and SpeI. $Sm^R$. | This study |
| pTPA-Lib1 | Library of plasmids derived from pTPA1 with partial randomization of the -35 and -10 sites. oRJ146 and oRJ147 were mixed and PCR amplified to obtain a double stranded, diversified Ptph library. The vector backbone with TphR and sfGFP coding genes was amplified with oRJ012 + oRJ150 using pTPA1 as template. PCR products were assembled using NEBuilder HiFi DNA assembly. $Sm^R$. | This study |
| pTPA2 | $2^{nd}$ generation TPA sensor for use in ADP1, isolated from pTPA-Lib1 by FACS. Contains mutations in the -10 site of $P_{tph}$ with respect to pTPA1. $Sm^R$. | This study |
| pTPA-Lib2 | Library of plasmids derived from pTPA2 with complete randomization of the -35 site. Products from PCR amplification of pTPA1 with oRJ17-01 + oRJ152 and pTPA2 with oRJ151 + oRJ130 were assembled into the vector backbone, obtained by PCR linearization of pTPA1 with oRJ112 + oRJ17-04. $Sm^R$. | This study |
| pTPA-Lib3 | Library of plasmids derived from pTPA2 with complete randomization of the -10 site. Products from PCR amplification of pTPA1 with oRJ17-01 + oRJ154 and oRJ153 + oRJ130 were assembled into the vector backbone, obtained by PCR linearization of pTPA1 with oRJ112 + oRJ17-04. $Sm^R$. | This study |
| pTPA3 | $3^{rd}$ generation TPA sensor for use in ADP1, isolated from pTPA-Lib2 by FACS. Contains mutations in the -35 site of $P_{tph}$ with respect to pTPA2, and a single base-pair deletion between the operator and -35 sites. $Sm^R$. | This study |

TABLE 6

Oligonucleotides used for plasmid and strain construction. Overlaps for assembly are underlined. Inserted restriction sites are shown in bold. Site-directed mutations are shown in red. Forward and reverse primers are respectively indicated with (F) and (R).

| SEQ ID | Oligo ID | Sequence | Description |
|---|---|---|---|
| SEQ ID NO: 18 | oCJ289 | ctaactcacattaattgcgttgcgctcactg | Amplification of pK18mobsacB backbone (R) |
| SEQ ID NO: 19 | oCJ345 | GAATTCCTGCAGTCTAGAGGATCCctagcttcacgctgccgcaag | Amplification pK18mobsacB with EcoRI, PstI, XbaI, and BamHI sites (F) |
| SEQ ID NO: 20 | oIP002 | atcggcattttcttttgcg | Amplification of Km$^R$:sacB or Sm$^R$:sacB from pCJ050 and pIP088, respectively (R) |
| SEQ ID NO: 21 | oIP018 | atttaagcactgcactcacc | Amplification of 5'-homogy arm for integration downstream pobA (R) |
| SEQ ID NO: 22 | oIP031 | agcaaggtgagatgacagg | Amplification of 3'-end of ΩKm$^R$ Cassette for SBF construction (F) |
| SEQ ID NO: 23 | oIP037 | atggctaaaatgagaatatcacc | Amplification of Km$^R$:T0 from pBAV1K (F) |
| SEQ ID NO: 24 | oIP038 | acagctatgaccatgattacgccAAGCTTGagtgcttggattctcaccaa | Amplification of Km$^R$:T0 from pBAV1K (R) with pUC19 overlap and HindIII site |
| SEQ ID NO: 25 | oIP042.1 | gtgaattcgagctcggtacc | Amplification of gBlock IP_tph_tpi-Opt_ADP1-1 for cloning into pUC19 (F) |
| SEQ ID NO: 26 | oIP043 | ggtgatattctcattttagccat | Amplification of gBlock IP_tp_tpi-Opt_ADP1-3 for cloning upstream of Km$^R$:T0 from pBAV1K into pUC19 (R) |
| SEQ ID NO: 27 | oIP089 | cgttttatttgatgtctggttagctggcatgttttaaatagtcaag | Amplification of 5'-targeting region for integration downstream pobA (R), with rrnB T1 overlap |
| SEQ ID NO: 28 | oIP090 | gactatttaaaacatgccagctaaccagacatcaaataaaacg | Amplification of rrnB T1:P$_{tac}$:tphA2A3BA1 (F) with pobA overlap |
| SEQ ID NO: 29 | oIP096 | taatgcaagcacgtgagc | Amplification primer. Binds pobA (F) |
| SEQ ID NO: 30 | oIP117 | GTGAATTCGAGCTCGGTACCCGGGGATCCGTTTAAACCAAATTACGCAGCTCATTC | Amplification of 5'-targeting region for integration downstream pobA (F) with pUC19 overlap and PmeI site |
| SEQ ID NO: 31 | oIP118 | gctctcttttgtttaACTAGTtcaatcttctacaaggcc | Amplification of P$_{tac}$:tphA2A3BA1:tpiBA (R) with SpeI site and overlap with downstream pobA sequence |
| SEQ ID NO: 32 | oIP119 | ggcctttgtagaagattgaACTAGTtaaAACAAAAAGAGAGCGATTAG | Amplification of 3'-targeting region for integration downstream pobA (F) with tpiA overlap and SpeI site |

TABLE 6-continued

Oligonucleotides used for plasmid and strain construction. Overlaps for assembly are underlined. Inserted restriction sites are shown in bold. Site-directed mutations are shown in red. Forward and reverse primers are respectively indicated with (F) and (R).

| SEQ ID | Oligo ID | Sequence | Description |
| --- | --- | --- | --- |
| SEQ ID NO: 33 | oIP120 | aacagctatgaccatgattacgccaagcttGTTTAAACAGGCATAAGGATATTGCAATG | 2 kbp downstream ADP1 pobA amplification (R) with pUC19 overlap and PmeI site |
| SEQ ID NO: 34 | oIP128 | ctcagaaattacctaataaCtggaaactttatttgaaaatg | Mutagenic primer (F), corrects c590 deletion in tphA2 |
| SEQ ID NO: 35 | oIP129 | cattttcaaaataaagtttccaGttattaggtaatttctgag | Mutagenic primer (R), corrects c590 deletion in tphA2 |
| SEQ ID NO: 36 | oIP130 | gcagaacaacgtaaagtTcgtcttaaacaagctaatctg | Mutagenic primer (F), corrects t1013 deletion in tphA2 |
| SEQ ID NO: 37 | oIP131 | cagattagcttgtttaagacgaActttacgttgttctgc | Mutagenic primer (R), corrects t1013 deletion in tphA2 |
| SEQ ID NO: 38 | oIP145 | ggttcgcttgctgtccattcatgcctgcatttcttgtc | Amplification of pobA:$P_{tac}$:tphC:tphA2 (R) with Km$^R$:sacB overlap for stepwise integration of TPA degradation cluster |
| SEQ ID NO: 39 | oIP146 | cgcaaaagaaaatgccgatgttaaaacaaaagagagcgattag | Amplification of downstream ADP1 pobA flanking region from pIP021 with KmR/SacB overlap (F), for stepwise integration of TPA degradation cluster in ADP1 |
| SEQ ID NO: 40 | oIP160 | cctacaggtcaccactagCGGAACGGCGATgtgaaaattaaaagtcaaaag | Amplification of tpiB (F) for insertion of synthetic RBS with 1952.24 TIR and alternative start codon gtg, contains overlap with tphA2 |
| SEQ ID NO: 41 | oIP161 | cttttttgacttttaattttcacATCGCCGTTCCGctagtggtgacctgtagg | Linearization of pIP021 (R) for insertion of synthetic RBS with 1952.24 TIR upstream tpiB and alternative start codon gtg contains overlap with tpiB |
| SEQ ID NO: 42 | oIP162 | catttatcgcgggttaaCCGGTAAGCGGatggatcttattcaaaac | Linearization of pIP021 (F) for insertion of synthetic RBS with 496.23 TIR upstream tpiA contains overlap with tpiB |
| SEQ ID NO: 43 | oIP163 | gttttgaataagatccatGCCGCTTACCGGttaacccgcgataaatg | Amplification of tpiB (R) for insertion of synthetic RBS with 496.23 TIR upstream tpiA, contains overlap with tpiA |
| SEQ ID NO: 44 | oIP180 | cgttttatttgatgtctggcgataccgtcgacctc | Amplification of 3'-end of ΩKm$^R$ cassette for SBF construction (R), contains overlap with 5'-end of $P_{tac}$:tph cassette |

TABLE 6-continued

Oligonucleotides used for plasmid and strain construction. Overlaps for assembly are underlined. Inserted restriction sites are shown in bold. Site-directed mutations are shown in red. Forward and reverse primers are respectively indicated with (F) and (R).

| SEQ ID | Oligo ID | Sequence | Description |
|---|---|---|---|
| SEQ ID NO: 45 | oIP181 | gaggtcgacggtatcgccagAcatcaaataaaacg | Amplification of 5'-end of $P_{tac}$:tph cassette for SBF construction (F), contains overlap with 3'-end of $\Omega Km^R$ cassette |
| SEQ ID NO: 46 | oIP182 | aagggcaagagccatc | Amplification of 5'-end of $P_{tac}$:tph cassette for SBF construction (R) |
| SEQ ID NO: 47 | oIP183 | aaaggagaagcttactagtagc | Linearization of pBAV1K-$P_{trc}$ for assembly (F) |
| SEQ ID NO: 48 | oIP184 | gtgtgaaattgttatccgctc | Linearization of pBAV1K-$P_{trc}$ for assembly (R) |
| SEQ ID NO: 49 | oIP185 | gagcggataacaatttcacacTGGAGCGCACACgtgaaattaaaagtcaaaaag | Amplification of tpiB (F) with $P_{trc}$ overlap and synthetic RBS with 1705.68 TIR |
| SEQ ID NO: 50 | oIP186 | gctactagtaagcttctccttttcaatcttctacaaaggcctc | Amplification of tpiA (R) with pBAV1K overlap |
| SEQ ID NO: 51 | oIP187 | actagttaaaacaaaaagagagc | Linearization of pIP031 for assembly (F) |
| SEQ ID NO: 52 | oIP188 | GGGCCCctagtggtgacctgtagg | Linearization of pIP031 for assembly (R), introduces ApaI site |
| SEQ ID NO: 53 | oIP189 | tcctacaggtcaccactagGGGCCCgagctgttgacaattaatcatC | Amplification of $P_{trc}$:tpiBA (F) with ApaI site and pIP031 overlap |
| SEQ ID NO: 54 | oIP190 | tcgctctcttttgttttaactagttcaatcttctacaaaggcctc | Amplification of $P_{trc}$:tpiBA (R) with pIP031 overlap |
| SEQ ID NO: 55 | 0IP262 | gccctgaggcctgcagcggccgcTACTAGTttacctaggtgtgaattcagaac | Amplification of tphR-sfGFP (R), contains SpeI site and pBAV overlap |
| SEQ ID NO: 56 | oIP291 | gagctgttgacaattaatcatcc | Amplification of $P_{trc}$:tpiBA (F) |
| SEQ ID NO: 57 | oIP292 | gatgattaattgtcaacagctcGGGCCCttaaagttttacgtttgctgc | Amplification of tphC (R) with ApaI site and $P_{trc}$ overlap |
| SEQ ID NO: 58 | oIP305 | agatctaagcttctgcaggtcgacTCTAGAcggatccccctcaagtc | Amplification of tphR-sfGFP (F) with XbaI site and pBAV overlap |
| SEQ ID NO: 59 | oIP306 | tcgctctcttttgttttaACTAGTTacatgcttgcaataagacc | Amplification of truncated tpiA (R), contains SpeI site and overlap with downstream pobA sequence |
| SEQ ID NO: 60 | oIP340 | tgagcgggactctgg | Linearization of pCJ050 (R) |
| SEQ ID NO: 61 | oIP341 | gcagcgtgaagctagg | Linearization of pCJ050 (F). |
| SEQ ID NO: 62 | oIP342 | gatccctagcttcacgctgccctgttatccctactcgag | Amplification of $Sm^R$ (F) with pCJ050 overlap |
| SEQ ID NO: 63 | oIP343 | gaaccccagagtcccgctcatttgccgactaccttgg | Amplification of $Sm^R$ (R) with pCJ050 overlap |
| SEQ ID NO: 64 | oIP344 | taaaaacgcaaaagaaaatgccgatgtctagctatcgccatg | Linearization of pIP041 (R) with sacB overlap |

TABLE 6-continued

Oligonucleotides used for plasmid and strain construction. Overlaps for assembly are underlined. Inserted restriction sites are shown in bold. Site-directed mutations are shown in red. Forward and reverse primers are respectively indicated with (F) and (R).

| SEQ ID | Oligo ID | Sequence | Description |
| --- | --- | --- | --- |
| SEQ ID NO: 65 | oIP345 | taacagggcagcgtgaagctagggattaaagttttacgtttgctgc | Linearization of pIP041 (F) with Sm$^R$ overlap |
| SEQ ID NO: 66 | oIP346 | tccctagcttcacgctgc | Amplification of SM$^R$:sacB (F) |
| SEQ ID NO: 67 | oIP393 | GTGAATTCGAGCTCGGTACCCGGGGATCC*GTTTAAAC*cactgtcaaagctcaacc | Amplification of upstream targeting region targeting dcaS (F), contains BamHI and PmeI sites, and pUC19 overlap |
| SEQ ID NO: 68 | oIP394 | AACAGCTATGACCATGATTACGCCAAGCTT*GTTTAAAC*ttattggcatctttgggtactt | Amplification of downstream targeting region targeting dcaS (R), contains HindIII and PmeI sites, and pUC19 overlap |
| SEQ ID NO: 69 | oIP395 | gcagcgtgaagctagggacataggaaagagtatactcaactc | Amplification of upstream targeting region targeting dcaS (R), contains overlap with Sm$^R$ |
| SEQ ID NO: 70 | oIp396 | cgcaaaagaaaatgccgattaaaaaatatcgcaaaatgcgtac | Amplification of downstream targeting region targeting dcaS (F), contains overlap with sacB |
| SEQ ID NO: 71 | oIP397 | attttgcgatatttttacataggaaagagtatactcaactc | Amplification of upstream targeting region targeting dcaS (R), contains overlap with downstream targeting region |
| SEQ ID NO: 72 | oIP398 | gagtatactctttcctatgtaaaaaatatcgcaaaatgcgtac | Amplification of downstream targeting region targeting dcaS (F), contains overlap with upstream targeting region. |
| SEQ ID NO: 73 | oIP402 | gtgaattcgagctcggtacccggGGATCC*GTTTAAAC*agatactgtttgatcagtgg | Amplification of downstream targeting region targeting mucK (F), contains BamHI and PmeI sites, and pUC19 overlap |
| SEQ ID NO: 74 | oIP403 | aacagctatgaccatgattacgccAAGCTT*GTTTAAAC*caggtactttacctgaagc | Amplification of upstream targeting region targeting mucK (R), contains HindIII and PmeI sites and pUC19 overlap |
| SEQ ID NO: 75 | oIP404 | gcagcgtgaagctagggataacttataaatgcttatacacttc | Amplification of downstream targeting region targeting mucK (R), contains overlap with Sm$^R$ |
| SEQ ID NO: 76 | oIP405 | cgcaaaagaaaatgccgatcatagctatattcctttagcaaag | Amplification of upstream targeting region of targeting mucK (F), contains overlap for assembly with sacB |
| SEQ ID NO: 77 | oIP417 | ggaagctttctAtcatgtaagttgc | mucK mutagenic primer, encodes T342I (R) |

TABLE 6-continued

Oligonucleotides used for plasmid and strain construction. Overlaps for assembly are underlined. Inserted restriction sites are shown in bold. Site-directed mutations are shown in red. Forward and reverse primers are respectively indicated with (F) and (R).

| SEQ ID | Oligo ID | Sequence | Description |
| --- | --- | --- | --- |
| SEQ ID NO: 78 | oIP418 | cttacatgaTagaaagcttcccaac | mucK mutagenic primer, encodes T342I (F) |
| SEQ ID NO: 79 | oIP419 | gagagcaacaAcaggtctgctcc | mucK mutagenic primer, encodes M43L (R) |
| SEQ ID NO: 80 | oIP420 | ggagcagacctgTtgttgctctc | mucK mutagenic primer, encodes M43L (F) |
| SEQ ID NO: 81 | oIP421 | gttggaacaCattcggccatgag | mucK mutagenic primer, encodes Y133C (R) |
| SEQ ID NO: 82 | oIP422 | ctcatggccgaatGtgttccaacaaaatac | mucK mutagenic primer, encodes Y133C (F) |
| SEQ ID NO: 83 | oIP423 | gtttttctttgGtaaacagtgctgg | mucK mutagenic primer, encodes I403T (R) |
| SEQ ID NO: 84 | oIP424 | ccagcactgtttaCcaaagaaaaacaatatg | mucK mutagenic primer, encodes I403T (F) |
| SEQ ID NO: 85 | oIP425 | atagccaacagtAcagccagcctg | mucK mutagenic primer, encodes W150C (R) |
| SEQ ID NO: 86 | oIP426 | caggctggctgTactgttggctatattg | mucK mutagenic primer, encodes W150C (F) |
| SEQ ID NO: 87 | oIP427 | ctcagctttaatactgtttaaactataagagagcaaTatcaggtctgctc | mucK mutagenic primer, encodes M34I (R) and contains overlap with oIP428. |
| SEQ ID NO: 88 | oIP428 | ttaaacagtattaaagctgagtttaatttaagtacagttgGagctggaatg | mucK mutagenic primer, encodes E53G (F) and contains overlap with oIP427. |
| SEQ ID NO: 89 | oIP475 | aacttctaaaaattaacgcatagc | Amplification of rpoD with targeting regions (F) |
| SEQ ID NO: 90 | oIP476 | gtcactgggtatgagaatatg | Amplification of rpoD with targeting regions (F) |
| SEQ ID NO: 91 | oRJ17-01 | tgctatggaggtcaggtatg | Sequencing primer, binds downstream of tonB terminator in pBTL-2 or pTPA plasmids (F) |
| SEQ ID NO: 92 | oRJ17-03 | gatatcattcaggacgagcctcagactcc | Amplification of pBTL-2 backbone (F) |
| SEQ ID NO: 93 | oRJ17-04 | aatcatacctgacctccatagcagaaagtcaaaag | Amplification of pBTL-2 or pTPA backbone (R) |
| SEQ ID NO: 94 | oRJ17-08 | gaggctcgtcctgaatgatatcttacctaggtgtgaattcagaac | Ampliification of sfGFP gene; provides overlapping sequence with pBTL-2 backbone for NEBuilder HiFi assembly (R) |
| SEQ ID NO: 95 | oRJ012 | AAGGAGAtatacatatggctagcaaaggagaagaac | Amplification of sfGFP gene with a canonical RBS site at the 5' end (F) |
| SEQ ID NO: 96 | oRJ112 | catggcatggatgagctctac | Amplification of vector backbone; binds 3' end of the sfGFP gene (F) |

TABLE 6-continued

Oligonucleotides used for plasmid and strain construction. Overlaps for assembly are underlined. Inserted restriction sites are shown in bold. Site-directed mutations are shown in red. Forward and reverse primers are respectively indicated with (F) and (R).

| SEQ ID | Oligo ID | Sequence | Description |
| --- | --- | --- | --- |
| SEQ ID NO: 97 | oRJ122 | tttgctagccatatgtataTCTCCTTcttgtgtggggaactgcag | Amplification of $P_{tph}$ with an overlapping sequence with sfGFP gene and canonical RBS (R) |
| SEQ ID NO: 98 | oRJ125 | tgctatggaggtcaggtatgattctacaacccctgcggat | Amplification of tphR gene; provides overlapping sequence with pBTL-2 backbone for NEBuilder HiFi assembly (F) |
| SEQ ID NO: 99 | oRJ130 | ttacctaggtgtgaattcagaacc | Amplification of sfGFP gene from 3' end (R) |
| SEQ ID NO: 100 | oRJ146 | tttgctagccatatgtatatctccttcttgtgtggngaactgcaNTNTNAggatgtcgtactttg | Partially randomized $P_{tph}$ at -10 site for pTPA-Lib1 (R), contains overlap with oRJ147 |
| SEQ ID NO: 101 | oRJ147 | gttttcaacatttttgcgcatagcgcaaaaacaggtNTNANAcaaagtacgacatcct | Partially randomized $P_{tph}$ at -35 site for pTPA-Lib1 (F), contains overlap with oRJ146 |
| SEQ ID NO: 102 | oRJ150 | atgcgcaaaaatgttgaaaac | Amplification of pTPA1 backbone including tphR and sfGFP gene (R) |
| SEQ ID NO: 103 | oRJ151 | caaagtacgacatccttacaatg | Amplification of $P_{tph}$ downstream of -35 site for construction of pTPA-Lib2 (F) |
| SEQ ID NO: 104 | oRJ152 | cattgtaaggatgtcgtactttgNNNNNNacctgttttgcgctatgc | Completely randomized $P_{tph}$ at -35 site for construction of pTPA-Lib2 (R) |
| SEQ ID NO: 105 | oRJ153 | gtttaacacaaagtacgacatcctNNNNNNgcagttccccacacaag | Completely randomized $P_{tph}$ at -10 site for construction of pTPA-Lib3 (F) |
| SEQ ID NO: 106 | oRJ154 | aggatgtcgtactttgtgttaaac | Amplification of $P_{tph}$ upstream of -10 site for construction of pTPA-Lib3 (R) |

TABLE 7

Synthetic DNA fragment (gBlock) sequences used in this study. For the purpose of standardized nomenclature, tphA genes are numbered in subscript to differentiate them from mutated alleles.

| SEQ ID NO: | gBlock ID | Description | |
| --- | --- | --- | --- |
| SEQ ID NO: 107 | IP_tph_tpi-Opt_ADP1-1 | The second terephthalate degradation cluster tphCA$_2$A$_3$BA$_1$ and TPA transporter components tpiBA from *Comamonas* sp. E6 (Hosaka et al., 2013; Sasoh et al., 2006) were codon optimized for expression in *A. baylyi* ADP1, using the guided random codon optimizer tool at http://genomes.urv.es/ OPTIMIZER/ (Puigbò et al., | GTGAATTCGAGCTCGGTACCCGGGCCAGACATCAAATAAAACGAAAGGCTCAG TCGAAAGACTGGGCCTTTCGTTTTATCTGTTGTTTGTCGGTGAACGCTCTCAT TAATTAATCCAGAGGCAT*GAGCTGTTGACAATTAATCATCGGCTCGTATAATG TGTGGAATTGTGAGCGGATAACAATTTCACACAGGAGAGTCTATA*atgCGTA ACGAATCTATCCGTCGTCGTGAAGCGTTAATTGGTATGCTGCAGCAGTTGCA GCAACTGGTTCACTCGCTCAAAGTAACCAACCACTGAAAATCGTTGTGCCTTT TTCTGCAGGTGGTACAGCGGACGTATTACCACGTCTTGTCGCTGAAAAAATCC GTGCCGATTATGCTGGTGGTGTTATCATCGAAAACAAACCAGGTGCAGGTGGT AATATTGGTGCAGATCTAGTTTTCCGTGCTCCACCAGACGGTATGACGGTTTT AGCTTCACCACCTGGTCCTATCGCTATTAATCACAATCTTTATCAAAATTAT CTTTCGATCCTACTCGTTGGGTACCAGTAACCATTCTGGCAACAGTTCCTAAC GTACTTGTAATTAACCCAAAACTACCTGTTAAAAGCCTTGGCGAATTTATCGC ATACGCAAAAGCAAATCCAAAGAAAGTAACCGTAGCGACTCAAGGTGACGGTT |

TABLE 7-continued

Synthetic DNA fragment (gBlock) sequences used in this study. For the purpose of standardized nomenclature, tphA genes are numbered in subscript to differentiate them from mutated alleles.

| SEQ ID NO: | gBlock ID | Description | |
|---|---|---|---|
| | | 2007). Synthetic RBS were designed for all CDS using the Salis Lab RBS calculator with constraints tool (Espah Borujeni et al., 2014, 2013) targeting a TIR of 10,000 A.U. (version 1.1), except for tpiA for which the native RBS from *Comamonas* sp. E6 was maintained (predicted TIR > 10,000 A.U.). Forward rrnB T1 terminator and P*tac* promoter were included upstream of tphC. Constructions were initially designed for cloning into pUC19 together with Km$^R$:T0 (amplified from pBAV1K and including a synthetic RBS upstream Km$^R$) downstream of tpiA. Construct was divided into 3 overlapping gBlock fragments (total size: 6964 bp). gBlock-1 is 2325 bp long. rrnB T1 sequence is shown in lighter text. P*tac*, lac operator, and a spacer sequence is shown italicized. RBS sequences are shown in italicized and underlined. Overlaps for assembly are underlined. Start and stop codons for CDSs are shown in lowercase bold. | CTACTTCACACCTTACAGCAGCAATGTTTATGCAATTAACTGGTACAGAACTA ACTGTTATCCCATACAAAGGTACAGCACCAGCTTTAATCGATCTTATTGGTGG TAATGTAGACGTGTTTTTCGATAATATCAGCTCTTCTGCAACTTATCACCAAG CAGGAAAAGTTCGTATTCTTGCAGTTGCTGATGAACAACGTTCACAAATTCTT CCACAAGTTCCAACGTTCGCAGAACAACAGTGGCCAGCAATGCAAGCTGTGAC ATTTTTCTCAGTAGTGGCACCTCCTGGTACATCAGCAGAAATCGCACAAAAAC TTCAAAAACAGATGGCTCTTGCCCTTTCTTCGAACGATATTCGTAAGCACTTC CAGGAACAAGGTGCTGTGCCATGTGGTTGGGATCAAGTAAAACTGCTCAATT TATTCGTCAGGAAACCGAAAAATGGAAGAAAGTACTCAAAGCAGCAAACGTAA AACTTtaa_GAGAGGAAAGC_atgCAGGAAAGCATTATTCAATGGCATGGTGCG ACCAACACACGCGTTCCATTTGGTATCTATACAGATACCGCAAATGCTGACCA AGAACAACAGCGTATTTACCGTGGCGAAGTATGGAATTACCTTTGTTTGGAAT CAGAAATCCCAGGAGCGGGTGATTTTCGTACCACATTTGCGGGTGAAACACCT ATTGTCGTAGTTCGTGATGCTGATCAAGAAATTTATGCTTTCGAAAATCGTTG TGCTCACCGTGGTGCTTTAATTGCATTAGAAAAGAGCGGTCGTACTGATTCTT TTCAATGTGTTTATCATGCATGGTCATATAACCGTCAGGGTGACCTTACGGGT GTGGCTTTCGAAAAAGGCGTAAAAGGTCAGGGTGGTATGCCAGCTAGTTTCTG TAAAGAAGAACATGGTCCACGTAAACTTCGCGTAGCAGTGTTCTGCGGCTTGG TTTTCGGTTCTTTTTCTGAAGACGTTCCAAGTATTGAAGATTATTTGGGTCCG GAAATTTGTGAACGTATCGAACGTGTTCTCCATAAGCCTGTAGAAGTTATCGG TCGTTTTACTCAGAAATTACCTAATAACTGGAAACTTTATTTTGAAAATGTAA AAGATAGCTACCATGCATCTCTTTTACACATGTTTTTCACAACTTTCGAACTG AACCGTTTATCTCAGAAAGGCGGTGTTATTGTGGATGAGTCTGGCGGCCATCA TGTATCCTATAGTATGATTGATCGTGGGGCCAAGGATGATTCATATAAAGATC AAGCTATTCGTTCTGACAATGAACGTTATCGTTTGAAAGATCCTAGCTTACTA GAAGGTTTTGAAGAATTCGAAGATGGTGTAACGCTTCAAATTCTTAGCGTATT CCCAGGGTTTGTTTTGCAACAAATCCAAAACAGTATTGCAGTGCGTCAGTTAT TGCCAAAAAGTATTTCTAGTTCTGAATTGAACTGGACTTATTTAGGTTATGCC GATGATAGCGCAGAACAACGTAAAGTTCGTCTTAAACAAGCTAATCTGATTGG ACCTGCTGGATTCATTTCAATGGAAGATGGTGCAGTCGGCGGTTTCGTGCAGC GTGGTATTGCAGGCGCTGCTAAC<u>CTTGATGCAGTAATCGAAATGGG</u> |
| SEQ ID NO: 108 | IP_ph_tpi-Opt_ADP1-2 | See description for IP_tph_tpi-Opt_ADP1-1. gBlock22 is 2325 bp long. RBS sequences are shown italicized and underlined. Overlaps for assembly are underlined. Start and stop codons for CDS are shown in lowercase bold. | <u>CCTTGATGCAGTAATCGAAATGGG</u>CGGTGATCATGAAGGCAGCTCTGAAGGTC GCGCTACTGAAACTtcaGTACGTGGCTTTTGGAAAGCATATCGTAAACATATG GGACAAGAAATGCAGGCatga_GGAGTCCCTAAAC_atgATCAATGAAATACAG ATCGCAGCATTTAATGCAGCATATGCAAAAACTATTGACTCTGATCTATGGA ACAATGGCCTACCTTTTTTACTAAAGATTGCCATTATTGTGTAACGAATGTAG ATAATCATGATGAGGGTTTAGCTGCTGGTATAGTTTGGGCAGATTCACAGGAC ATGTTGACTGATCGTATCTCAGCTTTGCGTGGAAGCGAACATTTACGAACGTCA CCGCTATCGTCACATCTTAGGTCTGCCATCAATTCAATCAGGTGATGCAACGC AGGCATCAGCTAGCACACCTTTCATGGTTCTTCGTATCATGCATACTGGCGAA ACGGAGGTTTTCGCATCGGGTGAATATCTCGATAAATTCACTACTATTGATGG TAAATTGCGCCTTCAGGAACGTATTGCTGTTTGTGACTCTACAGTAACCGATA CCTTAATGGCATTGCCATTAtga_AAGGAGGTAACA_atgAACGCAATTGTTCAC CGCCGTCTTGCACTTGCAATTGGTGATCCACATGGTATTGGTCCTGAAATCGC ATTGAAAGCTCttCAACAGCTTTCGGTAACTGAACGTAGCTTAATTAAAGTAT ACGGTCCGGTCTGCACTTGAACAAGCAGCACGCGTTTGCGAAATGGAACCA CTCTTACAAGATATCGTACACGAAGAAGCAGGTACCTTGACCCAACCAGTACA GTGGGGTGAAATTACACCACAAGCTGGTCTTAGTACAGTACAATCAGCTACTG CTGCGATCCGTGCATGTGAAATGGTGAGGTAGATGCAGTTATTGCGTGTCCA CACCATGAAACTGCAATCCACCGTGCTGGTATCGCCTTCTCTGGTTATCCAAG CCttTTAGCGAATGTGTTGGGTATGAACGAAGATCAAGTTTTTCTTATGTTGG TTGGTGCTGGTCTTCGTATCGTTCATGTGACTCTACACGAATCTGTACGTTCT GCACTTGAACGTCTTTCTCCACAACTTGTTGTAAATGCAGCACAAGCAGCAGT TCAAACCTGTACATTGCTTGGTGTTCCTAAACCGAAAGTGGCAGTGTTCGGCA TTAACCCACATGCATCAGAAGGTCAACTTTTCGGCTTGGAAGATAGCCAAATT ACCGTTCCAGCAGTTGAAACCCTTCGTAAACGTGGTCTAGCTGTTGATGGTCC AATGGGTGCGGATATGGTACTGGCACAACGTAAACATGATTTATATGTTGCGA TGCTTCATGATCAGGGTCATATACCAATTAAACTTCTTGCACCAAATGGTGCG AGTGCTCTCTCAATCGGTGGTCGTGTTGTATTGTCATCAGTTGGACACGGCAG CGCAATGGACATCGCTGGCCGTGGCGTAGCTGATGCCACTGCTCTTTTACGTA CCATTGCTCTTCTTGGCGCTCAGCCAGTTtga_GGTCCCTCCCAA_atgAACCAT CAAATCCACATCCATGACTCAGATATTGCATTTCCATGTGCACCTGGTCAATC AGTTTTGGATGCGGCCTTACAAGCAGGTATCGAATTGCCTTATAGCTGCCGTA AAGGTTCATGTGGGAATTGTGCAAGTACTCTTTTAGATGGTAATATTGCATCT |

TABLE 7-continued

Synthetic DNA fragment (gBlock) sequences used in this study. For the purpose of standardized nomenclature, tphA genes are numbered in subscript to differentiate them from mutated alleles.

| SEQ ID NO: | gBlock ID | Description | |
|---|---|---|---|
| | | | TTCAACGGTATGGCTGTTCGTAATGAATTATGTGCGTCTGAACAAGTGTTATT<br>GTGTGGTTGCACGGCGGCATCTGATATACGTATTCATCCTTCTTCTTTCCGTC<br>GTCTTGACCCAGAAGCTCGTAAACGTTTCACTGCTAAGGTATATTCAAATACT<br>CTTGCTGCTCCAGATGTATCTCTTCTCCGTCTCCGTTTACCTGTTGGTAAACG<br>TGCTAAATTTGAAGCTGGTCAATATTTACTAATCCACTTAGATGACGGTGAGA<br>GCCGTAGCTACAGCATGGCAAATCCACCACATGAATCTGATGGTATCACCTTA<br>CATGTTCGTCATGTTCCAGGTGGGCGTTTTAGTACTATTGTACAACAATTGAA<br>ATCAGGAGATACTTTGGACATTGAATTACCTTTTGGTTCTATTGCGCTTAAAC<br>CTGATGACGCTCGTCCTCTGATCTGTGTAGCTGGTGGTACCGGCTTTGCTCCA<br>ATCAAATCCGTTTTAGACGATCTCGCGAAACGTAAAGTACAGCGCGATATCAC<br>ACTTATCTGGGCGCACGCAATCCATCTGGCTTATAT<u>CTTCCATCAGCTATCG<br>ATAAGTGG</u> |
| SEQ ID NO: 109 | IP_tph_tpi-Opt_ADP1-3 | See description for IP_tph_tpi-Opt_ADP1-1. gBlock-3 is 2347 bp long. RBS sequences are shown italicized and underlined. Overlaps for assembly are underlined. Start and stop codons for CDS are shown in lowercase bold. A XhoI site is shown in italicized. | <u>CTTCCATCAGCTATCGATAAGTGG</u>CGTAAGGTATGGCCACAATTCCGTTACAT<br>CGCCGCTATCACTGATCTTGGGGATATGCCAGCTGATGCACACGCTGGTCGTG<br>TGGACGACGCATTACGTACTCATTTTGGTAATCTGCATGATCATGTTGTTCAT<br>TGTTGTGGTTCGCCTGCTCTAGTTCAAAGTGTCCGTACAGCCGCCTCGGACAT<br>GGGTCTACTAGCGCAAGATTTCCATGCAGATGTATTTGCAACTGGTCCTACAG<br>GTCACCACtag<i>GGGGCGGAACAA</i>atgAAAATTAAAAGTCAAAAAGATTTTTTT<br>TCTGGTTTGATGTTCCTTGCAGTTGGTTTAGCATTTGCAATTGGTGCTTCAAA<br>TTATACTATTGGTACTGGTGCTCGTATGGGTCCAGGTTATTTCCCTCTTATAC<br>TTGGTGTACTGATGGCGATTCTAGGTGCAGCTATCTGTGTTGGTGGTCTTACT<br>AAAGGTCCAGAGGGTGGTGATAAAATTGGTAAATGGGCATGGCGTCAAGTTTT<br>TTTTATCTTGGCAGCAAATTTTGCATTCGGCATTTTGTTAGTGGGTGTACCAG<br>CAGTTGGTATTCCACAATTTGTCTTATTATCGCAATTTATGCGTTAGTCTTC<br>ATCGCGTCTTTGGGTGGCCACTCTTTCAACTTCAAAGAAACCGCGATCCTTGC<br>AACGGTGCTTGCAGTTGGTTCTTACTTCGCTTTTGTTTGGGCATTAAACTTAC<br>AATTCCCAGTATGGCCATCATTTATCGCGGGTtaa<i>TCAGGAGCATCGTCC</i>atg<br>GATCTTATTCAAAACTTAAGTACCGGCTTCGGTGTGGCTTTCACTTTCCAAAA<br>TTTGATTATTGTTTCGTTGGTTGTCTTTTAGGTACTTTAATTGGCGTACTTC<br>CAGGCATTGGTCCAGTTGCTACAATTGCAATGTTATTGCCTGCAACCTATGCT<br>TTACCACCAGTGGCTGCATTGATTATGTTGGCTGGTATCTACTATGGTGCGCA<br>GTATGGTGGTAGTACTACTGCTATTTTGGTAAATCTTCCGGGTGAATCTTCTT<br>CTGTAGTCACCGTTATCGATGGTTACCAAATGGCTCGTAAAGGTCGTGCAGGT<br>CCAGCGCTTGCTGCTGCTGGTATTGTTCTTTTTTCGCAGGTTGTGTTGGTAC<br>AGTGATCTTAGCGGCTTTCGCTCCACCTCTCACGGAAGTTGCATTCAAGTTTG<br>GACCTGCAGAGTATTTTTCTTTAATGACATTGGGTCTAATTGGTGCAGTTGTC<br>CTTGCTTCAGGCTCTTTGCTCAAAGCAATTGCAATGATCGTACTCGGTCTTTT<br>GCTTGGCATGGTTGGTACGGACGTAAATTCAGGTGTAGCGCGTTACTCATTTG<br>ACATTCCAGAGCTAACAGATGGTATTGATTTTGTTGTGATCGCAATGGGTGTT<br>TTTGGTTACGGTGAAATTATTGCAAATCTTTCAAAGCCTGATGATGAACGTGA<br>GGTTTTTGCAGCGAAAGTGACTGGTCTTCTTCCAACAAGTGAAGACTTCAAAC<br>GTATGTTGCCAGCAATGTTGCGTGGTACAGCATTAGGTTCAGCTTTAGGAATT<br>TTGCCAGGTGGTGGTGCTATGTTGAGTGCATTTGCAGCTTATACAATTGAAAA<br>AAAAACCAAATTAAAACCTGGTGAAGTACCATTTGGTCAGGGCAATATTCGTG<br>GCGTTTGCGCTCCGGAATCAGCAAACAACGCTGGTAGTCAAACATCTTTCATT<br>CCACTGTTAACATTGGGCATTCCTCCAAACGCCGTAATGGCTCTCATGGTAGG<br>CGCAATGACTATTCACAACATTCAACCAGGACCACAAGTGATGACATCTAACC<br>CTGAACTATTTTGGGGTCTTATTGCAAGCATGTGGATTGGTAATTTGATGTTA<br>ATTATTTTGAACCTACCACTTATCGGTGTGTGGATCAAGTTGCTTACAGTACC<br>ATATCGTTGGTTGTTTCCATCTATCGTATTATTTTGTGCAATTGGTGTGTATG<br>GTACTAATAACAACGTTTGGGATGTTTGGATGGTAGGTATTTTTGGTTTCATT<br>GGTTATGTATTCCACAAGTTAGGGACTGAACCTGCTCCTTTGTTGTTGGGTTT<br>CATTTTAGGTCCAATGATGGAAGAAAAACCTTCGCCGTGCTCTATTGCTATCGC<br>GTGGCGACTGGTCTGTATTTGTTACGCGTCCAATTAGTGCATGCTTACTGGCA<br>GCGGCTGTTGTGCTTCTTGTAATCGTTCTTATGCCTGCAGTTAAGAATAAACG<br>TGAAGAGGCCTTTGTAGAAGATtga<i>CTCGAGGACGAGGCGCATAC</i>atgGCTAA<br>AATGAGAATATCACC |

Strain Construction:

Chromosomal modifications were engineered in *A. baylyi* by natural transformation of recipient strains with linear DNA fragments. These DNA fragments were obtained by PCR or from restriction enzyme digestion of plasmids. To increase transformation efficiency, cells were grown in MMP instead of LB broth. To facilitate efficient homologous recombination, the transforming DNA carried 1-2 kbp of sequence that was identical to the chromosomal target on each side of the mutated region. *A. baylyi* mutants were selected on MMP plates with the appropriate antibiotic, or on YT+25% sucrose (10 g/L yeast extract, 20 g/L tryptone, 250 g/L sucrose, and 18 g/L agar) in the case of sacB counterselection. Genotypes were confirmed by colony PCR with MyTaq HS Red Mix (Bioline) and, in some cases, Sanger sequencing of localized regions. A brief description of the strains used in this study is provided in Table 3 and FIG. 7. Details on strain construction can be found in Table 8.

TABLE 8

*A. balylyi* strains, isolates and lineages used in this study. ADP1-derived strains constructed during the stepwise integration of tph and tpi genes (see FIG. S1) and strains expressing tph genes from a single copy are IP101, IP103, IP115, IP130, and IP148. ADP1-derived strains expressing different alleles of the TPA-TTT from *Comamonas* sp. E6 are IP297, IP313, IP337, AND IP348. IP148-derived dcaS and mucK mutants are IP367, IP378, IP387, IP398, IP400, IP402, IP411, IP413, IP415, IP417, and IP419. ADP1-derived dcaS and mucK mutants are IP461, and IP492-IP499. IP148-derived Tpa$^+$ isolates and lineages expressing tph genes from multiple copies are the remainder in the table starting with TPA_1. For the purpose of standardized nomenclature, tphA genes are numbered in subscript to differentiate them from mutated alleles.

| Identifier | Relevant characteristics | Construction details |
| --- | --- | --- |
| | Strains | |
| ADP1 | Wild type | |
| IP101 | poBA:P$_{tac}$:tphCA$_2$:Km$^R$:sacB | P$_{tac}$:tphCA$_2$ with upstream targeting region was amplified from pIP021 with oIP096 + oIP145. Km$^R$:sacB cassette was amplified from pCJ050 with oIP001 + oIP002. Downstream targeting region was amplified from pIP021 with oIP146 + oIP018. Fragments were assembled by SOE PCR and transformed into ADP1 for integration between pobA and hcaG loci. |
| IP103 | pobA:P$_{tac}$:tphCA$_2$A$_3$BA$_1$ | tphA$_2$A$_3$BA$_1$ and downstream targeting region were amplified from pIP021 with oIP103 + oIP147 and oIP148 + oIP018. Fragments were assembled by SOE PCR and integrated into IP101. |
| IP115 | pobA:P$_{tac}$:tphCA$_2$A$_3$BA$_1$:tpiBA:ΩKm$^R$ | TphA$_1$:ΩKmR with downstream targeting region was amplified from pIP024 with oIP106 + oIP018 and integrated into IP103. |
| IP130 | pobA:P$_{tac}$:tphCA$_2$A$_3$BA$_1$:tpiBA:ΩKm$^R$ | tpiBA:ΩKm$^R$ fragment with synthetic RBS sequences, flanked by targeting regions, was amplified from pIP032 with oIP106 + oIP108 and integrated into IP103. |
| IP148 | pobA:P$_{tac}$:tphCA$_2$A$_3$BA$_1$:P$_{trc}$:tpiBA1481:tpiA1482 [tpiA1481 encodes TpiA(W366*); tpiA1482 encodes TpiA(Δ1-370)]; rpoD148 [encodes RpoD(A87E)[ | ΩKm$^R$:p$_{trc}$:tpiBA with synthetic RBS sequences, flanked by targeting regions arm, was amplified from pIP041 with oIP106 + oIP018 and integrated into IP103. |
| IP297 | pobA:P$_{tac}$:tphC:ΩKm$^R$:P$_{trc}$:tpiBA1481 | P$_{tac}$:tphC:ΩKm$^R$:P$_{trc}$:tpiBA1481 flanked by targeting regions was amplified from pIP075 with oIP018 + oIP096 and integrated into ADP1. |
| IP313 | pobA:P$_{tac}$:tphC:ΩKm$^R$:P$_{trc}$:tpiBA | P$_{tac}$:tphC:ΩKm$^R$:P$_{trc}$:tpiBA flanked by targeting regions was excised from pIP073 with PmeI digestion and integrated into ADP1. |
| IP337 | pobA:P$_{tac}$:tphC:ΩKm$^R$:P$_{trc}$:tpiBA1481:tpiA1482; rpoD148 | A Sm$^R$:sacB cassette, flanked by targeting regions, was excised from pIP089 with SmaI + SalI and transformed into IP148 to replace tphA$_2$A$_3$BA$_1$:ΩKm$^R$. The resulting strain was then transformed with a ΩKm$^R$ cassette flanked by targeting regions, amplified from pIP073 with oIP102 + oIP347, to replace SmR:sacB. |
| IP348 | pobA:P$_{tac}$:tphC:ΩKm$^R$:P$_{trc}$:tpiBA1481:tpiA1482 | P$_{tac}$:tphC:ΩKm$^R$:P$_{trc}$:tpiBA$^{W366*}$, flanked by targeting regions, was amplified from IP337 gDNA with oIP018 + oIP096 and integrated into ADP1. |
| IP367 | pobA:P$_{tac}$:tphCA$_2$A$_3$BA$_1$:ΩKm$^R$:P$_{trc}$:tpiBA1481:tpiA1482; ΔmucK::Sm$^R$:sacB; rpoD148 | Sm$^R$:sacB cassette flanked by targeting regions for mucK replacement was excised from pIP103 with BamHI + EcoRV and integrated into IP148. |
| IP378 | pobA:P$_{tac}$:tphCA$_2$A$_3$BA$_1$:ΩKm$^R$:P$_{trc}$:tpiBA1481:tpiA1482; ΔdcaS; rpoD148 | Sm$^R$:sacB flanked by targeting regions for dcaS replacement was excised from pIP102 with BamHI + HindIII and integrated into IP148. The resulting strain was then transformed with fused upstream and downstream targeting regions, excised from pIP104 with BamHI + HindIII. |

TABLE 8-continued

*A. balylyi* strains, isolates and lineages used in this study. ADP1-derived strains constructed during the stepwise integration of tph and tpi genes (see FIG. S1) and strains expressing tph genes from a single copy are IP101, IP103, IP115, IP130, and IP148. ADP1-derived strains expressing different alleles of the TPA-TTT from *Comamonas* sp. E6 are IP297, IP313, IP337, AND IP348. IP148-derived dcaS and mucK mutants are IP367, IP378, IP387, IP398, IP400, IP402, IP411, IP413, IP415, IP417, and IP419. ADP1-derived dcaS and mucK mutants are IP461, and IP492-IP499. IP148-derived Tpa+ isolates and lineages expressing tph genes from multiple copies are the remainder in the table starting with TPA_1. For the purpose of standardized nomenclature, tphA genes are numbered in subscript to differentiate them from mutated alleles.

| Identifier | Relevant characteristics | Construction details |
| --- | --- | --- |
| IP387 | pobA:$P_{tac}$:tphCA$_2$A$_3$BA$_1$:ΩKm$^R$:P$_{trc}$:tpiBA1481:tpiA1482; ΔdcaS; ΔmucK::Sm$^R$:sacB; rpoD148 | Sm$^R$:sacB cassette flanked by targeting regions for mucK replacement was excised from pIP103 with BamHI + EcoRV and integrated into IP378. |
| IP398 | pobA:$P_{tac}$:tphCA$_2$A$_3$BA$_1$:ΩKm$^R$:P$_{trc}$:tpiBA1481:tpiA1482; ΔmucK::mucK258 [encodes MucK(M34I E53G)]; rpoD148 | mucK258 flanked by targeting regions was excised from pIP105 with BamHI + EcoRV and integrated into IP367. |
| IP400 | pobA:$P_{tac}$:tphCA$_2$A$_3$BA$_1$:ΩKm$^R$:P$_{trc}$:tpiBA1481:tpiA1482; ΔmucK::mucK243 [encodes MucK(M34L T342I)]; rpoD148 | mucK243 flanked by targeting regions was excised from pIP106 with BamHI + EcoRV and integrated into IP367. |
| IP402 | pobA:$P_{tac}$:tphCA$_2$A$_3$BA$_1$:ΩKm$^R$:P$_{trc}$:tpiBA1481:tpiA1482; ΔmucK::mucK255 [encodes MucK(W150C I403T)]; rpoD148 | mucK255 flanked by targeting regions was excised from pIP107 with BamHI + EcoRV and integrated into IP367. |
| IP411 | pobA:$P_{tac}$:tphCA$_2$A$_3$BA$_1$:ΩKm$^R$:P$_{trc}$:tpiBA1481:tpiA1482; ΔmucK::mucK246 [encodes MucK(Y133C)]; rpoD148 | mucK246 flanked by targeting regions was excised from pIP108 with BamHI + EcoRV and integrated into IP367. |
| IP413 | pobA:$P_{tac}$:tphCA$_2$A$_3$BA$_1$:ΩKm$^R$:P$_{trc}$:tpiBA1481:tpiA1482; ΔdcaS; ΔmucK::mucK258; rpoD148 | mucK258 flanked by targeting regions was excised from pIP105 with BamHI + EcoRV and integrated into IP387. |
| IP415 | pobA:$P_{tac}$:tphCA$_2$A$_3$BA$_1$:ΩKm$^R$:P$_{trc}$:tpiBA1481:tpiA1482; ΔdcaS; ΔmucK::mucK243; rpoD148 | mucK243 flanked by targeting regions was excised from pIP106 with BamHI + EcoRV and integrated into IP387. |
| IP417 | pobA:$P_{tac}$:tphCA$_2$A$_3$BA$_1$:ΩKm$^R$:P$_{trc}$:tpiBA1481:tpiA1482; ΔdcaS; ΔmucK::mucK258; rpoD148 | mucK255 flanked by targeting regions was excised from pIP107 with BamHI + EcoRV and integrated into IP387. |
| IP419 | pobA:$P_{tac}$:tphCA$_2$A$_3$BA$_1$:ΩKm$^R$:P$_{trc}$:tpiBA1481:tpiA1482; ΔdcaS; ΔmucK::mucK258; rpoD148 | mucK246 flanked by targeting regions was excised from pIP108 with BamHI + EcoRV and integrated into IP387. |
| IP461 | ΔdcaS | Sm$^R$:sacB flanked by targeting regions for dcaS replacement was excised from pIP102 with BamHI + HindIII and integrated into wild-type ADP1. The resulting strain was then transformed with fused upstream and downstream targeting regions, excised from pIP104 with BamHI + HindIII. |
| IP492 | ΔmucK::mucK258 | Sm$^R$:sacB flanked by targeting regions for mucK replacement was excised from pIP103 with BamHI + EcoRV and integrated into wild-type ADP1. The resulting strain was then transformed with mucK variant M34I E53G flanked by targeting regions, excised from pIP105 with BamHI + EcoRV. |
| IP493 | ΔmucK::mucK243 | Sm$^R$:sacB flanked by targeting regions for mucK replacement was excised from pIP103 with BamHI + EcoRV and integrated into wild-type ADP1. The resulting strain was then transformed with mucK variant M34L T342I flanked by targeting regions, excised from pIP106 with BamHI + EcoRV. |
| IP494 | ΔmucK::mucK255 | Sm$^R$:sacB flanked by targeting regions for mucK replacement was excised from pIP103 with BamHI + EcoRV and integrated into wild-type ADP1. The resulting strain was then transformed with mucK variant W150C I403T flanked by targeting regions, excised from pIP107 with BamHI + EcoRV. |
| IP495 | ΔmucK::mucK246 | Sm$^R$:sacB flanked by targeting regions for mucK replacement was excised from pIP103 with BamHI + EcoRV and integrated into wild-type ADP1. The resulting strain was then transformed with mucK variant Y133C flanked by targeting regions, excised from pIP108 with BamHI + EcoRV. |
| IP496 | ΔdcaS ΔmucK::mucK258 | Sm$^R$:sacB flanked by targeting regions for mucK replacement was excised from pIP103 with BamHI + EcoRV and integrated into IP461. The resulting strain was then transformed with mucK258 flanked by targeting regions, excised from pIP105 with BamHI + EcoRV. |

TABLE 8-continued

*A. balylyi* strains, isolates and lineages used in this study. ADP1-derived strains constructed during the stepwise integration of tph and tpi genes (see FIG. S1) and strains expressing tph genes from a single copy are IP101, IP103, IP115, IP130, and IP148. ADP1-derived strains expressing different alleles of the TPA-TTT from *Comamonas* sp. E6 are IP297, IP313, IP337, AND IP348. IP148-derived dcaS and mucK mutants are IP367, IP378, IP387, IP398, IP400, IP402, IP411, IP413, IP415, IP417, and IP419. ADP1-derived dcaS and mucK mutants are IP461, and IP492-IP499. IP148-derived Tpa+ isolates and lineages expressing tph genes from multiple copies are the remainder in the table starting with TPA_1. For the purpose of standardized nomenclature, tphA genes are numbered in subscript to differentiate them from mutated alleles.

| Identifier | Relevant characteristics | Construction details |
|---|---|---|
| IP497 | ΔdcaS ΔmucK::mucK243 | $Sm^R$:sacB flanked by targeting regions for mucK replacement was excised from pIP103 with BamHI + EcoRV and integrated into IP461. The resulting strain was then transformed with mucK243 flanked by targeting regions, excised from pIP106 with BamHI + EcoRV. |
| IP498 | ΔdcaS ΔmucK::mucK255 | $Sm^R$:sacB flanked by targeting regions for mucK replacement was excised from pIP103 with BamHI + EcoRV and integrated into IP461. The resulting strain was then transformed with mucK255 flanked by targeting regions, excised from pIP107 with BamHI + EcoRV. |
| IP499 | ΔdcaS ΔmucK::mucK246 | $Sm^R$:sacB flanked by targeting regions for mucK replacement was excised from pIP103 with BamHI + EcoRV and integrated into IP461. The resulting strain was then transformed with mucK246 flanked by targeting regions, excised from pIP108 with BamHI + EcoRV. |
| Tpa+ isolates and ALE lineages with (multiple copies of tph genes) | | |
| TPA_1 | pobA:[$P_{tac}$:tphCA$_2$A$_3$BA$_1$:ΩKm$^R$]$_n$; $P_{trc}$:tpiBA1481:tpiA1482; rpoD148 | IP148 transformed with SBF. Tpa+ isolate 1. |
| TPA_2 | pobA:[$P_{tac}$:tphCA$_2$A$_3$BA$_1$:ΩKm$^R$]$_n$; $P_{trc}$:tpiBA1481:tpiA1482; rpoD148 | IP148 transformed with SBF. Tpa+ isolate 2. |
| TPA_3 | pobA:[$P_{tac}$:tphCA$_2$A$_3$BA$_1$:ΩKm$^R$]$_n$; $P_{trc}$:tpiBA1481:tpiA1482; rpoD148 | IP148 transformed with SBF. Tpa+ isolate 3. |
| TPA_4 | pobA:[$P_{tac}$:tphCA$_2$A$_3$BA$_1$:ΩKm$^R$]$_n$; $P_{trc}$:tpiBA1481:tpiA1482; rpoD148 | IP148 transformed with SBF. Tpa+ isolate 4. |
| IP243 | pobA:[$P_{tac}$:tphCA$_2$A$_3$BA$_1$:ΩKm$^R$]$_n$; $P_{trc}$:tpiBA1481:tpiA1482; dcaS243 [encodes DcaS(V101G)]; mucK243; rpoD148 | Evolved isolate from lineage TPA_1.6. See supplementary Excel file for complete genotype. |
| IP246 | pobA:[$P_{tac}$:tphCA$_2$A$_3$BA$_1$:ΩKm$^R$]$_n$; $P_{trc}$:tpiBA1481:tpiA1482; dcaS246 [encodes DcaS(V101G A134E)]; mucK243 | Evolved isolate from population TPA_1.7. See supplementary Excel file for complete genotype. |
| IP247 | pobA:[$P_{tac}$:tphCA$_2$A$_3$BA$_1$:ΩKm$^R$]$_n$; $P_{trc}$:tpiBA1481:tpiA1482; gudP247 [encodes GudP(R289C)]; gud-247 (ACIAD_RS00620 encodes FadR-family transcription regulator potentially lacking residues 152-237); rpoD148 | Evolved isolate from population TPA_2.6. See supplementary Excel file for complete genotype. |
| IP250 | pobA:[$P_{tac}$:tphCA$_2$A$_3$BA$_1$:ΩKm$^R$]$_n$; $P_{trc}$:tpiBA1481:tpiA1482; gudP250 [encodes R447L]; gud-247; rpoD148 | Evolved isolate from population TPA_2.7. See supplementary Excel file for complete genotype. |
| IP251 | pobA:[$P_{tac}$:tphCA$_2$A$_3$BA$_1$:ΩKm$^R$]$_n$; $P_{trc}$:tpiBA1481:tpiA1482; ~60 kpb amplicon from ACIAD_RS07670 to ACIAD_RS07925; rpoD148 | Evolved isolate from population TPA_3.6. See supplementary Excel file for complete genotype. |
| IP254 | pobA:[$P_{tac}$:tphCA$_2$A$_3$BA$_1$:ΩKm$^R$]$_n$; $P_{trc}$:tpiBA1481:tpiA1482; ~60 kpb amplicon from ACIAD_RS07670 to ACIAD_RS07925; rpoD148 | Evolved isolate from population TPA_3.7. See supplementary Excel file for complete genotype. |
| IP255 | pobA:[$P_{tac}$:tphCA$_2$A$_3$BA$_1$:ΩKm$^R$]$_n$; $P_{trc}$:tpiBA1481:tpiA1482; dcaS255 [encodes DcaS(Δ169-282)]; mucK255; rpoD148 | Evolved isolate from population TPA_4.6. See supplementary Excel file for complete genotype. |
| IP258 | pobA:[$P_{tac}$:tphCA$_2$A$_3$BA$_1$:ΩKm$^R$]$_n$; $P_{trc}$:tpiBA1481:tpiA1482; dcaS255; mucK25; rpoD148 | Evolved isolate from population TPA_4.7. See supplementary Excel file for complete genotype. |

Chromosomal Gene Amplification and Adaptive Laboratory Evolution by EASy:

Chromosomal amplification was achieved by natural transformation of IP148 with a synthetic bridging fragment (SBF) and selecting on high-Km. The SBF defines the chromosomal region to be amplified and promotes duplication and further amplification through homologous recombination. For the construction of a SBF, the first and last ~1000 bp of the synthetic $P_{tac}$:tphCA2A3BA1:Δ Km$^R$ cassette were amplified by PCR and fused tail-to-head by overlap extension PCR. The resulting ~2 kbp SBF was transformed into strain IP148 and mutants with increased gene copy number were selected on MMP plates supplemented with 1 mg/mL Km. Growth on high-Km is presumably due to multiple copies of the Km$^R$ gene, resulting from the chromosomal amplification of a region encompassing it. This region (the amplicon) also encompasses the genes needed for TPA consumption. Individual colonies confirmed by colony PCR to have integrated the SBF were re-streaked on a new high-Km plate and grown at 30° C. By scraping cells from the high-Km plate and streaking on a MM plate with 5 mM TPA as the carbon source (and no antibiotic pressure), selection for optimal copy number of the tandemly arrayed amplicon is altered, and changes in gene dosage can thereby enable the new phenotype, i.e. growth on TPA (Tpa+). In this fashion, four Tpa+ colony isolates, designated TPA_1 to TPA_4, were selected and confirmed to contain the SBF by colony PCR.

After growth on a second TPA plate, each isolate was used in adaptive laboratory evolution (ALE) conducted by serial transfer in MM with 5 or 10 mM TPA as the carbon source. Each isolate was evolved at pH 6 and pH 7 in parallel (8 lineages in total). Two-mL cultures (in 13 mm test tubes) were grown at 30° C. with shaking (225 rpm). When cultures reached stationary phase, cells were diluted 100 or 200-fold in 2 mL of fresh medium. Weekly, glycerol stocks were prepared, and genomic DNA from each culture was extracted with the Quick-DNA Miniprep Plus kit (Zymo Research) for quantitation of the average gene copy number.

Gene Copy Number Analysis by Quantitative PCR:

Quantitative PCR (qPCR) was carried out using 6FAM-MGBNFQ labelled TaqMan probes and TaqMan Gene Expression Master Mix (Thermo Scientific) in a Bio-Rad CFX96 thermocycler. Primer and probe sequences are provided in Table 9. To evaluate changes in amplicon copy number during ALE, relative amounts of the $Km^R$ gene were calculated with respect to rpoA, as previously described. For spontaneous amplification mutants not obtained by transformation with the SBF, primers and a probe specific for the synthetic $tphA_2$ gene were used. All reactions were carried out with four technical replicates per genomic DNA sample, with single-copy parent strain IP148 included as control.

300-500 bp. End repair, A-tailing, and adapter ligation reactions were performed on the fragmented DNA using the NEBNext Ultra II kit (New England Biolabs). Illumina paired-end sequencing was performed on a NextSeq500 device at the Georgia Genomics Facility (University of Georgia). Sequence analysis and variant calling (minimal frequency set at 0.25) was performed with Geneious Prime software against the theoretical genome sequence of IP148 parent strain and a modified sequence presenting two copies of the amplicon. The wild-type ADP1 genome sequence (National Center for Biotechnology Information accession number NC_005966) was used as reference.

Evaluation of Growth and TPA Consumption by Cultures Grown in Microtiter Plates and Shake-Flasks:

To evaluate growth of *A. baylyi* mutants, cultures in microtiter plates were analyzed with a Bioscreen C MBR plate-reader (Growth Curves USA). Cells for inoculation were grown overnight in MMP at 30° C. and 225 rpm. After collection by centrifugation, cells were washed with MM (no carbon source) and added to 300 μL media to an $OD_{600}$ of 0.05 (per well). Cells were incubated at 30° C. with shaking and $OD_{420-580}$ measured at 15-minute intervals.

For shake-flask cultures, cells for inoculation were grown overnight in MMP (*A. baylyi*) or LB broth (*Comamonas* sp. E6 and *R. jostii* RHA1) at 30° C. and 225 rpm. After collection by centrifugation, cells were washed with MM (no carbon source). For wild-type ADP1 and single-copy mutants, cells were inoculated to an $OD_{600}$ of 0.02 in 25 mL MMP supplemented with 5 mM TPA (pH 6 and 7) in 125-mL flasks. For Tpa+ *A. baylyi* mutants, *Comamonas* sp. E6, and *R. jostii* RHA1, cells were inoculated to an $OD_{600}$ of 0.02 in 50 mL MM with 10 mM TPA (pH 6 or 7) in

TABLE 9

Sequences for primers and probes used for quantitative PCR (qPCR).

| SEQ ID NO | Oligo ID | Sequence | Description |
| --- | --- | --- | --- |
| SEQ ID NO: 110 | oIP082 | gctcgacgccttctatttcaa | rpoA qPCR forward primer |
| SEQ ID NO: 111 | oIP083 | tttacgtcgcattctattgtcttctt | rpoA qPCR reverse primer |
| SEQ ID NO: 112 | qIP004 | tcaaccacagcagcgccaggc | rpoA 6FAM-MGBNFQ qPCR probe |
| SEQ ID NO: 113 | oIP141 | gcgttggctacccgtgata | $Km^R$ qPCR forward primer |
| SEQ ID NO: 114 | oIP142 | ggaagcggtcagcccatt | $Km^R$ qPCR reverse primer |
| SEQ ID NO: 115 | qIP005 | tgaagagcttggcggc | $Km^R$ 6FAM-MGBNFQ qPCR probe |
| SEQ ID NO: 116 | oIP456 | tggacctgctggattcatttc | $tphA_2$ qPCR forward primer |
| SEQ ID NO: 117 | oIP457 | tcaccgcccatttcgattac | $tphA_2$ qPCR reverse primer |
| SEQ ID NO: 118 | qIP006 | ctgcaataccacgctgcacgaaac | $tphA_2$ 6FAM-MGBNFQ qPCR probe |
| SEQ ID NO: 119 | oIP484 | attcggccatgagggtattg | mucK qPCR forward primer |
| SEQ ID NO: 120 | oIP485 | ccttggattgactcagagcttta | mucK qPCR reverse primer |
| SEQ ID NO: 121 | qIP007 | acctaaaccgagtgaagcgaagaaacg | mucK 6FAM-MGBNFQ qPCR probe |

Whole-Genome Sequencing and Variant Analysis:

After ~750 generations of ALE, cells from each individual lineage were diluted $10^7$-fold and 100 μL plated on MM agar with 5 mM TPA. Two individual colonies from each lineage were selected and the amplicon copy number verified by qPCR. The clone with the lowest copy number from each lineage was selected for whole-genome sequencing and phenotypic characterization. Approximately 1 μg of genomic DNA was fragmented by sonication to an average size of 250-mL flasks. In all cases, cells were grown at 30° C., 225 rpm, and sampled regularly by removing 1 mL aliquots for $OD_{600}$ measurements and HPLC analysis. Standard curves were made to correlate cell dry weight to $OD_{600}$ for strains *A. baylyi* IP148, *Comamonas* sp. E6, and *R. jostii* RHA1.

HPLC analysis: HPLC analysis of samples was performed on an Agilent 1260 LC system (Agilent Technologies) equipped with a G7117C diode array detector (DAD). All samples and standards were injected at a volume of 10 μL onto a Phenomenex Luna C18(2), 5 μm, 4.6×150 mm column. The column temperature was maintained at 30° C. and the buffers used to separate the analytes of interest were (A) 20 mM phosphate buffer in water and (B) methanol. The separation was carried out using a gradient program of: (A)=80% and (B)=20% at time t=0; (A)=35% and (B)=65% at time t=15 min; and (A)=80% and (B)=20% at t=15.01 min through 20 min. The flow rate was held constant at 0.6 mL/min for a total run time of 20 min. DAD wavelength of 240 nm was used for analysis of TPA while pyruvic acid signal was collected at 210 nm. Calibration curve concentration for each analyte varied between the ranges of 0.1-2500 μg/L. A minimum of 5-6 calibration levels was used with an R2 coefficient of 0.995 or better for each analyte. A check calibration standard was analyzed every 10-20 samples to ensure the integrity of the initial calibration.

Transformation of Biosensor Plasmid Libraries into *A. baylyi*:

For the transformation of biosensor plasmid libraries, the natural transformation protocol was used, with slight modifications. *A. baylyi* cultures were started from glycerol stocks in 1 mL MMP and grown overnight at 30° C. under constant shaking. A small volume of the overnight culture (70 μL) was then added to 1 mL fresh MMP and mixed with ~100 ng of plasmid DNA. The cells were incubated at 30° C. under constant shaking for 2-6 h, spun down at 5000 rpm for 3 minutes in a tabletop centrifuge at ambient temperature, and the concentrated pellet plated on MMP+Sm. In order to cover a large library diversity, overnight cells were concentrated 10-fold. Then, 70 μL of the concentrated cells were mixed with up to 300 ng of plasmid DNA in 1 mL MMP and incubated as described above. Multiple parallel transformations were carried out for larger libraries. Plates were incubated overnight at 30° C. Colonies from plates were then scraped and resuspended in 2 mL of liquid media, rotated gently for 15 minutes for homogeneity, and subsequently saved as glycerol stocks.

Flow Cytometry and Cell Sorting:

*A. baylyi* mutants transformed with biosensor plasmid libraries were pooled by scraping from plates and diluted to an $OD_{600}$ of ~0.05. After growth for 2-4 hours, TPA was added at various concentrations (in the range of 0-3 mM) to induce expression of the sfGFP gene. The cultures were grown overnight at 30° C. and analyzed by fluorescence-activated cell sorting (FACS) on a FACSAria III flow cytometer (BD Biosciences), using the standard settings for GFP fluorescence (488 nm excitation laser and 530/30 nm bandpass emission filter). The cells were gated based on forward and side light scatter (FSC/SSC). Based on the theoretical diversity of the libraries, two to three rounds of sorting were performed. These rounds consisted of positive (top 1-3% fluorescent cells from an induced population) and negative (bottom 50-80% low fluorescent cells from an uninduced population) cell sorting. In any round of sorting, 25-50 thousand cells were collected. Finally, the sorted cells were grown on MMP+Sm plates and colonies picked for individual clone verification.

Individual colonies were inoculated into 600 μL of MMP in a 96 deep-well v-bottom plate (Agilent) and grown for 6 hours at 30° C. and 1000 rpm in a deep-well maximizer shaker (Taitec Bioshaker MBR-022UP). The cultures were then split into replicate wells, after which one of the two sets was provided with 0.3 mM TPA to induce expression of the sfGFP gene. After overnight growth, cells were diluted 20- to 50-fold in phosphate buffer saline (PBS) and analyzed on an Accuri C6 flow cytometer (BD Biosciences) under the standard settings for GFP measurements (excitation 488 nm and emission 533/30 nm). The cells were gated based on FSC/SSC, and the clones with the highest contrast ratios (induced/uninduced fluorescence response) were selected for further evaluation.

Dose Response and Specificity Testing of the TPA Sensor:

*A. baylyi* mutants were transformed with selected plasmids and grown on MMP+Sm plates. Three colonies were picked and grown overnight as seed cultures. These cultures were diluted 50-fold into 10 mL MMP+Sm and grown for 2-4 h in a 50-mL conical tube to an $OD_{600}$ of ~0.6. The culture was then split into triplicate wells in a 96 deep-well v-bottom plate. Into each well (containing 270 μL of culture), 30 μL of 10× stock solutions of possible inducers of sfGFP gene expression were added (in the range of 0-100 mM for each). Cultures were grown overnight and analyzed using an Accuri C6 flow cytometer (BD Biosciences), following the protocol described above.

Evaluation of TPA Transport in *A. baylyi* with the TPA Sensor:

*A. baylyi* mutants were naturally transformed with plasmids encoding the TPA biosensors. After selection on MMP+Sm plates, transformants were grown overnight in the same medium at 30° C. with shaking, collected by centrifugation, and washed with MM. Cells were then used to inoculate, to an $OD_{600}$ of 0.05, 200 μL of medium per well of 96-well black, clear flat-bottom plates (Corning). Cultures contained MMP+Sm with varied concentrations of TPA. Plates were incubated at 30° C. with shaking in an Infinite® F500 Tecan plate reader for 24 hours. The $OD_{600}$ and fluorescence at 520 nm (excitation at 488 nm) were measured at 15-minute intervals. The gain used for fluorescence reads was adjusted manually.

Gene Expression Analysis by Reverse Transcriptase-Quantitative PCR (RT-qPCR):

Wild-type ADP1 and Δ dcaS mutant IP461 were grown overnight in MMP at 30° C., 225 rpm. Cells were harvested by centrifugation, washed with MM, and inoculated in triplicate to an $OD_{600}$ of 0.1 in 25 mL MM with either 20 mM pyruvate, 5 mM muconate, or 5 mM PCA as the carbon source, in 125-mL flasks. Cells were grown at 30° C., 225 rpm, to an $OD_{600}$ of ~0.6, after which cells were harvested by centrifugation, flash-frozen in liquid nitrogen, and stored at −80° C. For RNA extraction, cells were lysed by bead-beating and RNA purified with a QIAGEN RNeasy Mini kit. Genomic DNA was digested with a TURBO DNA-free kit (Thermo Scientific) and cDNA was synthesized with iScript Reverse Transcription Supermix using random primers (Bio-Rad). qPCR was performed in triplicate for each biological sample with 6FAM-MGBNFQ labelled TaqMan probes and TaqMan Gene Expression Master Mix (Thermo Scientific). Primer and probe sequences are provided in Table 9. Expression of mucK relative to rpoA was calculated using the $2^{-\Delta\Delta Ct}$ method.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A non-naturally occurring microorganism comprising:
a gene encoding a MucK transporter protein; and
a deletion of an endogenous gene encoding a transcriptional regulator, wherein:
the microorganism is capable of catabolizing terephthalic acid (TPA).

2. The non-naturally occurring microorganism of claim 1, wherein the gene encoding the MucK transporter protein contains at least one mutation, relative to a gene encoding a reference MucK transporter protein.

3. The non-naturally occurring microorganism of claim 2, wherein the reference MucK transporter protein is at least 90% identical to SEQ ID NO: 2.

4. The non-naturally occurring microorganism of claim 2, wherein the gene encoding the reference MucK transporter protein is at least 90% identical to SEQ ID NO: 1.

5. The non-naturally occurring microorganism of claim 1, wherein the mutation to the MucK transporter protein comprises at least one point mutation.

6. The non-naturally occurring microorganism of claim 5, wherein the point mutation is present at an amino acid located at at least one of positions 34, 53, 133, 341, or 342 on SEQ ID NO: 2.

7. The non-naturally occurring microorganism of claim 6, wherein the point mutation comprises at least one of M34L, M34I, Y133C, T342I, or E53G.

8. The non-naturally occurring microorganism of claim 1, further comprising a deletion of an endogenous gene encoding a MucK transporter protein.

9. The non-naturally occurring microorganism of claim 1, wherein the microorganism is further capable of growing on TPA.

10. The non-naturally occurring microorganism of claim 9, wherein the microorganism is characterized by a TPA consumption rate between greater than zero g TPA/L/hr and about 0.2 g/L/hr.

11. The non-naturally occurring microorganism of claim 9, wherein the microorganism is capable of growth in a liquid media at a temperature between about 25° C. and about 35° C.

12. The non-naturally occurring microorganism of claim 11, wherein the liquid media is maintained at pH between about 6 and about 7.

13. The non-naturally occurring microorganism of claim 1, wherein the microorganism comprises at least one of a bacterium, a yeast, or a fungus.

14. The non-naturally occurring microorganism of claim 13, wherein the microorganism is a bacterium.

15. The non-naturally occurring microorganism of claim 14, wherein the bacterium comprises a strain from at least one of *Acinetobacter baylyi, Pseudomonas putida, Pseudomonas fluorescens*, or *Pseudomonas stuzeri*.

16. The non-naturally occurring microorganism of claim 15, wherein the bacterium is *Acinetobacter baylyi*.

17. The non-naturally occurring microorganism of claim 16, wherein the bacterium is *Acinetobacter baylyi*.

18. The non-naturally occurring microorganism of claim 1, wherein the transcriptional regulator is a DcaS transcriptional regulator.

* * * * *

SEQUENCE LISTING

```
<160> NUMBER OF SEQ ID NOS: 121

<210> SEQ ID NO 1
<211> LENGTH: 1242
<212> TYPE: DNA
<213> ORGANISM: Acinetobacter baylyi

<400> SEQUENCE: 1
atgtacagca acaatcagag atccagaatt ggatcacaca catggaaaat tgctttttta      60
tttgcatttt tagcgttgct tgtggatgga gcagacctga tgttgctctc ttatagttta     120
aacagtatta aagctgagtt taatttaagt acagttgaag ctggaatgtt gggaagtttt     180
actttagctg gcatggcgat aggtggaatc tttggtgggt gggcgtgtga ccgatttggt     240
cgtgtacgca ttgttgtgat ttcaattctc acgttctcaa tcctaacgtg tggccttgga     300
ttgactcaga gctttataca atttggtgtt ttacgtttct tcgcttcact cggtttaggt     360
tctttatata ttgcctgcaa taccctcatg gccgaatatg ttccaacaaa ataccgtact     420
actgttttag gtacattaca ggctggctgg actgttggct atattgttgc caccttactg     480
gctggttggt taatacccga tcatggttgg cgtgtgctgt tttatgttgc gattattcct     540
gtacttatgg ctgtacttat gcattttttt gtaccagaac cagcagcatg gcaacaatca     600
cgcttagcac catccaaaca aactgaaaca gtcaaaactt ctgcctttaa attaatcttt     660
caagataaac gtaaccgtaa catgttcatt ctgtgggcac tcaccgcagg ctttctacaa     720
tttggttact atggcgtaaa caattggatg ccatcttatc ttgaaagtga attgggaatg     780
aagtttaagg aaatgacagc ctatatggtc ggaacataca ctgccatgat tttaggaaaa     840
atcttggctg cctttatggc tgataaactc ggccgtcgtt ttacttatgc atttggtgct     900
atcggaaccg caattttttt acctctaatc gtgttttata actcaccaga taatatttta     960
tatctattgg ttattttttgg tttcttgtac ggtattccat acggtgtcaa tgcaacttac    1020
atgacagaaa gcttcccaac agcaatacgt ggtacagcca ttggtggagc ttataatgta    1080
ggaagattag gcgcagcgat tgccccagca actattggtt ttctagcttc tggcggttca    1140
attggtttgg gctttgttgt aatgggagct gcatattta tttgtggtgt aattccagca    1200
ctgtttatca aagaaaaaca atatgatcca caacagtctt aa                        1242

<210> SEQ ID NO 2
<211> LENGTH: 413
<212> TYPE: PRT
<213> ORGANISM: Acinetobacter baylyi

<400> SEQUENCE: 2

Met Tyr Ser Asn Asn Gln Arg Ser Arg Ile Gly Ser His Thr Trp Lys
1               5                   10                  15

Ile Ala Phe Leu Phe Ala Phe Leu Ala Leu Leu Val Asp Gly Ala Asp
                20                  25                  30

Leu Met Leu Leu Ser Tyr Ser Leu Asn Ser Ile Lys Ala Glu Phe Asn
            35                  40                  45

Leu Ser Thr Val Glu Ala Gly Met Leu Gly Ser Phe Thr Leu Ala Gly
        50                  55                  60
```

| | | | | | | | | | | | | | | | |
|---|---|---|---|---|---|---|---|---|---|---|---|---|---|---|---|
| Met | Ala | Ile | Gly | Gly | Ile | Phe | Gly | Gly | Trp | Ala | Cys | Asp | Arg | Phe | Gly |
| 65 | | | | 70 | | | | 75 | | | | | | | 80 |
| Arg | Val | Arg | Ile | Val | Val | Ile | Ser | Ile | Leu | Thr | Phe | Ser | Ile | Leu | Thr |
| | | | | 85 | | | | | 90 | | | | | 95 | |
| Cys | Gly | Leu | Gly | Leu | Thr | Gln | Ser | Phe | Ile | Gln | Phe | Val | Leu | Arg | |
| | | | 100 | | | | | 105 | | | | | 110 | | |
| Phe | Phe | Ala | Ser | Leu | Gly | Leu | Gly | Ser | Leu | Tyr | Ile | Ala | Cys | Asn | Thr |
| | | 115 | | | | | 120 | | | | | 125 | | | |
| Leu | Met | Ala | Glu | Tyr | Val | Pro | Thr | Lys | Tyr | Arg | Thr | Thr | Val | Leu | Gly |
| | 130 | | | | | 135 | | | | | 140 | | | | |
| Thr | Leu | Gln | Ala | Gly | Trp | Thr | Val | Gly | Tyr | Ile | Val | Ala | Thr | Leu | Leu |
| 145 | | | | | 150 | | | | | 155 | | | | | 160 |
| Ala | Gly | Trp | Leu | Ile | Pro | Asp | His | Gly | Trp | Arg | Val | Leu | Phe | Tyr | Val |
| | | | | 165 | | | | | 170 | | | | | 175 | |
| Ala | Ile | Ile | Pro | Val | Leu | Met | Ala | Val | Leu | Met | His | Phe | Phe | Val | Pro |
| | | | 180 | | | | | 185 | | | | | 190 | | |
| Glu | Pro | Ala | Ala | Trp | Gln | Gln | Ser | Arg | Leu | Ala | Pro | Ser | Lys | Gln | Thr |
| | | | 195 | | | | | 200 | | | | | 205 | | |
| Glu | Thr | Val | Lys | Thr | Ser | Ala | Phe | Lys | Leu | Ile | Phe | Gln | Asp | Lys | Arg |
| 210 | | | | | 215 | | | | | 220 | | | | | |
| Asn | Arg | Asn | Met | Phe | Ile | Leu | Trp | Ala | Leu | Thr | Ala | Gly | Phe | Leu | Gln |
| 225 | | | | 230 | | | | | 235 | | | | | | 240 |
| Phe | Gly | Tyr | Tyr | Gly | Val | Asn | Asn | Trp | Met | Pro | Ser | Tyr | Leu | Glu | Ser |
| | | | | 245 | | | | | 250 | | | | | 255 | |
| Glu | Leu | Gly | Met | Lys | Phe | Lys | Glu | Met | Thr | Ala | Tyr | Met | Val | Gly | Thr |
| | | | 260 | | | | | 265 | | | | | 270 | | |
| Tyr | Thr | Ala | Met | Ile | Leu | Gly | Lys | Ile | Leu | Ala | Gly | Phe | Met | Ala | Asp |
| | | 275 | | | | | 280 | | | | | 285 | | | |
| Lys | Leu | Gly | Arg | Arg | Phe | Thr | Tyr | Ala | Phe | Gly | Ala | Ile | Gly | Thr | Ala |
| | 290 | | | | | 295 | | | | | 300 | | | | |
| Ile | Phe | Leu | Pro | Leu | Ile | Val | Phe | Tyr | Asn | Ser | Pro | Asp | Asn | Ile | Leu |
| 305 | | | | | 310 | | | | | 315 | | | | | 320 |
| Tyr | Leu | Leu | Val | Ile | Phe | Gly | Phe | Leu | Tyr | Gly | Ile | Pro | Tyr | Gly | Val |
| | | | | 325 | | | | | 330 | | | | | 335 | |
| Asn | Ala | Thr | Tyr | Met | Thr | Glu | Ser | Phe | Pro | Thr | Ala | Ile | Arg | Gly | Thr |
| | | | 340 | | | | | 345 | | | | | 350 | | |
| Ala | Ile | Gly | Gly | Ala | Tyr | Asn | Val | Gly | Arg | Leu | Gly | Ala | Ala | Ile | Ala |
| | | 355 | | | | | 360 | | | | | 365 | | | |
| Pro | Ala | Thr | Ile | Gly | Phe | Leu | Ala | Ser | Gly | Gly | Ser | Ile | Gly | Leu | Gly |
| | 370 | | | | | 375 | | | | | 380 | | | | |
| Phe | Val | Val | Met | Gly | Ala | Ala | Tyr | Phe | Ile | Cys | Gly | Val | Ile | Pro | Ala |
| 385 | | | | | 390 | | | | | 395 | | | | | 400 |
| Leu | Phe | Ile | Lys | Glu | Lys | Gln | Tyr | Asp | Pro | Gln | Gln | Ser | | | |
| | | | | 405 | | | | | 410 | | | | | | |

<210> SEQ ID NO 3
<211> LENGTH: 1242
<212> TYPE: DNA
<213> ORGANISM: Artificial Sequence
<220> FEATURE:
<223> OTHER INFORMATION: nt sequence for mucK258

<400> SEQUENCE: 3

```
atgtacagca acaatcagag atccagaatt ggatcacaca catggaaaat tgcttttta      60
```

```
tttgcatttt tagcgttgct tgtggatgga gcagacctga tattgctctc ttatagttta    120
aacagtatta aagctgagtt taatttaagt acagttggag ctggaatgtt gggaagtttt    180
actttagctg gcatggcgat aggtggaatc tttggtgggt gggcgtgtga ccgatttggt    240
cgtgtacgca ttgttgtgat ttcaattctc acgttctcaa tcctaacgtg tggccttgga    300
ttgactcaga gctttataca atttggtgtt ttacgtttct tcgcttcact cggtttaggt    360
tctttatata ttgcctgcaa taccctcatg gccgaatatg ttccaacaaa ataccgtact    420
actgttttag gtacattaca ggctggctgg actgttggct atattgttgc caccttactg    480
gctggttggt taatacccga tcatggttgg cgtgtgctgt tttatgttgc gattattcct    540
gtacttatgg ctgtacttat gcattttttt gtaccagaac cagcagcatg gcaacaatca    600
cgcttagcac catccaaaca aactgaaaca gtcaaaactt ctgcctttaa attaatcttt    660
caagataaac gtaaccgtaa catgttcatt ctgtgggcac tcaccgcagg ctttctacaa    720
tttggttact atggcgtaaa caattggatg ccatcttatc ttgaaagtga attgggaatg    780
aagtttaagg aaatgacagc ctatatggtc ggaacataca ctgccatgat tttaggaaaa    840
atcttggctg gctttatggc tgataaactc ggccgtcgtt ttacttatgc atttggtgct    900
atcggaaccg caatttttt acctctaatc gtgttttata actcaccaga taatatttta    960
tatctattgg ttatttttgg tttcttgtac ggtattccat acggtgtcaa tgcaacttac   1020
atgacagaaa gcttcccaac agcaatacgt ggtacagcca ttggtggagc ttataatgta   1080
ggaagattag gcgcagcgat tgccccagca actattggtt ttctagcttc tggcggttca   1140
attggtttgg gctttgttgt aatgggagct gcatatttta tttgtggtgt aattccagca   1200
ctgtttatca agaaaaaaca atatgatcca caacagtctt aa                     1242
```

<210> SEQ ID NO 4
<211> LENGTH: 413
<212> TYPE: PRT
<213> ORGANISM: Artificial Sequence
<220> FEATURE:
<223> OTHER INFORMATION: aa sequence of mucK258

<400> SEQUENCE: 4

```
Met Tyr Ser Asn Asn Gln Arg Ser Arg Ile Gly Ser His Thr Trp Lys
1               5                   10                  15

Ile Ala Phe Leu Phe Ala Phe Leu Ala Leu Leu Val Asp Gly Ala Asp
            20                  25                  30

Leu Ile Leu Leu Ser Tyr Ser Leu Asn Ser Ile Lys Ala Glu Phe Asn
        35                  40                  45

Leu Ser Thr Val Gly Ala Gly Met Leu Gly Ser Phe Thr Leu Ala Gly
    50                  55                  60

Met Ala Ile Gly Gly Ile Phe Gly Gly Trp Ala Cys Asp Arg Phe Gly
65                  70                  75                  80

Arg Val Arg Ile Val Ile Ser Ile Leu Thr Phe Ser Ile Leu Thr
                85                  90                  95

Cys Gly Leu Gly Leu Thr Gln Ser Phe Ile Gln Phe Gly Val Leu Arg
            100                 105                 110

Phe Phe Ala Ser Leu Gly Leu Gly Ser Leu Tyr Ile Ala Cys Asn Thr
        115                 120                 125

Leu Met Ala Glu Tyr Val Pro Thr Lys Tyr Arg Thr Thr Val Leu Gly
    130                 135                 140

Thr Leu Gln Ala Gly Trp Thr Val Gly Tyr Ile Val Ala Thr Leu Leu
145                 150                 155                 160
```

```
Ala Gly Trp Leu Ile Pro Asp His Gly Trp Arg Val Leu Phe Tyr Val
                165                 170                 175
Ala Ile Ile Pro Val Leu Met Ala Val Leu Met His Phe Phe Val Pro
            180                 185                 190
Glu Pro Ala Ala Trp Gln Gln Ser Arg Leu Ala Pro Ser Lys Gln Thr
        195                 200                 205
Glu Thr Val Lys Thr Ser Ala Phe Lys Leu Ile Phe Gln Asp Lys Arg
    210                 215                 220
Asn Arg Asn Met Phe Ile Leu Trp Ala Leu Thr Ala Gly Phe Leu Gln
225                 230                 235                 240
Phe Gly Tyr Tyr Gly Val Asn Asn Trp Met Pro Ser Tyr Leu Glu Ser
                245                 250                 255
Glu Leu Gly Met Lys Phe Lys Glu Met Thr Ala Tyr Met Val Gly Thr
            260                 265                 270
Tyr Thr Ala Met Ile Leu Gly Lys Ile Leu Ala Gly Phe Met Ala Asp
        275                 280                 285
Lys Leu Gly Arg Arg Phe Thr Tyr Ala Phe Gly Ala Ile Gly Thr Ala
    290                 295                 300
Ile Phe Leu Pro Leu Ile Val Phe Tyr Asn Ser Pro Asp Asn Ile Leu
305                 310                 315                 320
Tyr Leu Leu Val Ile Phe Gly Phe Leu Tyr Gly Ile Pro Tyr Gly Val
                325                 330                 335
Asn Ala Thr Tyr Met Thr Glu Ser Phe Pro Thr Ala Ile Arg Gly Thr
            340                 345                 350
Ala Ile Gly Gly Ala Tyr Asn Val Gly Arg Leu Gly Ala Ala Ile Ala
        355                 360                 365
Pro Ala Thr Ile Gly Phe Leu Ala Ser Gly Gly Ser Ile Gly Leu Gly
    370                 375                 380
Phe Val Val Met Gly Ala Ala Tyr Phe Ile Cys Gly Val Ile Pro Ala
385                 390                 395                 400
Leu Phe Ile Lys Glu Lys Gln Tyr Asp Pro Gln Gln Ser
                405                 410

<210> SEQ ID NO 5
<211> LENGTH: 1242
<212> TYPE: DNA
<213> ORGANISM: Artificial Sequence
<220> FEATURE:
<223> OTHER INFORMATION: nt sequence for mucK243

<400> SEQUENCE: 5
atgtacagca acaatcagag atccagaatt ggatcacaca catggaaaat tgcttttta      60 tttgcatttt tagcgttgct tgtggatgga gcagacctgt tgttgctctc ttatagttta    120
aacagtatta agctgagtt taatttaagt acagttgaag ctggaatgtt gggaagtttt     180
actttagctg gcatggcgat aggtggaatc tttggtgggt gggcgtgtga ccgatttggt    240
cgtgtacgca ttgttgtgat ttcaattctc acgttctcaa tcctaacgtg tggccttgga    300
ttgactcaga gctttataca atttggtgtt ttacgtttct tcgcttcact cggtttaggt    360
tctttatata ttgcctgcaa taccctcatg gccgaatatg ttccaacaaa ataccgtact    420
actgttttag gtacattaca ggctggctgg actgttggct atattgttgc caccttactg    480
gctggttggt taatacccga tcatggttgg cgtgtgctgt tttatgttgc gattattcct    540
gtacttatgg ctgtacttat gcatttttt gtaccagaac cagcagcatg gcaacaatca    600
```

```
cgcttagcac catccaaaca aactgaaaca gtcaaaactt ctgcctttaa attaatcttt    660
caagataaac gtaaccgtaa catgttcatt ctgtgggcac tcaccgcagg ctttctacaa    720
tttggttact atggcgtaaa caattggatg ccatcttatc ttgaaagtga attgggaatg    780
aagtttaagg aaatgacagc ctatatggtc ggaacataca ctgccatgat tttaggaaaa    840
atcttggctg gctttatggc tgataaactc ggccgtcgtt ttacttatgc atttggtgct    900
atcggaaccg caattttttt acctctaatc gtgttttata actcaccaga taatatttta    960
tatctattgg ttattttttgg tttcttgtac ggtattccat acggtgtcaa tgcaacttac   1020
atgatagaaa gcttcccaac agcaatacgt ggtacagcca ttggtggagc ttataatgta   1080
ggaagattag gcgcagcgat tgccccagca actattggtt ttctagcttc tggcggttca   1140
attggtttgg gctttgttgt aatgggagct gcatatttta tttgtggtgt aattccagca   1200
ctgtttatca aagaaaaaca atatgatcca caacagtctt aa                      1242
```

<210> SEQ ID NO 6
<211> LENGTH: 413
<212> TYPE: PRT
<213> ORGANISM: Artificial Sequence
<220> FEATURE:
<223> OTHER INFORMATION: aa sequence for mucK243

<400> SEQUENCE: 6

```
Met Tyr Ser Asn Asn Gln Arg Ser Arg Ile Gly Ser His Thr Trp Lys
1               5                   10                  15

Ile Ala Phe Leu Phe Ala Phe Leu Ala Leu Leu Val Asp Gly Ala Asp
            20                  25                  30

Leu Leu Leu Leu Ser Tyr Ser Leu Asn Ser Ile Lys Ala Glu Phe Asn
        35                  40                  45

Leu Ser Thr Val Glu Ala Gly Met Leu Gly Ser Phe Thr Leu Ala Gly
    50                  55                  60

Met Ala Ile Gly Gly Ile Phe Gly Gly Trp Ala Cys Asp Arg Phe Gly
65                  70                  75                  80

Arg Val Arg Ile Val Ile Ser Ile Leu Thr Phe Ser Ile Leu Thr
                85                  90                  95

Cys Gly Leu Gly Leu Thr Gln Ser Phe Ile Gln Phe Gly Val Leu Arg
            100                 105                 110

Phe Phe Ala Ser Leu Gly Leu Gly Ser Leu Tyr Ile Ala Cys Asn Thr
        115                 120                 125

Leu Met Ala Glu Tyr Val Pro Thr Lys Tyr Arg Thr Thr Val Leu Gly
    130                 135                 140

Thr Leu Gln Ala Gly Trp Thr Val Gly Tyr Ile Val Ala Thr Leu Leu
145                 150                 155                 160

Ala Gly Trp Leu Ile Pro Asp His Gly Trp Arg Val Leu Phe Tyr Val
                165                 170                 175

Ala Ile Ile Pro Val Leu Met Ala Val Leu Met His Phe Phe Val Pro
            180                 185                 190

Glu Pro Ala Ala Trp Gln Gln Ser Arg Leu Ala Pro Ser Lys Gln Thr
        195                 200                 205

Glu Thr Val Lys Thr Ser Ala Phe Lys Leu Ile Phe Gln Asp Lys Arg
    210                 215                 220

Asn Arg Asn Met Phe Ile Leu Trp Ala Leu Thr Ala Gly Phe Leu Gln
225                 230                 235                 240

Phe Gly Tyr Tyr Gly Val Asn Asn Trp Met Pro Ser Tyr Leu Glu Ser
                245                 250                 255
```

Glu Leu Gly Met Lys Phe Lys Glu Met Thr Ala Tyr Met Val Gly Thr
        260                 265                 270

Tyr Thr Ala Met Ile Leu Gly Lys Ile Leu Ala Gly Phe Met Ala Asp
    275                 280                 285

Lys Leu Gly Arg Arg Phe Thr Tyr Ala Phe Gly Ala Ile Gly Thr Ala
    290                 295                 300

Ile Phe Leu Pro Leu Ile Val Phe Tyr Asn Ser Pro Asp Asn Ile Leu
305                 310                 315                 320

Tyr Leu Leu Val Ile Phe Gly Phe Leu Tyr Gly Ile Pro Tyr Gly Val
                325                 330                 335

Asn Ala Thr Tyr Met Ile Glu Ser Phe Pro Thr Ala Ile Arg Gly Thr
                340                 345                 350

Ala Ile Gly Gly Ala Tyr Asn Val Gly Arg Leu Gly Ala Ala Ile Ala
                355                 360                 365

Pro Ala Thr Ile Gly Phe Leu Ala Ser Gly Gly Ser Ile Gly Leu Gly
    370                 375                 380

Phe Val Val Met Gly Ala Ala Tyr Phe Ile Cys Gly Val Ile Pro Ala
385                 390                 395                 400

Leu Phe Ile Lys Glu Lys Gln Tyr Asp Pro Gln Gln Ser
                405                 410

<210> SEQ ID NO 7
<211> LENGTH: 944
<212> TYPE: DNA
<213> ORGANISM: Artificial Sequence
<220> FEATURE:
<223> OTHER INFORMATION: nt sequence for mucK246

<400> SEQUENCE: 7
atgtacagca acaatcagag atccagaatt ggatcacaca catggaaaat tgctttttta      60
tttgcatttt tagcgttgct tgtggatgga gcagacctga tgttgctctc ttatagttta     120
aacagtatta aagctgagtt taatttaagt acagttgaag ctggaatgtt gggaagtttt     180
actttagctg gcatggcgat aggtggaatc tttggtgggt gggcgtgtga ccgatttggt     240
cgtgtacgca ttgttgtgat ttcaattctc acgttctcaa tcctaacgtg tggccttgga     300
ttgactcaga gctttataca atttggtgtt ttacgtttct tcgcttcact cggtttaggt     360
tctttatata ttgcctgcaa tacctcatg gccgaatgtg ttccaacaaa ataccgtact      420
actgttttag gtacattaca ggctggctgg actgttggct atattgttgc caccttactg     480
gctggttggt taatacccga tcatggttgg cgtgtgctgt tttatgttgc gattattcct     540
gtacttatgg ctgtacttat gcatttttt gtaccagaac cagcagcatg caacaatca      600
cgcttagcac catccaaaca aactgaaaca gtcaaaactt ctgcctttaa attaatcttt     660
caagataaac gtaaccgtaa catgttcatt ctgtgggcac tcaccgcagg ctttctacaa     720
tttggttact atggcgtaaa caattggatg ccatcttatc ttgaaagtga attgggaatg     780
aagtttaagg aaatgacagc ctatatggtc ggaacataca ctgccatgat tttaggaaaa     840
atcttggctg gctttatggc tgataaactc ggccgtcgtt ttacttatgc atttggtgct     900
atcggaaccg caattttttt acctctaatc gtgttttata actc                     944

<210> SEQ ID NO 8
<211> LENGTH: 413
<212> TYPE: PRT
<213> ORGANISM: Artificial Sequence
<220> FEATURE:

<223> OTHER INFORMATION: aa sequence for mucK246

<400> SEQUENCE: 8

```
Met Tyr Ser Asn Asn Gln Arg Ser Arg Ile Gly Ser His Thr Trp Lys
1               5                   10                  15

Ile Ala Phe Leu Phe Ala Phe Leu Ala Leu Leu Val Asp Gly Ala Asp
                20                  25                  30

Leu Met Leu Leu Ser Tyr Ser Leu Asn Ser Ile Lys Ala Glu Phe Asn
            35                  40                  45

Leu Ser Thr Val Glu Ala Gly Met Leu Gly Ser Phe Thr Leu Ala Gly
        50                  55                  60

Met Ala Ile Gly Gly Ile Phe Gly Gly Trp Ala Cys Asp Arg Phe Gly
65                  70                  75                  80

Arg Val Arg Ile Val Ile Ser Ile Leu Thr Phe Ser Ile Leu Thr
                85                  90                  95

Cys Gly Leu Gly Leu Thr Gln Ser Phe Ile Gln Phe Gly Val Leu Arg
                100                 105                 110

Phe Phe Ala Ser Leu Gly Leu Gly Ser Leu Tyr Ile Ala Cys Asn Thr
            115                 120                 125

Leu Met Ala Glu Cys Val Pro Thr Lys Tyr Arg Thr Thr Val Leu Gly
130                 135                 140

Thr Leu Gln Ala Gly Trp Thr Val Gly Tyr Ile Val Ala Thr Leu Leu
145                 150                 155                 160

Ala Gly Trp Leu Ile Pro Asp His Gly Trp Arg Val Leu Phe Tyr Val
                165                 170                 175

Ala Ile Ile Pro Val Leu Met Ala Val Leu Met His Phe Phe Val Pro
                180                 185                 190

Glu Pro Ala Ala Trp Gln Gln Ser Arg Leu Ala Pro Ser Lys Gln Thr
            195                 200                 205

Glu Thr Val Lys Thr Ser Ala Phe Lys Leu Ile Phe Gln Asp Lys Arg
210                 215                 220

Asn Arg Asn Met Phe Ile Leu Trp Ala Leu Thr Ala Gly Phe Leu Gln
225                 230                 235                 240

Phe Gly Tyr Tyr Gly Val Asn Asn Trp Met Pro Ser Tyr Leu Glu Ser
                245                 250                 255

Glu Leu Gly Met Lys Phe Lys Glu Met Thr Ala Tyr Met Val Gly Thr
            260                 265                 270

Tyr Thr Ala Met Ile Leu Gly Lys Ile Leu Ala Gly Phe Met Ala Asp
        275                 280                 285

Lys Leu Gly Arg Arg Phe Thr Tyr Ala Phe Gly Ala Ile Gly Thr Ala
        290                 295                 300

Ile Phe Leu Pro Leu Ile Val Phe Tyr Asn Ser Pro Asp Asn Ile Leu
305                 310                 315                 320

Tyr Leu Leu Val Ile Phe Gly Phe Leu Tyr Gly Ile Pro Tyr Gly Val
                325                 330                 335

Asn Ala Thr Tyr Met Thr Glu Ser Phe Pro Thr Ala Ile Arg Gly Thr
            340                 345                 350

Ala Ile Gly Gly Ala Tyr Asn Val Gly Arg Leu Gly Ala Ala Ile Ala
        355                 360                 365

Pro Ala Thr Ile Gly Phe Leu Ala Ser Gly Gly Ser Ile Gly Leu Gly
        370                 375                 380

Phe Val Val Met Gly Ala Ala Tyr Phe Ile Cys Gly Val Ile Pro Ala
385                 390                 395                 400
```

Leu Phe Ile Lys Glu Lys Gln Tyr Asp Pro Gln Gln Ser
                405                 410

<210> SEQ ID NO 9
<211> LENGTH: 458
<212> TYPE: PRT
<213> ORGANISM: Artificial Sequence
<220> FEATURE:
<223> OTHER INFORMATION: aa sequence for TpaK_RHA1

<400> SEQUENCE: 9

Met Ser Leu Ala Pro Ser Arg Val Thr Leu Pro Asp Phe Ile Asp Ser
1               5                   10                  15

Arg Pro Val Ser Arg Tyr Gln Tyr Ile Val Ile Ala Leu Cys Gly Val
            20                  25                  30

Val Met Phe Ile Asp Gly Phe Asp Thr Gln Ser Ile Ser Tyr Met Ala
        35                  40                  45

Pro His Ile Ala Glu Glu Trp Gly Leu Ser Lys Gln Val Leu Gly Pro
    50                  55                  60

Ile Phe Ser Ala Ala Leu Ala Gly Leu Met Val Gly Tyr Leu Ala Leu
65                  70                  75                  80

Ser Pro Leu Ser Glu Arg Phe Gly His Arg Arg Met Ile Leu Thr Ser
                85                  90                  95

Thr Val Ile Phe Ala Leu Gly Thr Leu Ala Ala Ala Trp Ser Gln Asn
            100                 105                 110

Val Thr Glu Leu Met Ala Leu Arg Phe Ile Thr Gly Met Gly Leu Gly
        115                 120                 125

Ala Ala Ala Pro Ser Ala Ile Ala Leu Thr Gly Glu Phe Ser Pro Lys
    130                 135                 140

Arg Leu Arg Ala Thr Phe Val Leu Val Ile Tyr Cys Gly Phe Ser Leu
145                 150                 155                 160

Gly Phe Val Ala Ala Gly Leu Val Ser Gly Trp Leu Ile Pro Ile Leu
                165                 170                 175

Gly Trp Arg Ser Val Leu Val Val Gly Ala Val Ala Pro Leu Leu Leu
            180                 185                 190

Leu Pro Ala Leu Leu Arg Tyr Leu Pro Asp Ser Leu Thr Ser Met Ile
        195                 200                 205

Asn Arg Gly Ala Glu Pro Asn Arg Ile Gln Ala Ile Phe Arg Lys Met
    210                 215                 220

Asp Pro Ala Leu Ala Val Gly Pro Asp Ile Thr Tyr Glu Ala Glu Lys
225                 230                 235                 240

Arg Thr Asp Gly Gln Arg Thr Ala Leu Arg Ser Leu Phe Thr Arg Asp
                245                 250                 255

Arg Val Leu Gly Thr Leu Leu Trp Leu Val Phe Val Ile Asn Leu
            260                 265                 270

Gly Glu Phe Tyr Ala Leu Gln Ser Trp Leu Pro Ser Ile Met Thr Ser
        275                 280                 285

Leu Tyr Asp Met Gly Thr Val Val Thr Ala Thr Thr Leu Thr Thr Val
    290                 295                 300

Gly Gly Ile Ala Ala Ala Phe Val Thr Gly Pro Cys Met Asp Arg Leu
305                 310                 315                 320

Gly Ala Tyr Val Thr Leu Gly Thr Val Tyr Val Val Gly Phe Ala Phe
                325                 330                 335

Val Ala Leu Thr Gly Val Ala Phe Thr Ala Pro Leu Trp Val Leu Leu
            340                 345                 350

```
Thr Ala Asn Phe Phe Ala Gly Val Cys Ile Ser Gly Gln Lys Ser
            355                 360                 365

Leu Ile Ala Leu Ser Ala Val Phe Tyr Pro Thr Pro Met Arg Ser Thr
370                 375                 380

Gly Val Gly Trp Ala Leu Gly Val Gly Arg Leu Gly Gly Ile Val Gly
385                 390                 395                 400

Pro Ile Ala Val Gly Ala Ala Leu Gly Met Gly Trp Ser Ala Ser Ala
                405                 410                 415

Val Phe Tyr Ala Met Ser Val Pro Met Leu Val Ala Gly Ala Ala Val
                420                 425                 430

Phe Leu Leu Gly Arg Trp Val Arg Ser Asp Asn His Pro Asp Arg Lys
            435                 440                 445

Ser Ala Glu Ser His Ser Leu Ala Arg Lys
    450                 455

<210> SEQ ID NO 10
<211> LENGTH: 459
<212> TYPE: PRT
<213> ORGANISM: Artificial Sequence
<220> FEATURE:
<223> OTHER INFORMATION: aa sequence for TpaK_DK17

<400> SEQUENCE: 10

Met Ser Leu Ala Pro Ser Arg Val Thr Leu Pro Asp Phe Ile Asp Ser
1               5                   10                  15

Arg Pro Val Ser Arg Tyr Gln Tyr Ile Val Ile Ala Leu Cys Gly Val
            20                  25                  30

Val Met Phe Ile Asp Gly Phe Asp Thr Gln Ser Ile Ser Tyr Met Ala
        35                  40                  45

Pro His Ile Ala Glu Glu Trp Gly Leu Ser Lys Gln Val Leu Gly Pro
    50                  55                  60

Ile Phe Ser Ala Ala Leu Ala Gly Leu Met Val Gly Tyr Leu Ala Leu
65                  70                  75                  80

Ser Pro Leu Ser Glu Arg Phe Gly His Arg Arg Met Ile Leu Thr Ser
                85                  90                  95

Thr Val Ile Phe Ala Leu Gly Thr Leu Ala Ala Ala Trp Ser Gln Asn
            100                 105                 110

Val Thr Glu Leu Met Ala Leu Arg Phe Ile Thr Gly Met Gly Leu Gly
        115                 120                 125

Ala Ala Ala Pro Ser Ala Ile Ala Leu Thr Gly Glu Phe Ser Pro Lys
    130                 135                 140

Arg Leu Arg Ala Thr Phe Val Leu Val Ile Tyr Cys Gly Phe Ser Leu
145                 150                 155                 160

Gly Phe Val Ala Ala Gly Leu Val Ser Gly Trp Leu Ile Pro Ile Leu
                165                 170                 175

Gly Trp Arg Ser Val Leu Val Val Gly Ala Val Ala Pro Leu Leu Leu
            180                 185                 190

Leu Pro Ala Leu Leu Arg Tyr Leu Pro Asp Ser Leu Thr Ser Met Ile
        195                 200                 205

Asn Arg Gly Ala Glu Pro Asn Arg Ile Gln Ala Ile Phe Arg Lys Met
    210                 215                 220

Asp Pro Ala Leu Ala Val Gly Pro Asp Ile Thr Tyr Glu Ala Glu Lys
225                 230                 235                 240

Arg Thr Asp Gly Gln Arg Thr Ala Leu Arg Ser Leu Phe Thr Arg Asp
                245                 250                 255
```

Arg Val Leu Gly Thr Leu Leu Leu Trp Leu Val Phe Val Ile Asn Leu
                260                 265                 270

Gly Glu Phe Tyr Ala Leu Gln Ser Trp Leu Pro Ser Ile Met Thr Ser
            275                 280                 285

Leu Asp Tyr Asn Met Gly Thr Val Val Ala Thr Thr Leu Thr Thr
        290                 295                 300

Val Gly Gly Ile Ala Ala Ala Phe Val Thr Gly Pro Cys Met Asp Arg
305                 310                 315                 320

Leu Gly Ala Tyr Val Thr Leu Gly Thr Val Tyr Val Gly Phe Ala
                325                 330                 335

Phe Val Ala Leu Thr Gly Val Ala Phe Thr Ala Pro Leu Trp Val Leu
            340                 345                 350

Leu Thr Ala Asn Phe Phe Ala Gly Val Cys Ile Ser Gly Gly Gln Lys
                355                 360                 365

Ser Leu Ile Ala Leu Ser Ala Val Phe Tyr Pro Thr Pro Met Arg Ser
            370                 375                 380

Thr Gly Val Gly Trp Ala Leu Gly Val Gly Arg Leu Gly Gly Ile Val
385                 390                 395                 400

Gly Pro Ile Ala Val Gly Ala Ala Leu Gly Met Gly Trp Ser Ala Ser
                405                 410                 415

Ala Val Phe Tyr Ala Met Ser Val Pro Met Leu Val Ala Gly Ala Ala
            420                 425                 430

Val Phe Leu Leu Gly Arg Trp Val Arg Ser Asp Asn His Pro Asp Arg
                435                 440                 445

Lys Ser Ala Glu Ser His Ser Leu Ala Arg Lys
        450                 455

<210> SEQ ID NO 11
<211> LENGTH: 422
<212> TYPE: PRT
<213> ORGANISM: Artificial Sequence
<220> FEATURE:
<223> OTHER INFORMATION: aa sequence for TpaK_LB400

<400> SEQUENCE: 11

Met Ala Ser Pro Leu Ile Asp Val Val Glu Val Ile Glu Arg Gln Lys
1               5                   10                  15

Val Gly Ile Gly Gln Ser Lys Asp Trp His Leu Pro Arg Glu Val Leu
            20                  25                  30

Gly Ser Ile Phe Ser Ala Ala Leu Val Gly Leu Met Val Gly Tyr Leu
        35                  40                  45

Ala Ile Ala Pro Leu Ser Ala Arg Phe Gly His Lys Arg Met Met Leu
    50                  55                  60

Ala Ser Ser Val Leu Phe Ala Leu Phe Thr Leu Leu Thr Leu Phe Ala
65                  70                  75                  80

Thr Asn Val Thr Glu Leu Ile Gly Leu Arg Phe Leu Thr Gly Ile Gly
                85                  90                  95

Leu Gly Ala Ala Ala Pro Ser Ala Val Ala Leu Thr Cys Glu Phe Ala
            100                 105                 110

Pro Lys Arg Leu Arg Ala Thr Phe Val Leu Leu Val Tyr Cys Gly Phe
        115                 120                 125

Ser Leu Gly Phe Val Val Ala Gly Leu Thr Ala Gly Ala Leu Met Pro
    130                 135                 140

Ala Phe Gly Trp Lys Ser Leu Met Leu Val Gly Ala Leu Ala Pro Ile
145                 150                 155                 160

```
Ala Leu Thr Val Pro Leu Ala Trp Leu Leu Pro Glu Ser Leu Val Val
            165                 170                 175

Leu Gln Arg Arg Pro Asn Gly Asp Glu Arg Met Arg Ala Val Leu Leu
        180                 185                 190

Gly Phe Phe Pro Arg Leu Asp Val Pro Val Gly Ser Arg Phe Arg Leu
        195                 200                 205

Glu Asp Gln Gly Glu Ala Arg Ala Ser Val Thr Ala Leu Val Arg Gly
210                 215                 220

Arg Thr Ser Ala Gly Thr Leu Leu Trp Leu Ile Phe Phe Leu Asn
225                 230                 235                 240

Leu Ala Glu Phe Tyr Phe Met Gln Ser Trp Leu Pro Thr Met Leu Thr
                245                 250                 255

Gly Leu Gln Tyr Ser Pro Ala Thr Val Val Trp Val Thr Ala Leu Pro
            260                 265                 270

Thr Ile Ala Gly Val Leu Ser Ala Val Pro Leu Gly Leu Ala Met Asp
        275                 280                 285

Arg Val Gly Pro Tyr Val Thr Leu Thr Val Met Tyr Leu Ala Gly Cys
290                 295                 300

Val Phe Met Trp Leu Val Gly Gly Ala Phe Ser Gly Ser Val Ala Trp
305                 310                 315                 320

Leu Met Val Met Val Phe Cys Ala Gly Phe Cys Ile Ser Gly Gly Gln
                325                 330                 335

Lys Ser Val Ile Ala Leu Ala Ala Val Tyr Tyr Pro Leu Asn Leu Arg
            340                 345                 350

Ser Thr Gly Val Gly Trp Ala Leu Gly Ile Gly Arg Leu Gly Gly Ile
        355                 360                 365

Ala Gly Pro Leu Ser Ala Gly Met Leu Tyr Ser Ala His Trp Thr Pro
370                 375                 380

Ala Glu Ile Phe Arg Phe Ser Ala Trp Pro Val Leu Ile Ala Gly Leu
385                 390                 395                 400

Ala Val Phe Val Met Gly Arg Ile Tyr Gly Ser Arg Pro Val Ala Val
                405                 410                 415

Glu Val Ser Thr Pro His
            420

<210> SEQ ID NO 12
<211> LENGTH: 413
<212> TYPE: PRT
<213> ORGANISM: Artificial Sequence
<220> FEATURE:
<223> OTHER INFORMATION: aa sequence for MucK_IP255

<400> SEQUENCE: 12

Met Tyr Ser Asn Asn Gln Arg Ser Arg Ile Gly Ser His Thr Trp Lys
1               5                   10                  15

Ile Ala Phe Leu Phe Ala Phe Leu Ala Leu Leu Val Asp Gly Ala Asp
            20                  25                  30

Leu Met Leu Leu Ser Tyr Ser Leu Asn Ser Ile Lys Ala Glu Phe Asn
        35                  40                  45

Leu Ser Thr Val Glu Ala Gly Met Leu Gly Ser Phe Thr Leu Ala Gly
50                  55                  60

Met Ala Ile Gly Gly Ile Phe Gly Gly Trp Ala Cys Asp Arg Phe Gly
65                  70                  75                  80

Arg Val Arg Ile Val Val Ile Ser Ile Leu Thr Phe Ser Ile Leu Thr
                85                  90                  95
```

```
Cys Gly Leu Gly Leu Thr Gln Ser Phe Ile Gln Phe Gly Val Leu Arg
            100                 105                 110

Phe Phe Ala Ser Leu Gly Leu Gly Ser Leu Tyr Ile Ala Cys Asn Thr
        115                 120                 125

Leu Met Ala Glu Tyr Val Pro Thr Lys Tyr Arg Thr Thr Val Leu Gly
    130                 135                 140

Thr Leu Gln Ala Gly Cys Thr Val Gly Tyr Ile Val Ala Thr Leu Leu
145                 150                 155                 160

Ala Gly Trp Leu Ile Pro Asp His Gly Trp Arg Val Leu Phe Tyr Val
                165                 170                 175

Ala Ile Ile Pro Val Leu Met Ala Val Leu Met His Phe Phe Val Pro
            180                 185                 190

Glu Pro Ala Ala Trp Gln Gln Ser Arg Leu Ala Pro Ser Lys Gln Thr
        195                 200                 205

Glu Thr Val Lys Thr Ser Ala Phe Lys Leu Ile Phe Gln Asp Lys Arg
    210                 215                 220

Asn Arg Asn Met Phe Ile Leu Trp Ala Leu Thr Ala Gly Phe Leu Gln
225                 230                 235                 240

Phe Gly Tyr Tyr Gly Val Asn Asn Trp Met Pro Ser Tyr Leu Glu Ser
                245                 250                 255

Glu Leu Gly Met Lys Phe Lys Glu Met Thr Ala Tyr Met Val Gly Thr
            260                 265                 270

Tyr Thr Ala Met Ile Leu Gly Lys Ile Leu Ala Gly Phe Met Ala Asp
        275                 280                 285

Lys Leu Gly Arg Arg Phe Thr Tyr Ala Phe Gly Ala Ile Gly Thr Ala
    290                 295                 300

Ile Phe Leu Pro Leu Ile Val Phe Tyr Asn Ser Pro Asp Asn Ile Leu
305                 310                 315                 320

Tyr Leu Leu Val Ile Phe Gly Phe Leu Tyr Gly Ile Pro Tyr Gly Val
                325                 330                 335

Asn Ala Thr Tyr Met Thr Glu Ser Phe Pro Thr Ala Ile Arg Gly Thr
            340                 345                 350

Ala Ile Gly Gly Ala Tyr Asn Val Gly Arg Leu Gly Ala Ala Ile Ala
        355                 360                 365

Pro Ala Thr Ile Gly Phe Leu Ala Ser Gly Gly Ser Ile Gly Leu Gly
    370                 375                 380

Phe Val Val Met Gly Ala Ala Tyr Phe Ile Cys Gly Val Ile Pro Ala
385                 390                 395                 400

Leu Phe Thr Lys Glu Lys Gln Tyr Asp Pro Gln Gln Ser
                405                 410

<210> SEQ ID NO 13
<211> LENGTH: 454
<212> TYPE: PRT
<213> ORGANISM: Acinetobacter baylyi

<400> SEQUENCE: 13

Met Asp Asn Leu Gln Thr Ser Ala Val Ser Ile Ser Lys Val Arg Val
1               5                   10                  15

Thr His Asn Lys Thr Arg Tyr Tyr Ile Leu Ala Met Ile Phe Leu Val
            20                  25                  30

Thr Ala Leu Asn Tyr Gly Asp Arg Ala Thr Ile Ser Met Ala Ala Thr
        35                  40                  45

Pro Met Ser Gln Glu Leu Gly Leu Thr Ser Val Thr Met Gly Tyr Ile
    50                  55                  60
```

```
Phe Ser Ala Phe Gly Trp Ala Tyr Val Ile Gly Gln Val Pro Gly Gly
 65                  70                  75                  80

Trp Leu Leu Asp Lys Phe Gly Ala Arg Lys Val Tyr Phe Trp Ser Ile
                 85                  90                  95

Leu Leu Trp Ser Ile Phe Thr Val Leu Leu Gly Phe Val Asp Ile Phe
            100                 105                 110

Gly Ser Ile Pro Leu Ile Ile Ala Ser Leu Phe Ile Leu Arg Phe Leu
        115                 120                 125

Val Gly Leu Ser Glu Ser Pro Ala Phe Pro Gly Asn Ser Gln Ile Val
130                 135                 140

Ala Ala Trp Phe Pro Thr Lys Glu Arg Gly Thr Ala Ala Ser Phe
145                 150                 155                 160

Asn Ser Ala Gln Tyr Phe Ala Thr Val Ile Phe Ala Pro Phe Met Gly
                165                 170                 175

Trp Leu Val Thr His Ile His Trp Gln Ser Val Phe Trp Ile Met Gly
            180                 185                 190

Ala Ile Gly Ile Val Ile Ala Phe Ile Trp Leu Lys Val Ile Tyr Ser
        195                 200                 205

Pro Glu Lys His Pro Arg Ile Asn Lys Glu Glu Leu Thr Tyr Leu Gln
210                 215                 220

Gly Asn Gly Ala Ile Thr Ser Met Gly Glu Asn Lys Ser Lys Thr Leu
225                 230                 235                 240

Asp Gln Lys Asn Lys Met Ser Trp Ser Asn Val Lys Lys Leu Leu Ser
                245                 250                 255

Ser Arg Met Leu Leu Gly Ile Phe Ile Ala Gln Tyr Cys Ile Thr Cys
            260                 265                 270

Leu Thr Tyr Phe Phe Leu Thr Trp Phe Pro Val Tyr Leu Val Lys Glu
        275                 280                 285

Arg His Met Thr Ile Leu Gln Ala Gly Phe Ala Ala Val Leu Pro Ala
        290                 295                 300

Leu Cys Gly Phe Ile Gly Gly Ile Leu Gly Gly Ile Ile Ser Asp Arg
305                 310                 315                 320

Leu Ile Arg Met Asn Lys Ser Leu Ser Phe Ser Arg Lys Phe Pro Ile
                325                 330                 335

Val Leu Gly Met Leu Leu Ser Thr Ser Ile Ile Val Cys Asn Tyr Val
            340                 345                 350

Asp Ser Gln Thr Ala Ile Val Phe Phe Met Ser Leu Ala Phe Phe Gly
        355                 360                 365

Lys Gly Phe Gly Ala Leu Gly Trp Ala Val Met Ser Asp Val Ala Pro
        370                 375                 380

Lys Glu Met Ile Gly Leu Ser Gly Gly Leu Phe Asn Thr Phe Gly Asn
385                 390                 395                 400

Thr Ala Gly Ile Ile Ile Pro Ile Ala Ile Gly Tyr Ile Val Ala Ser
                405                 410                 415

Thr Gly Ser Phe Asn Gly Ala Leu Val Phe Val Gly Ile His Ala Ile
            420                 425                 430

Ile Ala Ile Leu Cys Tyr Leu Phe Val Val Gly Lys Ile Glu Arg Phe
        435                 440                 445

Glu Leu Lys Lys Val Ile
450

<210> SEQ ID NO 14
<211> LENGTH: 454
```

```
<212> TYPE: PRT
<213> ORGANISM: Artificial Sequence
<220> FEATURE:
<223> OTHER INFORMATION: aa sequence for GudP_IP247

<400> SEQUENCE: 14

Met Asp Asn Leu Gln Thr Ser Ala Val Ser Ile Ser Lys Val Arg Val
1               5                   10                  15

Thr His Asn Lys Thr Arg Tyr Tyr Ile Leu Ala Met Ile Phe Leu Val
            20                  25                  30

Thr Ala Leu Asn Tyr Gly Asp Arg Ala Thr Ile Ser Met Ala Ala Thr
        35                  40                  45

Pro Met Ser Gln Glu Leu Gly Leu Thr Ser Val Thr Met Gly Tyr Ile
    50                  55                  60

Phe Ser Ala Phe Gly Trp Ala Tyr Val Ile Gly Gln Val Pro Gly Gly
65                  70                  75                  80

Trp Leu Leu Asp Lys Phe Gly Ala Arg Lys Val Tyr Phe Trp Ser Ile
                85                  90                  95

Leu Leu Trp Ser Ile Phe Thr Val Leu Leu Gly Phe Val Asp Ile Phe
            100                 105                 110

Gly Ser Ile Pro Leu Ile Ile Ala Ser Leu Phe Ile Leu Arg Phe Leu
        115                 120                 125

Val Gly Leu Ser Glu Ser Pro Ala Phe Pro Gly Asn Ser Gln Ile Val
    130                 135                 140

Ala Ala Trp Phe Pro Thr Lys Glu Arg Gly Thr Ala Ala Ser Phe
145                 150                 155                 160

Asn Ser Ala Gln Tyr Phe Ala Thr Val Ile Phe Ala Pro Phe Met Gly
                165                 170                 175

Trp Leu Val Thr His Ile His Trp Gln Ser Val Phe Trp Ile Met Gly
            180                 185                 190

Ala Ile Gly Ile Val Ile Ala Phe Ile Trp Leu Lys Val Ile Tyr Ser
        195                 200                 205

Pro Glu Lys His Pro Arg Ile Asn Lys Glu Glu Leu Thr Tyr Leu Gln
    210                 215                 220

Gly Asn Gly Ala Ile Thr Ser Met Gly Glu Asn Lys Ser Lys Thr Leu
225                 230                 235                 240

Asp Gln Lys Asn Lys Met Ser Trp Ser Asn Val Lys Lys Leu Leu Ser
                245                 250                 255

Ser Arg Met Leu Leu Gly Ile Phe Ile Ala Gln Tyr Cys Ile Thr Cys
            260                 265                 270

Leu Thr Tyr Phe Phe Leu Thr Trp Phe Pro Val Tyr Leu Val Lys Glu
        275                 280                 285

Cys His Met Thr Ile Leu Gln Ala Gly Phe Ala Ala Val Leu Pro Ala
    290                 295                 300

Leu Cys Gly Phe Ile Gly Gly Ile Leu Gly Gly Ile Ser Asp Arg
305                 310                 315                 320

Leu Ile Arg Met Asn Lys Ser Leu Ser Phe Ser Arg Lys Phe Pro Ile
                325                 330                 335

Val Leu Gly Met Leu Leu Ser Thr Ser Ile Ile Val Cys Asn Tyr Val
            340                 345                 350

Asp Ser Gln Thr Ala Ile Val Phe Met Ser Leu Ala Phe Phe Gly
        355                 360                 365

Lys Gly Phe Gly Ala Leu Gly Trp Ala Val Met Ser Asp Val Ala Pro
    370                 375                 380
```

```
Lys Glu Met Ile Gly Leu Ser Gly Gly Leu Phe Asn Thr Phe Gly Asn
385                 390                 395                 400

Thr Ala Gly Ile Ile Ile Pro Ile Ala Ile Gly Tyr Ile Val Ala Ser
            405                 410                 415

Thr Gly Ser Phe Asn Gly Ala Leu Val Phe Val Gly Ile His Ala Ile
            420                 425                 430

Ile Ala Ile Leu Cys Tyr Leu Phe Val Val Gly Lys Ile Glu Arg Phe
            435                 440                 445

Glu Leu Lys Lys Val Ile
    450
```

<210> SEQ ID NO 15
<211> LENGTH: 454
<212> TYPE: PRT
<213> ORGANISM: Artificial Sequence
<220> FEATURE:
<223> OTHER INFORMATION: aa sequence for GudP_IP250

<400> SEQUENCE: 15

```
Met Asp Asn Leu Gln Thr Ser Ala Val Ser Ile Ser Lys Val Arg Val
1               5                   10                  15

Thr His Asn Lys Thr Arg Tyr Tyr Ile Leu Ala Met Ile Phe Leu Val
            20                  25                  30

Thr Ala Leu Asn Tyr Gly Asp Arg Ala Thr Ile Ser Met Ala Ala Thr
        35                  40                  45

Pro Met Ser Gln Glu Leu Gly Leu Thr Ser Val Thr Met Gly Tyr Ile
    50                  55                  60

Phe Ser Ala Phe Gly Trp Ala Tyr Val Ile Gln Val Pro Gly Gly
65                  70                  75                  80

Trp Leu Leu Asp Lys Phe Gly Ala Arg Lys Val Tyr Phe Trp Ser Ile
                85                  90                  95

Leu Leu Trp Ser Ile Phe Thr Val Leu Leu Gly Phe Val Asp Ile Phe
            100                 105                 110

Gly Ser Ile Pro Leu Ile Ile Ala Ser Leu Phe Ile Leu Arg Phe Leu
            115                 120                 125

Val Gly Leu Ser Glu Ser Pro Ala Phe Pro Gly Asn Ser Gln Ile Val
    130                 135                 140

Ala Ala Trp Phe Pro Thr Lys Glu Arg Gly Thr Ala Ala Ser Phe
145                 150                 155                 160

Asn Ser Ala Gln Tyr Phe Ala Thr Val Ile Phe Ala Pro Phe Met Gly
                165                 170                 175

Trp Leu Val Thr His Ile His Trp Gln Ser Val Phe Trp Ile Met Gly
            180                 185                 190

Ala Ile Gly Ile Val Ile Ala Phe Ile Trp Leu Lys Val Ile Tyr Ser
            195                 200                 205

Pro Glu Lys His Pro Arg Ile Asn Lys Glu Glu Leu Thr Tyr Leu Gln
    210                 215                 220

Gly Asn Gly Ala Ile Thr Ser Met Gly Glu Asn Lys Ser Lys Thr Leu
225                 230                 235                 240

Asp Gln Lys Asn Lys Met Ser Trp Ser Asn Val Lys Lys Leu Leu Ser
                245                 250                 255

Ser Arg Met Leu Leu Gly Ile Phe Ile Ala Gln Tyr Cys Ile Thr Cys
            260                 265                 270

Leu Thr Tyr Phe Phe Leu Thr Trp Phe Pro Val Tyr Leu Val Lys Glu
            275                 280                 285
```

```
Arg His Met Thr Ile Leu Gln Ala Gly Phe Ala Ala Val Leu Pro Ala
            290                 295                 300

Leu Cys Gly Phe Ile Gly Gly Ile Leu Gly Gly Ile Ile Ser Asp Arg
305                 310                 315                 320

Leu Ile Arg Met Asn Lys Ser Leu Ser Phe Ser Arg Lys Phe Pro Ile
                325                 330                 335

Val Leu Gly Met Leu Leu Ser Thr Ser Ile Ile Val Cys Asn Tyr Val
            340                 345                 350

Asp Ser Gln Thr Ala Ile Val Phe Phe Met Ser Leu Ala Phe Phe Gly
        355                 360                 365

Lys Gly Phe Gly Ala Leu Gly Trp Ala Val Met Ser Asp Val Ala Pro
370                 375                 380

Lys Glu Met Ile Gly Leu Ser Gly Gly Leu Phe Asn Thr Phe Gly Asn
385                 390                 395                 400

Thr Ala Gly Ile Ile Ile Pro Ile Ala Ile Gly Tyr Ile Val Ala Ser
                405                 410                 415

Thr Gly Ser Phe Asn Gly Ala Leu Val Phe Val Gly Ile His Ala Ile
            420                 425                 430

Ile Ala Ile Leu Cys Tyr Leu Phe Val Val Gly Lys Ile Glu Leu Phe
        435                 440                 445

Glu Leu Lys Lys Val Ile
    450
```

```
<210> SEQ ID NO 16
<211> LENGTH: 1512
<212> TYPE: DNA
<213> ORGANISM: Artificial Sequence
<220> FEATURE:
<223> OTHER INFORMATION: nt sequence from Figure 6

<400> SEQUENCE: 16
atggatctta ttcaaaactt aagtaccggc ttcggtgtgg ctttcacttt ccaaaatttg      60
atttattgtt tcgttggttg tcttttaggt actttaattg gcgtacttcc aggcattggt     120
ccagttgcta caattgcaat gttattgcct gcaacctatg ctttaccacc agtggctgca     180
ttgattatgt tggctggtat ctactatggt gcgcagtatg gtggtagtac tactgctatt     240
ttggtaaatc tttccgggtga atcttcttct gtagtcaccg ttatcgatgg ttaccaaatg    300
gctcgtaaag gtcgtgcagg tccagcgctt gctgctgctg gtattggttc ttttttcgca    360
ggttgtgttg gtacagtgat cttagcggct ttcgctccac ctctcacgga agttgcattc    420
aagtttggac ctgcagagta tttttcttta atgacattgg gtctaattgg tgcagttgtc    480
cttgcttcag gctctttgct caaagcaatt gcaatgatcg tactcggtct tttgcttggc    540
atggttggta cggacgtaaa ttcaggtgta gcgcgttact catttgacat tccagagcta    600
acagatggta ttgattttgt tgtgatcgca atgggtgttt ttggttacgg tgaaattatt    660
gcaaatcttt caaagcctga tgatgaacgt gaggttttg cagcgaaagt gactggtctt    720
cttccaacaa gtgaagactt caaacgtatg ttgccagcaa tgttgcgtgg tacagcatta    780
ggttcagctt taggaatttt gccaggtggt ggtgctatgt tgagtgcatt tgcagcttat    840
acaattgaaa aaaaaaccaa attaaaacct ggtgaagtac catttggtca gggcaatatt    900
cgtggcgttt gcgctccgga atcagcaaac aacgctggta gtcaaacatc tttcattcca    960
ctgttaacat tgggcattcc ttcaaacgcc gtaatggctc tcatggtagg cgcaatgact   1020
attcacaaca ttcaaccagg accacaagtg atgacatcta accctgaact attttggggt   1080
```

```
cttattgcaa gcatgtagat tggtaatttg atgttaatta ttttgaacct accacttatc    1140
ggtgtgtgga tcaagttgct tacagtacca tatcgttggt tgtttccatc tatcgtatta    1200
ttttgtgcaa ttggtgtgta tggtactaat aacaacgttt gggatgtttg gatggtaggt    1260
atttttggtt tcattggtta tgtattccac aagttaggga ctgaacctgc tcctttgttg    1320
ttgggtttca ttttaggtcc aatgatggaa gaaaaccttc gccgtgctct attgctatcg    1380
cgtggcgact ggtctgtatt tgttacgcgt ccaattagtg catgcttact ggcagcggct    1440
gttgtgcttc ttgtaatcgt tcttatgcct gcagttaaga ataaacgtga agaggccttt    1500
gtagaagatt ga                                                        1512
```

<210> SEQ ID NO 17
<211> LENGTH: 502
<212> TYPE: PRT
<213> ORGANISM: Artificial Sequence
<220> FEATURE:
<223> OTHER INFORMATION: aa sequence for Figure 6

<400> SEQUENCE: 17

```
Met Asp Leu Ile Gln Asn Leu Ser Thr Gly Phe Gly Val Ala Phe Thr
1               5                   10                  15

Phe Gln Asn Leu Ile Tyr Cys Phe Val Gly Cys Leu Leu Gly Thr Leu
                20                  25                  30

Ile Gly Val Leu Pro Gly Ile Gly Pro Val Ala Thr Ile Ala Met Leu
            35                  40                  45

Leu Pro Ala Thr Tyr Ala Leu Pro Val Ala Ala Leu Ile Met Leu
        50                  55                  60

Ala Gly Ile Tyr Tyr Gly Ala Gln Tyr Gly Gly Ser Thr Thr Ala Ile
65                  70                  75                  80

Leu Val Asn Leu Pro Gly Glu Ser Ser Val Val Thr Val Ile Asp
                85                  90                  95

Gly Tyr Gln Met Ala Arg Lys Gly Arg Ala Gly Pro Ala Leu Ala Ala
            100                 105                 110

Ala Gly Ile Gly Ser Phe Phe Ala Gly Cys Val Gly Thr Val Ile Leu
        115                 120                 125

Ala Ala Phe Ala Pro Pro Leu Thr Glu Val Ala Phe Lys Phe Gly Pro
    130                 135                 140

Ala Glu Tyr Phe Ser Leu Met Thr Leu Gly Leu Ile Gly Ala Val Val
145                 150                 155                 160

Leu Ala Ser Gly Ser Leu Leu Lys Ala Ile Ala Met Ile Val Leu Gly
                165                 170                 175

Leu Leu Leu Gly Met Val Gly Thr Asp Val Asn Ser Gly Val Ala Arg
            180                 185                 190

Tyr Ser Phe Asp Ile Pro Glu Leu Thr Asp Gly Ile Asp Phe Val Val
        195                 200                 205

Ile Ala Met Gly Val Phe Gly Tyr Gly Glu Ile Ile Ala Asn Leu Ser
    210                 215                 220

Lys Pro Asp Asp Glu Arg Glu Val Phe Ala Ala Lys Val Thr Gly Leu
225                 230                 235                 240

Leu Pro Thr Ser Glu Asp Phe Lys Arg Met Leu Pro Ala Met Leu Arg
                245                 250                 255

Gly Thr Ala Leu Gly Ser Ala Leu Gly Ile Leu Pro Gly Gly Gly Ala
            260                 265                 270

Met Leu Ser Ala Phe Ala Ala Tyr Thr Ile Glu Lys Lys Thr Lys Leu
        275                 280                 285
```

```
Lys Pro Gly Glu Val Pro Phe Gly Gln Gly Asn Ile Arg Gly Val Cys
    290                 295                 300
Ala Pro Glu Ser Ala Asn Asn Ala Gly Ser Gln Thr Ser Phe Ile Pro
305                 310                 315                 320
Leu Leu Thr Leu Gly Ile Pro Pro Asn Ala Val Met Ala Leu Met Val
                325                 330                 335
Gly Ala Met Thr Ile His Asn Ile Gln Pro Gly Pro Gln Val Met Thr
                340                 345                 350
Ser Asn Pro Glu Leu Phe Trp Gly Leu Ile Ala Ser Met Ile Gly Asn
            355                 360                 365
Leu Met Leu Ile Ile Leu Asn Leu Pro Leu Ile Gly Val Trp Ile Lys
    370                 375                 380
Leu Leu Thr Val Pro Tyr Arg Trp Leu Phe Pro Ser Ile Val Leu Phe
385                 390                 395                 400
Cys Ala Ile Gly Val Tyr Gly Thr Asn Asn Asn Val Trp Asp Val Trp
                405                 410                 415
Met Val Gly Ile Phe Gly Phe Ile Gly Tyr Val Phe His Lys Leu Gly
                420                 425                 430
Thr Glu Pro Ala Pro Leu Leu Leu Gly Phe Ile Leu Gly Pro Met Met
            435                 440                 445
Glu Glu Asn Leu Arg Arg Ala Leu Leu Leu Ser Arg Gly Asp Trp Ser
    450                 455                 460
Val Phe Val Thr Arg Pro Ile Ser Ala Cys Leu Leu Ala Ala Ala Val
465                 470                 475                 480
Val Leu Leu Val Ile Val Leu Met Pro Ala Val Lys Asn Lys Arg Glu
                485                 490                 495
Glu Ala Phe Val Glu Asp
            500

<210> SEQ ID NO 18
<211> LENGTH: 31
<212> TYPE: DNA
<213> ORGANISM: Artificial Sequence
<220> FEATURE:
<223> OTHER INFORMATION: oCJ289

<400> SEQUENCE: 18
ctaactcaca ttaattgcgt tgcgctcact g                                    31

<210> SEQ ID NO 19
<211> LENGTH: 45
<212> TYPE: DNA
<213> ORGANISM: Artificial Sequence
<220> FEATURE:
<223> OTHER INFORMATION: oCJ345

<400> SEQUENCE: 19
gaattcctgc agtctagagg atccctagct tcacgctgcc gcaag                    45

<210> SEQ ID NO 20
<211> LENGTH: 19
<212> TYPE: DNA
<213> ORGANISM: Artificial Sequence
<220> FEATURE:
<223> OTHER INFORMATION: oIP002

<400> SEQUENCE: 20
atcggcattt tcttttgcg                                                 19
```

```
<210> SEQ ID NO 21
<211> LENGTH: 20
<212> TYPE: DNA
<213> ORGANISM: Artificial Sequence
<220> FEATURE:
<223> OTHER INFORMATION: oIP018

<400> SEQUENCE: 21
atttaagcac tgcactcacc                                               20

<210> SEQ ID NO 22
<211> LENGTH: 19
<212> TYPE: DNA
<213> ORGANISM: Artificial Sequence
<220> FEATURE:
<223> OTHER INFORMATION: oIP031

<400> SEQUENCE: 22
agcaaggtga gatgacagg                                                19

<210> SEQ ID NO 23
<211> LENGTH: 23
<212> TYPE: DNA
<213> ORGANISM: Artificial Sequence
<220> FEATURE:
<223> OTHER INFORMATION: oIP037

<400> SEQUENCE: 23
atggctaaaa tgagaatatc acc                                           23

<210> SEQ ID NO 24
<211> LENGTH: 50
<212> TYPE: DNA
<213> ORGANISM: Artificial Sequence
<220> FEATURE:
<223> OTHER INFORMATION: oIP038

<400> SEQUENCE: 24
acagctatga ccatgattac gccaagcttg agtgcttgga ttctcaccaa              50

<210> SEQ ID NO 25
<211> LENGTH: 20
<212> TYPE: DNA
<213> ORGANISM: Artificial Sequence
<220> FEATURE:
<223> OTHER INFORMATION: oIP042.1

<400> SEQUENCE: 25
gtgaattcga gctcggtacc                                               20

<210> SEQ ID NO 26
<211> LENGTH: 23
<212> TYPE: DNA
<213> ORGANISM: Artificial Sequence
<220> FEATURE:
<223> OTHER INFORMATION: oIP043

<400> SEQUENCE: 26
ggtgatattc tcattttagc cat                                           23

<210> SEQ ID NO 27
<211> LENGTH: 46
<212> TYPE: DNA
<213> ORGANISM: Artificial Sequence
<220> FEATURE:
<223> OTHER INFORMATION: oIP089
```

```
<400> SEQUENCE: 27
cgttttattt gatgtctggt tagctggcat gttttaaata gtcaag              46

<210> SEQ ID NO 28
<211> LENGTH: 43
<212> TYPE: DNA
<213> ORGANISM: Artificial Sequence
<220> FEATURE:
<223> OTHER INFORMATION: oIP090

<400> SEQUENCE: 28
gactatttaa aacatgccag ctaaccagac atcaaataaa acg                 43

<210> SEQ ID NO 29
<211> LENGTH: 18
<212> TYPE: DNA
<213> ORGANISM: Artificial Sequence
<220> FEATURE:
<223> OTHER INFORMATION: oIP096

<400> SEQUENCE: 29
taatgcaagc acgtgagc                                             18

<210> SEQ ID NO 30
<211> LENGTH: 56
<212> TYPE: DNA
<213> ORGANISM: Artificial Sequence
<220> FEATURE:
<223> OTHER INFORMATION: oIP117

<400> SEQUENCE: 30
gtgaattcga gctcggtacc cggggatccg tttaaaccaa attacgcagc tcattc   56

<210> SEQ ID NO 31
<211> LENGTH: 42
<212> TYPE: DNA
<213> ORGANISM: Artificial Sequence
<220> FEATURE:
<223> OTHER INFORMATION: oIP118

<400> SEQUENCE: 31
gctctctttt tgttttaact agttcaatct tctacaaagg cc                  42

<210> SEQ ID NO 32
<211> LENGTH: 48
<212> TYPE: DNA
<213> ORGANISM: Artificial Sequence
<220> FEATURE:
<223> OTHER INFORMATION: oIP119

<400> SEQUENCE: 32
ggcctttgta aagattgaa ctagttaaaa caaaagaga gcgattag               48

<210> SEQ ID NO 33
<211> LENGTH: 59
<212> TYPE: DNA
<213> ORGANISM: Artificial Sequence
<220> FEATURE:
<223> OTHER INFORMATION: oIP120

<400> SEQUENCE: 33
aacagctatg accatgatta cgccaagctt gtttaaacag gcataaggat attgcaatg 59

<210> SEQ ID NO 34
```

```
<211> LENGTH: 42
<212> TYPE: DNA
<213> ORGANISM: Artificial Sequence
<220> FEATURE:
<223> OTHER INFORMATION: oIP128

<400> SEQUENCE: 34
ctcagaaatt acctaataac tggaaacttt attttgaaaa tg                          42

<210> SEQ ID NO 35
<211> LENGTH: 42
<212> TYPE: DNA
<213> ORGANISM: Artificial Sequence
<220> FEATURE:
<223> OTHER INFORMATION: oIP129

<400> SEQUENCE: 35
cattttcaaa ataaagtttc cagttattag gtaatttctg ag                          42

<210> SEQ ID NO 36
<211> LENGTH: 39
<212> TYPE: DNA
<213> ORGANISM: Artificial Sequence
<220> FEATURE:
<223> OTHER INFORMATION: oIP130

<400> SEQUENCE: 36
gcagaacaac gtaaagttcg tcttaaacaa gctaatctg                              39

<210> SEQ ID NO 37
<211> LENGTH: 39
<212> TYPE: DNA
<213> ORGANISM: Artificial Sequence
<220> FEATURE:
<223> OTHER INFORMATION: oIP131

<400> SEQUENCE: 37
cagattagct tgtttaagac gaactttacg ttgttctgc                              39

<210> SEQ ID NO 38
<211> LENGTH: 38
<212> TYPE: DNA
<213> ORGANISM: Artificial Sequence
<220> FEATURE:
<223> OTHER INFORMATION: oIP145

<400> SEQUENCE: 38
ggttcgcttg ctgtccattc atgcctgcat ttcttgtc                               38

<210> SEQ ID NO 39
<211> LENGTH: 44
<212> TYPE: DNA
<213> ORGANISM: Artificial Sequence
<220> FEATURE:
<223> OTHER INFORMATION: oIP146

<400> SEQUENCE: 39
cgcaaaagaa aatgccgatg ttaaaacaaa aagagagcga ttag                        44

<210> SEQ ID NO 40
<211> LENGTH: 52
<212> TYPE: DNA
<213> ORGANISM: Artificial Sequence
<220> FEATURE:
<223> OTHER INFORMATION: oIP160

<400> SEQUENCE: 40
```
cctacaggtc accactagcg gaacggcgat gtgaaaatta aaagtcaaaa ag        52

<210> SEQ ID NO 41
<211> LENGTH: 52
<212> TYPE: DNA
<213> ORGANISM: Artificial Sequence
<220> FEATURE:
<223> OTHER INFORMATION: oIP161

<400> SEQUENCE: 41 cttttgact tttaatttc acatcgccgt tccgctagtg gtgacctgta gg        52

<210> SEQ ID NO 42
<211> LENGTH: 47
<212> TYPE: DNA
<213> ORGANISM: Artificial Sequence
<220> FEATURE:
<223> OTHER INFORMATION: oIP162

<400> SEQUENCE: 42
catttatcgc gggttaaccg gtaagcggca tggatcttat tcaaaac        47

<210> SEQ ID NO 43
<211> LENGTH: 47
<212> TYPE: DNA
<213> ORGANISM: Artificial Sequence
<220> FEATURE:
<223> OTHER INFORMATION: oIP163

<400> SEQUENCE: 43
gttttgaata agatccatgc cgcttaccgg ttaacccgcg ataaatg        47

<210> SEQ ID NO 44
<211> LENGTH: 35
<212> TYPE: DNA
<213> ORGANISM: Artificial Sequence
<220> FEATURE:
<223> OTHER INFORMATION: oIP180

<400> SEQUENCE: 44
cgttttattt gatgtctggc gataccgtcg acctc        35

<210> SEQ ID NO 45
<211> LENGTH: 35
<212> TYPE: DNA
<213> ORGANISM: Artificial Sequence
<220> FEATURE:
<223> OTHER INFORMATION: oIP181

<400> SEQUENCE: 45
gaggtcgacg gtatcgccag acatcaaata aaacg        35

<210> SEQ ID NO 46
<211> LENGTH: 16
<212> TYPE: DNA
<213> ORGANISM: Artificial Sequence
<220> FEATURE:
<223> OTHER INFORMATION: oIP182

<400> SEQUENCE: 46
aagggcaaga gccatc        16

<210> SEQ ID NO 47
<211> LENGTH: 22
<212> TYPE: DNA

<213> ORGANISM: Artificial Sequence
<220> FEATURE:
<223> OTHER INFORMATION: oIP183

<400> SEQUENCE: 47
aaaggagaag cttactagta gc                                    22

<210> SEQ ID NO 48
<211> LENGTH: 21
<212> TYPE: DNA
<213> ORGANISM: Artificial Sequence
<220> FEATURE:
<223> OTHER INFORMATION: oIP184

<400> SEQUENCE: 48
gtgtgaaatt gttatccgct c                                     21

<210> SEQ ID NO 49
<211> LENGTH: 55
<212> TYPE: DNA
<213> ORGANISM: Artificial Sequence
<220> FEATURE:
<223> OTHER INFORMATION: oIP185

<400> SEQUENCE: 49
gagcggataa caatttcaca ctggagcgca cacgtgaaaa ttaaaagtca aaaag    55

<210> SEQ ID NO 50
<211> LENGTH: 43
<212> TYPE: DNA
<213> ORGANISM: Artificial Sequence
<220> FEATURE:
<223> OTHER INFORMATION: oIP186

<400> SEQUENCE: 50
gctactagta agcttctcct tttcaatctt ctacaaaggc ctc              43

<210> SEQ ID NO 51
<211> LENGTH: 23
<212> TYPE: DNA
<213> ORGANISM: Artificial Sequence
<220> FEATURE:
<223> OTHER INFORMATION: oIP187

<400> SEQUENCE: 51
actagttaaa acaaaaagag agc                                   23

<210> SEQ ID NO 52
<211> LENGTH: 24
<212> TYPE: DNA
<213> ORGANISM: Artificial Sequence
<220> FEATURE:
<223> OTHER INFORMATION: oIP188

<400> SEQUENCE: 52
gggcccctag tggtgacctg tagg                                  24

<210> SEQ ID NO 53
<211> LENGTH: 47
<212> TYPE: DNA
<213> ORGANISM: Artificial Sequence
<220> FEATURE:
<223> OTHER INFORMATION: oIP189

<400> SEQUENCE: 53
tcctacaggt caccactagg ggcccgagct gttgacaatt aatcatc          47

<210> SEQ ID NO 54
<211> LENGTH: 46
<212> TYPE: DNA
<213> ORGANISM: Artificial Sequence
<220> FEATURE:
<223> OTHER INFORMATION: oIP190

<400> SEQUENCE: 54
tcgctctctt tttgttttaa ctagttcaat cttctacaaa ggcctc         46

<210> SEQ ID NO 55
<211> LENGTH: 53
<212> TYPE: DNA
<213> ORGANISM: Artificial Sequence
<220> FEATURE:
<223> OTHER INFORMATION: oIP262

<400> SEQUENCE: 55
gccctgaggc ctgcagcggc cgctactagt ttacctaggt gtgaattcag aac    53

<210> SEQ ID NO 56
<211> LENGTH: 23
<212> TYPE: DNA
<213> ORGANISM: Artificial Sequence
<220> FEATURE:
<223> OTHER INFORMATION: oIP291

<400> SEQUENCE: 56
gagctgttga caattaatca tcc         23

<210> SEQ ID NO 57
<211> LENGTH: 49
<212> TYPE: DNA
<213> ORGANISM: Artificial Sequence
<220> FEATURE:
<223> OTHER INFORMATION: oIP292

<400> SEQUENCE: 57
gatgattaat tgtcaacagc tcgggccctt aaagttttac gtttgctgc       49

<210> SEQ ID NO 58
<211> LENGTH: 47
<212> TYPE: DNA
<213> ORGANISM: Artificial Sequence
<220> FEATURE:
<223> OTHER INFORMATION: oIP305

<400> SEQUENCE: 58
agatctaagc ttctgcaggt cgactctaga cggatccccc tcaagtc         47

<210> SEQ ID NO 59
<211> LENGTH: 45
<212> TYPE: DNA
<213> ORGANISM: Artificial Sequence
<220> FEATURE:
<223> OTHER INFORMATION: oIP306

<400> SEQUENCE: 59
tcgctctctt tttgttttaa ctagttacat gcttgcaata agacc           45

<210> SEQ ID NO 60
<211> LENGTH: 15
<212> TYPE: DNA
<213> ORGANISM: Artificial Sequence
<220> FEATURE:

<223> OTHER INFORMATION: oIP340

<400> SEQUENCE: 60
tgagcgggac tctgg                                                    15

<210> SEQ ID NO 61
<211> LENGTH: 16
<212> TYPE: DNA
<213> ORGANISM: Artificial Sequence
<220> FEATURE:
<223> OTHER INFORMATION: oIP341

<400> SEQUENCE: 61
gcagcgtgaa gctagg                                                   16

<210> SEQ ID NO 62
<211> LENGTH: 39
<212> TYPE: DNA
<213> ORGANISM: Artificial Sequence
<220> FEATURE:
<223> OTHER INFORMATION: oIP342

<400> SEQUENCE: 62
gatccctagc ttcacgctgc cctgttatcc ctactcgag                          39

<210> SEQ ID NO 63
<211> LENGTH: 37
<212> TYPE: DNA
<213> ORGANISM: Artificial Sequence
<220> FEATURE:
<223> OTHER INFORMATION: oIP343

<400> SEQUENCE: 63 gaacccaga gtcccgctca tttgccgact accttgg                             37

<210> SEQ ID NO 64
<211> LENGTH: 42
<212> TYPE: DNA
<213> ORGANISM: Artificial Sequence
<220> FEATURE:
<223> OTHER INFORMATION: oIP344

<400> SEQUENCE: 64
taaaaacgca aagaaaatg ccgatgtcta gctatcgcca tg                       42

<210> SEQ ID NO 65
<211> LENGTH: 46
<212> TYPE: DNA
<213> ORGANISM: Artificial Sequence
<220> FEATURE:
<223> OTHER INFORMATION: oIP345

<400> SEQUENCE: 65
taacagggca gcgtgaagct agggattaaa gttttacgtt tgctgc                  46

<210> SEQ ID NO 66
<211> LENGTH: 18
<212> TYPE: DNA
<213> ORGANISM: Artificial Sequence
<220> FEATURE:
<223> OTHER INFORMATION: oIP346

<400> SEQUENCE: 66
tccctagctt cacgctgc                                                 18

<210> SEQ ID NO 67
<211> LENGTH: 55
<212> TYPE: DNA
<213> ORGANISM: Artificial Sequence
<220> FEATURE:
<223> OTHER INFORMATION: oIP393

<400> SEQUENCE: 67
gtgaattcga gctcggtacc cggggatccg tttaaaccac tgtcaaagct caacc    55

<210> SEQ ID NO 68
<211> LENGTH: 60
<212> TYPE: DNA
<213> ORGANISM: Artificial Sequence
<220> FEATURE:
<223> OTHER INFORMATION: oIP394

<400> SEQUENCE: 68
aacagctatg accatgatta cgccaagctt gtttaaactt attggcatct ttgggtttac    60

<210> SEQ ID NO 69
<211> LENGTH: 42
<212> TYPE: DNA
<213> ORGANISM: Artificial Sequence
<220> FEATURE:
<223> OTHER INFORMATION: oIP395

<400> SEQUENCE: 69
gcagcgtgaa gctagggaca taggaaagag tatactcaac tc    42

<210> SEQ ID NO 70
<211> LENGTH: 43
<212> TYPE: DNA
<213> ORGANISM: Artificial Sequence
<220> FEATURE:
<223> OTHER INFORMATION: oIP396

<400> SEQUENCE: 70
cgcaaaagaa aatgccgatt aaaaaatatc gcaaaatgcg tac    43

<210> SEQ ID NO 71
<211> LENGTH: 42
<212> TYPE: DNA
<213> ORGANISM: Artificial Sequence
<220> FEATURE:
<223> OTHER INFORMATION: oIP397

<400> SEQUENCE: 71
attttgcgat attttttaca taggaaagag tatactcaac tc    42

<210> SEQ ID NO 72
<211> LENGTH: 43
<212> TYPE: DNA
<213> ORGANISM: Artificial Sequence
<220> FEATURE:
<223> OTHER INFORMATION: oIP398

<400> SEQUENCE: 72
gagtatactc tttcctatgt aaaaaatatc gcaaaatgcg tac    43

<210> SEQ ID NO 73
<211> LENGTH: 57
<212> TYPE: DNA
<213> ORGANISM: Artificial Sequence
<220> FEATURE:
<223> OTHER INFORMATION: oIP402

<400> SEQUENCE: 73
gtgaattcga gctcggtacc cggggatccg tttaaacaga tactgtttga tcagtgg    57

<210> SEQ ID NO 74
<211> LENGTH: 57
<212> TYPE: DNA
<213> ORGANISM: Artificial Sequence
<220> FEATURE:
<223> OTHER INFORMATION: oIP403

<400> SEQUENCE: 74
aacagctatg accatgatta cgccaagctt gtttaaacca ggtactttac ctgaagc    57

<210> SEQ ID NO 75
<211> LENGTH: 43
<212> TYPE: DNA
<213> ORGANISM: Artificial Sequence
<220> FEATURE:
<223> OTHER INFORMATION: oIP404

<400> SEQUENCE: 75
gcagcgtgaa gctagggata acttataaat gcttatacac ttc    43

<210> SEQ ID NO 76
<211> LENGTH: 43
<212> TYPE: DNA
<213> ORGANISM: Artificial Sequence
<220> FEATURE:
<223> OTHER INFORMATION: oIP405

<400> SEQUENCE: 76
cgcaaaagaa aatgccgatc atagctatat tcctttagca aag    43

<210> SEQ ID NO 77
<211> LENGTH: 25
<212> TYPE: DNA
<213> ORGANISM: Artificial Sequence
<220> FEATURE:
<223> OTHER INFORMATION: oIP417

<400> SEQUENCE: 77
ggaagctttc tatcatgtaa gttgc    25

<210> SEQ ID NO 78
<211> LENGTH: 25
<212> TYPE: DNA
<213> ORGANISM: Artificial Sequence
<220> FEATURE:
<223> OTHER INFORMATION: oIP418

<400> SEQUENCE: 78
cttacatgat agaaagcttc ccaac    25

<210> SEQ ID NO 79
<211> LENGTH: 23
<212> TYPE: DNA
<213> ORGANISM: Artificial Sequence
<220> FEATURE:
<223> OTHER INFORMATION: oIP419

<400> SEQUENCE: 79
gagagcaaca acaggtctgc tcc    23

<210> SEQ ID NO 80
<211> LENGTH: 23

```
<212> TYPE: DNA
<213> ORGANISM: Artificial Sequence
<220> FEATURE:
<223> OTHER INFORMATION: oIP420

<400> SEQUENCE: 80
ggagcagacc tgttgttgct ctc                                           23

<210> SEQ ID NO 81
<211> LENGTH: 23
<212> TYPE: DNA
<213> ORGANISM: Artificial Sequence
<220> FEATURE:
<223> OTHER INFORMATION: oIP421

<400> SEQUENCE: 81
gttggaacac attcggccat gag                                           23

<210> SEQ ID NO 82
<211> LENGTH: 30
<212> TYPE: DNA
<213> ORGANISM: Artificial Sequence
<220> FEATURE:
<223> OTHER INFORMATION: oIP422

<400> SEQUENCE: 82
ctcatggccg aatgtgttcc aacaaaatac                                    30

<210> SEQ ID NO 83
<211> LENGTH: 25
<212> TYPE: DNA
<213> ORGANISM: Artificial Sequence
<220> FEATURE:
<223> OTHER INFORMATION: oIP423

<400> SEQUENCE: 83
gttttctttt ggtaaacagt gctgg                                         25

<210> SEQ ID NO 84
<211> LENGTH: 31
<212> TYPE: DNA
<213> ORGANISM: Artificial Sequence
<220> FEATURE:
<223> OTHER INFORMATION: oIP424

<400> SEQUENCE: 84
ccagcactgt ttaccaaaga aaaacaatat g                                  31

<210> SEQ ID NO 85
<211> LENGTH: 24
<212> TYPE: DNA
<213> ORGANISM: Artificial Sequence
<220> FEATURE:
<223> OTHER INFORMATION: oIP425

<400> SEQUENCE: 85
atagccaaca gtacagccag cctg                                          24

<210> SEQ ID NO 86
<211> LENGTH: 28
<212> TYPE: DNA
<213> ORGANISM: Artificial Sequence
<220> FEATURE:
<223> OTHER INFORMATION: oIP426

<400> SEQUENCE: 86
```

```
caggctggct gtactgttgg ctatattg                                          28

<210> SEQ ID NO 87
<211> LENGTH: 50
<212> TYPE: DNA
<213> ORGANISM: Artificial Sequence
<220> FEATURE:
<223> OTHER INFORMATION: oIP427

<400> SEQUENCE: 87
ctcagcttta atactgttta aactataaga gagcaatatc aggtctgctc                  50

<210> SEQ ID NO 88
<211> LENGTH: 51
<212> TYPE: DNA
<213> ORGANISM: Artificial Sequence
<220> FEATURE:
<223> OTHER INFORMATION: oIP428

<400> SEQUENCE: 88
ttaaacagta ttaaagctga gtttaattta agtacagttg gagctggaat g                51

<210> SEQ ID NO 89
<211> LENGTH: 24
<212> TYPE: DNA
<213> ORGANISM: Artificial Sequence
<220> FEATURE:
<223> OTHER INFORMATION: oIP475

<400> SEQUENCE: 89
aacttctaaa aattaacgca tagc                                              24

<210> SEQ ID NO 90
<211> LENGTH: 21
<212> TYPE: DNA
<213> ORGANISM: Artificial Sequence
<220> FEATURE:
<223> OTHER INFORMATION: oIP476

<400> SEQUENCE: 90
gtcactgggt atgagaatat g                                                 21

<210> SEQ ID NO 91
<211> LENGTH: 20
<212> TYPE: DNA
<213> ORGANISM: Artificial Sequence
<220> FEATURE:
<223> OTHER INFORMATION: oRJ17-01

<400> SEQUENCE: 91
tgctatggag gtcaggtatg                                                   20

<210> SEQ ID NO 92
<211> LENGTH: 29
<212> TYPE: DNA
<213> ORGANISM: Artificial Sequence
<220> FEATURE:
<223> OTHER INFORMATION: oRJ17-03

<400> SEQUENCE: 92
gatatcattc aggacgagcc tcagactcc                                         29

<210> SEQ ID NO 93
<211> LENGTH: 35
<212> TYPE: DNA
<213> ORGANISM: Artificial Sequence
```

```
<220> FEATURE:
<223> OTHER INFORMATION: oRJ17-04

<400> SEQUENCE: 93
aatcatacct gacctccata gcagaaagtc aaaag                            35

<210> SEQ ID NO 94
<211> LENGTH: 45
<212> TYPE: DNA
<213> ORGANISM: Artificial Sequence
<220> FEATURE:
<223> OTHER INFORMATION: oRJ17-08

<400> SEQUENCE: 94
gaggctcgtc ctgaatgata tcttacctag gtgtgaattc agaac                 45

<210> SEQ ID NO 95
<211> LENGTH: 36
<212> TYPE: DNA
<213> ORGANISM: Artificial Sequence
<220> FEATURE:
<223> OTHER INFORMATION: oRJ012

<400> SEQUENCE: 95
aaggagatat acatatggct agcaaaggag aagaac                           36

<210> SEQ ID NO 96
<211> LENGTH: 21
<212> TYPE: DNA
<213> ORGANISM: Artificial Sequence
<220> FEATURE:
<223> OTHER INFORMATION: oRJ112

<400> SEQUENCE: 96
catggcatgg atgagctcta c                                           21

<210> SEQ ID NO 97
<211> LENGTH: 45
<212> TYPE: DNA
<213> ORGANISM: Artificial Sequence
<220> FEATURE:
<223> OTHER INFORMATION: oRJ122

<400> SEQUENCE: 97
tttgctagcc atatgtatat ctccttcttg tgtggggaac tgcag                 45

<210> SEQ ID NO 98
<211> LENGTH: 40
<212> TYPE: DNA
<213> ORGANISM: Artificial Sequence
<220> FEATURE:
<223> OTHER INFORMATION: oRJ125

<400> SEQUENCE: 98
tgctatggag gtcaggtatg attctacaac ccctgcggat                       40

<210> SEQ ID NO 99
<211> LENGTH: 24
<212> TYPE: DNA
<213> ORGANISM: Artificial Sequence
<220> FEATURE:
<223> OTHER INFORMATION: oRJ130

<400> SEQUENCE: 99
ttacctaggt gtgaattcag aacc                                        24
```

```
<210> SEQ ID NO 100
<211> LENGTH: 65
<212> TYPE: DNA
<213> ORGANISM: Artificial Sequence
<220> FEATURE:
<223> OTHER INFORMATION: oRJ146
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t

<400> SEQUENCE: 100
tttgctagcc atatgtatat ctccttcttg tgtggngaac tgcantntna ggatgtcgta    60
ctttg                                                               65

<210> SEQ ID NO 101
<211> LENGTH: 58
<212> TYPE: DNA
<213> ORGANISM: Artificial Sequence
<220> FEATURE:
<223> OTHER INFORMATION: oRJ147
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t

<400> SEQUENCE: 101
gttttcaaca tttttgcgca tagcgcaaaa acaggtntna nacaaagtac gacatcct     58

<210> SEQ ID NO 102
<211> LENGTH: 21
<212> TYPE: DNA
<213> ORGANISM: Artificial Sequence
<220> FEATURE:
<223> OTHER INFORMATION: oRJ150

<400> SEQUENCE: 102
atgcgcaaaa atgttgaaaa c                                             21

<210> SEQ ID NO 103
<211> LENGTH: 23
<212> TYPE: DNA
<213> ORGANISM: Artificial Sequence
<220> FEATURE:
<223> OTHER INFORMATION: oRJ151

<400> SEQUENCE: 103
caaagtacga catccttaca atg                                           23
```

```
<210> SEQ ID NO 104
<211> LENGTH: 48
<212> TYPE: DNA
<213> ORGANISM: Artificial Sequence
<220> FEATURE:
<223> OTHER INFORMATION: oRJ152
<220> FEATURE:
<221> NAME/KEY: misc_feature
<222> LOCATION: (24)..(29)
<223> OTHER INFORMATION: n is a, c, g, or t

<400> SEQUENCE: 104
cattgtaagg atgtcgtact ttgnnnnnna cctgttttg cgctatgc              48

<210> SEQ ID NO 105
<211> LENGTH: 47
<212> TYPE: DNA
<213> ORGANISM: Artificial Sequence
<220> FEATURE:
<223> OTHER INFORMATION: oRJ153
<220> FEATURE:
<221> NAME/KEY: misc_feature
<222> LOCATION: (25)..(30)
<223> OTHER INFORMATION: n is a, c, g, or t

<400> SEQUENCE: 105
gtttaacaca aagtacgaca tcctnnnnnn gcagttcccc acacaag              47

<210> SEQ ID NO 106
<211> LENGTH: 24
<212> TYPE: DNA
<213> ORGANISM: Artificial Sequence
<220> FEATURE:
<223> OTHER INFORMATION: oRJ154

<400> SEQUENCE: 106
aggatgtcgt actttgtgtt aaac                                       24

<210> SEQ ID NO 107
<211> LENGTH: 2325
<212> TYPE: DNA
<213> ORGANISM: Artificial Sequence
<220> FEATURE:
<223> OTHER INFORMATION: IP_tph_tpi-Opt_ADP1-1

<400> SEQUENCE: 107
gtgaattcga gctcggtacc cgggccagac atcaaataaa acgaaaggct cagtcgaaag    60
actgggcctt tcgttttatc tgttgtttgt cggtgaacgc tctcattaat taatccagag   120
gcatgagctg ttgacaatta atcatcggct cgtataatgt gtggaattgt gagcggataa   180
caatttcaca caggagagtc tatatatgcg taacgaatct atccgtcgtc gtgaagcgtt   240
aattggtatc gctgcagcag ttgcagcaac tggttcactc gctcaaagta accaaccact   300
gaaaatcgtt gtgccttttt ctgcaggtgg tacagcggac gtattaccac gtcttgtcgc   360
tgaaaaaatc cgtgccgatt atgctggtgg tgttatcatc gaaaacaaac caggtgcagg   420
tggtaatatt ggtgcagatc tagttttccg tgctccacca gacggtatga cggttttagc   480
ttcaccacct ggtcctatcg ctattaatca caatctttat caaaaattat ctttcgatcc   540
tactcgttgg gtaccagtaa ccattctggc aacagttcct aacgtacttg taattaaccc   600
aaaactacct gttaaaagcc ttggcgaatt tatcgcatac gcaaaagcaa atccaaagaa   660
agtaaccgta gcgactcaag gtgacggttc tacttcacac cttacagcag caatgttat   720 gcaattaact ggtacagaac taactgttat cccatacaaa ggtacagcac cagctttaat   780
```

| | |
|---|---|
| cgatcttatt ggtggtaatg tagacgtgtt tttcgataat atcagctctt ctgcaactta | 840 |
| tcaccaagca ggaaaagttc gtattcttgc agttgctgat gaacaacgtt cacaaattct | 900 |
| tccacaagtt ccaacgttcg cagaacaaca gtggccagca atgcaagctg tgacattttt | 960 |
| ctcagtagtg gcacctcctg gtacatcagc agaaatcgca caaaaacttc aaaaacagat | 1020 |
| ggctcttgcc ctttcttcga acgatattcg taagcacttc caggaacaag gtgctgtgcc | 1080 |
| atgtggttgg gatccaagta aaactgctca atttattcgt caggaaaccg aaaaatggaa | 1140 |
| gaaagtactc aaagcagcaa acgtaaaact taagagagg aaagcaatgc aggaaagcat | 1200 |
| tattcaatgg catggtgcga ccaacacacg cgttccattt ggtatctata cagataccgc | 1260 |
| aaatgctgac caagaacaac agcgtattta ccgtggcgaa gtatggaatt accttttgttt | 1320 |
| ggaatcagaa atcccaggag cgggtgattt tcgtaccaca tttgcgggtg aaacacctat | 1380 |
| tgtcgtagtt cgtgatgctg atcaagaaat ttatgctttc gaaaatcgtt gtgctcaccg | 1440 |
| tggtgcttta attgcattag aaaagagcgg tcgtactgat tcttttcaat gtgtttatca | 1500 |
| tgcatggtca tataaccgtc agggtgacct tacgggtgtg gctttcgaaa aaggcgtaaa | 1560 |
| aggtcagggt ggtatgccag ctagtttctg taaagaagaa catggtccac gtaaacttcg | 1620 |
| cgtagcagtg ttctgcggct tggttttcgg ttctttttct gaagacgttc caagtattga | 1680 |
| agattatttg ggtccggaaa tttgtgaacg tatcgaacgt gttctccata gcctgtaga | 1740 |
| agttatcggt cgttttactc agaaattacc taataactgg aaactttatt ttgaaaatgt | 1800 |
| aaaagatagc taccatgcat ctcttttaca catgtttttc acaactttcg aactgaaccg | 1860 |
| tttatctcag aaaggcggtg ttattgtgga tgagtctggc ggccatcatg tatcctatag | 1920 |
| tatgattgat cgtggggcca aggatgattc atataaagat caagctattc gttctgacaa | 1980 |
| tgaacgttat cgtttgaaag atcctagctt actagaaggt tttgaagaat cgaagatgg | 2040 |
| tgtaacgctt caaattctta gcgtattccc agggtttgtt ttgcaacaaa tccaaaacag | 2100 |
| tattgcagtg cgtcagttat tgccaaaaag tatttctagt tctgaattga actggactta | 2160 |
| tttaggttat gccgatgata gcgcagaaca acgtaaagtt cgtcttaaac aagctaatct | 2220 |
| gattggacct gctggattca tttcaatgga agatggtgca gtcggcggtt tcgtgcagcg | 2280 |
| tggtattgca ggcgctgcta accttgatgc agtaatcgaa atggg | 2325 |

<210> SEQ ID NO 108
<211> LENGTH: 2340
<212> TYPE: DNA
<213> ORGANISM: Artificial Sequence
<220> FEATURE:
<223> OTHER INFORMATION: IP_tph_tpi-Opt_ADP1-2

<400> SEQUENCE: 108

| | |
|---|---|
| ccttgatgca gtaatcgaaa tgggcggtga tcatgaaggc agctctgaag gtcgcgctac | 60 |
| tgaaacttca gtacgtggct tttggaaagc atatcgtaaa catatgggac aagaaatgca | 120 |
| ggcatgagga gtccctaaac aatgatcaat gaaatacaga tcgcagcatt taatgcagca | 180 |
| tatgcaaaaa ctattgactc tgatgctatg gaacaatggc ctaccttttt tactaaagat | 240 |
| tgccattatt gtgtaacgaa tgtagataat catgatgagg gttagctgc tggtatagtt | 300 |
| tgggcagatt cacaggacat gttgactgat cgtatctcag ctttgcgtga agcgaacatt | 360 |
| tacgaacgtc accgctatcg tcacatctta ggtctgccat caattcaatc aggtgatgca | 420 |
| acgcaggcat cagctagcac acctttcatg gttcttcgta tcatgcatac tggcgaaacg | 480 |
| gaggttttcg catcgggtga atatctcgat aaattcacta ctattgatgg taaattgcgc | 540 |

```
cttcaggaac gtattgctgt ttgtgactct acagtaaccg ataccttaat ggcattgcca      600
ttatgaaagg aggtaacaat gaacgcaatt gttcaccgcc gtcttgcact tgcaattggt      660
gatccacatg gtattggtcc tgaaatcgca ttgaaagctc ttcaacagct ttcggtaact      720
gaacgtagct taattaaagt atacggtccg tggtctgcac ttgaacaagc agcacgcgtt      780
tgcgaaatgg aaccactctt acaagatatc gtacacgaag aagcaggtac cttgacccaa      840
ccagtacagt ggggtgaaat tacaccacaa gctggtctta gtacagtaca atcagctact      900
gctgcgatcc gtgcatgtga aaatggtgag gtagatgcag ttattgcgtg tccacaccat      960
gaaactgcaa tccaccgtgc tggtatcgcc ttctctggtt atccaagcct tttagcgaat     1020
gtgttgggta tgaacgaaga tcaagttttt cttatgttgg ttggtgctgg tcttcgtatc     1080
gttcatgtga ctctacacga atctgtacgt tctgcacttg aacgtctttc tccacaactt     1140
gttgtaaatg cagcacaagc agcagttcaa acctgtacat tgcttggtgt tcctaaaccg     1200
aaagtggcag tgttcggcat taacccacat gcatcagaag gtcaactttt cggcttggaa     1260
gatagccaaa ttaccgttcc agcagttgaa acccttcgta acgtggtct agctgttgat     1320 ggtccaatgg gtgcggatat ggtactgca caacgtaaac atgatttata tgttgcgatg     1380
cttcatgatc agggtcatat accaattaaa cttcttgcac caaatggtgc gagtgctctc     1440
tcaatcggtg gtcgtgttgt attgtcatca gttggacacg gcagcgcaat ggacatcgct     1500
ggccgtggcg tagctgatgc cactgctctt ttacgtacca ttgctcttct tggcgctcag     1560
ccagtttgag gtccctccca aatgaaccat caaatccaca tccatgactc agatattgca     1620
tttccatgtg cacctggtca atcagttttg gatgcggcct acaagcagg tatcgaattg     1680 ccttatagct gccgtaaagg ttcatgtggg aattgtgcaa gtactctttt agatggtaat     1740
attgcatctt tcaacggtat ggctgttcgt aatgaattat gtgcgtctga acaagtgtta     1800
ttgtgtggtt gcacggcggc atctgatata cgtattcatc cttcttcttt ccgtcgtctt     1860
gacccagaag ctcgtaaacg tttcactgct aaggtatatt caaatactct tgctgctcca     1920
gatgtatctc ttctccgtct ccgtttacct gttggtaaac gtgctaaatt tgaagctggt     1980
caatatttac taatccactt agatgacggt gagagccgta gctacagcat ggcaaatcca     2040
ccacatgaat ctgatggtat caccttacat gttcgtcatg ttccaggtgg gcgttttagt     2100
actattgtac aacaattgaa atcaggagat actttggaca ttgaattacc ttttggttct     2160
attgcgctta aacctgatga cgctcgtcct ctgatctgtg tagctggtgg taccggcttt     2220
gctccaatca aatccgtttt agacgatctc gcgaaacgta agtacagcg cgatatcaca     2280 cttatctggg gcgcacgcaa tccatctggc ttatatcttc catcagctat cgataagtgg     2340
```

<210> SEQ ID NO 109
<211> LENGTH: 2347
<212> TYPE: DNA
<213> ORGANISM: Artificial Sequence
<220> FEATURE:
<223> OTHER INFORMATION: IP_tph_tpi-Opt_ADP1-3

<400> SEQUENCE: 109

```
cttccatcag ctatcgataa gtggcgtaag gtatggccac aattccgtta catcgccgct       60
atcactgatc ttggggatat gccagctgat gcacacgctg gtcgtgtgga cgacgcatta      120
cgtactcatt ttggtaatct gcatgatcat gttgttcatt ttgtggttc gcctgctcta      180 gttcaaagtg tccgtacagc cgcctcggac atgggtctac tagcgcaaga tttccatgca      240
```

```
gatgtatttg caactggtcc tacaggtcac cactaggggg cggaacaaat gaaaattaaa    300
agtcaaaaag attttttttc tggtttgatg ttccttgcag ttggtttagc atttgcaatt    360
ggtgcttcaa attatactat tggtactggt gctcgtatgg gtccaggtta tttccctctt    420
atacttggtg tactgatggc gattctaggt gcagctatct gtgttggtgg tcttactaaa    480
ggtccagagg gtggtgataa aattggtaaa tgggcatggc gtcaagtttt ttttatcttg    540
gcagcaaatt ttgcattcgg cattttgtta gtgggtgtac cagcagttgg tattccacaa    600
tttggtctta ttatcgcaat ttatgcgtta gtcttcatcg cgtctttggg tggccactct    660
ttcaacttca aagaaaccgc gatccttgca acggtgcttg cagttggttc ttacttcgct    720
tttgtttggg cattaaactt acaattccca gtatggccat catttatcgc gggttaatca    780
ggagcatcgt ccatggatct tattcaaaac ttaagtaccg gcttcggtgt ggctttcact    840
ttccaaaatt tgatttattg tttcgttggt tgtcttttag gtactttaat tggcgtactt    900
ccaggcattg gtccagttgc tacaattgca atgttattgc ctgcaaccta tgctttacca    960
ccagtggctg cattgattat gttggctggt atctactatg gtgcgcagta tggtggtagt   1020
actactgcta ttttggtaaa tcttccgggt gaatcttctt ctgtagtcac cgttatcgat   1080
ggttaccaaa tggctcgtaa aggtcgtgca ggtccagcgc ttgctgctgc tggtattggt   1140 tctttttttcg caggttgtgt tggtacagtg atcttagcgg cttttcgctcc acctctcacg   1200 gaagttgcat tcaagtttgg acctgcagag tattttttctt taatgacatt gggtctaatt   1260
ggtgcagttg tccttgcttc aggctctttg ctcaaagcaa ttgcaatgat cgtactcggt   1320
cttttgcttg gcatggttgg tacggacgta aattcaggtg tagcgcgtta ctcatttgac   1380
attccagagc taacagatgg tattgatttt gttgtgatcg caatgggtgt ttttggttac   1440
ggtgaaatta ttgcaaatct ttcaaagcct gatgatgaac gtgaggtttt tgcagcgaaa   1500
gtgactggtc ttcttccaac aagtgaagac ttcaaacgta tgttgccagc aatgttgcgt   1560
ggtacagcat taggttcagc tttaggaatt ttgccaggtg gtggtgctat gttgagtgca   1620
tttgcagctt atacaattga aaaaaaaacc aaattaaaac ctggtgaagt accatttggt   1680
cagggcaata ttcgtggcgt ttgcgctccg gaatcagcaa acaacgctgg tagtcaaaca   1740
tctttcattc cactgttaac attgggcatt cctccaaacg ccgtaatggc tctcatggta   1800
ggcgcaatga ctattcacaa cattcaacca ggaccacaag tgatgacatc taaccctgaa   1860
ctattttggg gtcttattgc aagcatgtgg attggtaatt tgatgttaat tattttgaac   1920
ctaccactta tcggtgtgtg gatcaagttg cttacagtac catatcgttg gttgtttcca   1980
tctatcgtat tattttgtgc aattggtgtg tatggtacta ataacaacgt ttgggatgtt   2040
tggatggtag gtatttttgg tttcattggt tatgtattcc acaagttagg gactgaacct   2100
gctcctttgt tgttgggttt cattttaggt ccaatgatgg aagaaaacct tcgccgtgct   2160
ctattgctat cgcgtggcga ctggtctgta tttgttacgc gtccaattag tgcatgctta   2220
ctggcagcgg ctgttgtgct tcttgtaatc gttcttatgc ctgcagttaa gaataaacgt   2280
gaagaggcct ttgtagaaga ttgactcgag gacgaggcgc atacatggct aaaatgagaa   2340
tatcacc                                                            2347
```

<210> SEQ ID NO 110
<211> LENGTH: 21
<212> TYPE: DNA
<213> ORGANISM: Artificial Sequence
<220> FEATURE:
<223> OTHER INFORMATION: primer

<400> SEQUENCE: 110
gctcgacgcc ttctatttca a                                    21

<210> SEQ ID NO 111
<211> LENGTH: 26
<212> TYPE: DNA
<213> ORGANISM: Artificial Sequence
<220> FEATURE:
<223> OTHER INFORMATION: primer

<400> SEQUENCE: 111
tttacgtcgc attctattgt cttctt                               26

<210> SEQ ID NO 112
<211> LENGTH: 20
<212> TYPE: DNA
<213> ORGANISM: Artificial Sequence
<220> FEATURE:
<223> OTHER INFORMATION: primer

<400> SEQUENCE: 112
tcaaccacag cagcgccagg                                      20

<210> SEQ ID NO 113
<211> LENGTH: 19
<212> TYPE: DNA
<213> ORGANISM: Artificial Sequence
<220> FEATURE:
<223> OTHER INFORMATION: primer

<400> SEQUENCE: 113
gcgttggcta cccgtgata                                       19

<210> SEQ ID NO 114
<211> LENGTH: 18
<212> TYPE: DNA
<213> ORGANISM: Artificial Sequence
<220> FEATURE:
<223> OTHER INFORMATION: primer

<400> SEQUENCE: 114
ggaagcggtc agcccatt                                        18

<210> SEQ ID NO 115
<211> LENGTH: 16
<212> TYPE: DNA
<213> ORGANISM: Artificial Sequence
<220> FEATURE:
<223> OTHER INFORMATION: primer

<400> SEQUENCE: 115
tgaagagctt ggcggc                                          16

<210> SEQ ID NO 116
<211> LENGTH: 21
<212> TYPE: DNA
<213> ORGANISM: Artificial Sequence
<220> FEATURE:
<223> OTHER INFORMATION: primer

<400> SEQUENCE: 116
tggacctgct ggattcattt c                                    21

<210> SEQ ID NO 117

```
<211> LENGTH: 20
<212> TYPE: DNA
<213> ORGANISM: Artificial Sequence
<220> FEATURE:
<223> OTHER INFORMATION: primer

<400> SEQUENCE: 117
tcaccgccca tttcgattac                                                       20

<210> SEQ ID NO 118
<211> LENGTH: 24
<212> TYPE: DNA
<213> ORGANISM: Artificial Sequence
<220> FEATURE:
<223> OTHER INFORMATION: primer

<400> SEQUENCE: 118
ctgcaatacc acgctgcacg aaac                                                  24

<210> SEQ ID NO 119
<211> LENGTH: 20
<212> TYPE: DNA
<213> ORGANISM: Artificial Sequence
<220> FEATURE:
<223> OTHER INFORMATION: primer

<400> SEQUENCE: 119
attcggccat gagggtattg                                                       20

<210> SEQ ID NO 120
<211> LENGTH: 23
<212> TYPE: DNA
<213> ORGANISM: Artificial Sequence
<220> FEATURE:
<223> OTHER INFORMATION: primer

<400> SEQUENCE: 120
ccttggattg actcagagct tta                                                   23

<210> SEQ ID NO 121
<211> LENGTH: 27
<212> TYPE: DNA
<213> ORGANISM: Artificial Sequence
<220> FEATURE:
<223> OTHER INFORMATION: primer

<400> SEQUENCE: 121
acctaaaccg agtgaagcga agaaacg                                               27
```